United States Patent [19]
Oku et al.

[11] Patent Number: 6,083,961
[45] Date of Patent: *Jul. 4, 2000

[54] BENZIMIDAZOLE COMPOUNDS AS BRADYKININ ANTAGONISTS

[75] Inventors: Teruo Oku; Hiroshi Kayakiri; Shigeki Satoh, all of Tsukuba; Yoshito Abe, Ibaraki; Yuki Sawada; Takayuki Inoue, both of Tsukuba; Hirokazu Tanaka, Takarazuka, all of Japan

[73] Assignee: Fujisawa Pharmaceutical Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/776,518
[22] PCT Filed: Jul. 25, 1995
[86] PCT No.: PCT/JP95/01478
  § 371 Date: Feb. 3, 1997
  § 102(e) Date: Feb. 3, 1997
[87] PCT Pub. No.: WO96/04251
  PCT Pub. Date: Feb. 15, 1996

[30] Foreign Application Priority Data

Aug. 3, 1994 [JP] Japan ................................ 6-182541
Mar. 16, 1995 [JP] Japan ................................ 7-057427

[51] Int. Cl.[7] ............... A61K 31/415; A61K 31/42; A61K 31/44; A61K 31/34; C07D 401/12; C07D 401/14; C07D 403/12; C07D 405/12
[52] U.S. Cl. ............... 514/338; 544/89; 546/14; 546/165; 546/271.7; 546/256; 546/273.4; 546/273.7; 548/217; 548/304.4; 548/306.1; 548/306.4; 548/305.1; 548/307.1; 548/307.4; 548/309.4; 548/310.1; 548/310.4; 548/310.7; 549/471; 514/230.2; 514/314; 514/333; 514/63; 514/375; 514/387; 514/388; 514/394; 514/395; 514/469
[58] Field of Search ............... 546/14, 256, 273.4, 546/273.7; 514/63, 333, 338

[56] References Cited

U.S. PATENT DOCUMENTS 5,106,862 4/1992 Briving et al. ................... 514/394
5,563,162 10/1996 Oku et al. ...................... 514/311
5,574,042 11/1996 Oku et al. ...................... 514/300
5,750,699 5/1998 Oku et al. ...................... 546/121

FOREIGN PATENT DOCUMENTS 0 596 406 5/1994 European Pat. Off. .
0 622 361 11/1994 European Pat. Off. .

*Primary Examiner*—Laura L. Stockton
*Attorney, Agent, or Firm*—Oblon, Spivak, McClelland, Maier & Neustadt, P.C.

[57] ABSTRACT

This invention relates to a heterocyclic compound of the formula:

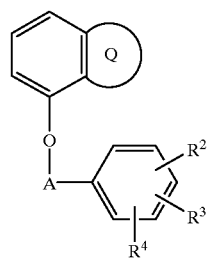

wherein
a group of the formula:

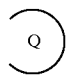

is a group of the formula:

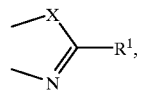

etc.,
X is O, S or N—$R^5$,
$R^1$ is lower alkyl, etc.,
$R^5$ is hydrogen, lower alkyl, etc.,
$R^2$ is hydrogen, halogen, lower alkyl, etc.,
$R^3$ is halogen, lower alkyl, etc.,
$R^4$ is amino optionally having suitable substituent(s), and
A is lower alkylene,
and a salt thereof, to processes for preparation thereof, and to a pharmaceutical composition comprising the same for the prevention and/or the treatment of bradykinin or its analogues mediated diseases in human being or animals.

8 Claims, No Drawings

BENZIMIDAZOLE COMPOUNDS AS BRADYKININ ANTAGONISTS

This application is a 371 PCT/JP95/01478 filed Jul. 25, 1995.

TECHNICAL FIELD

This invention relates to heterocyclic compounds and salts thereof which have activities as bradykinin antagonists and are useful for treating several diseases.

One object of this invention is to provide heterocyclic compounds and salts thereof which possess activities as bradykinin antagonists.

Another object of this invention is to provide processes for the preparation of said heterocyclic compounds and salts thereof.

A further object of this invention is to provide a pharmaceutical composition comprising, as an active ingredient, said heterocyclic compounds and salts thereof.

Still further object of this invention is to provide an agent for the prevention and/or the treatment of bradykinin or its analogues mediated diseases such as allergy, inflammation, autoimmune disease, shock, pain, or the like, comprising said heterocyclic compounds and salts thereof as an active ingredient.

BACKGROUND ART

Heterocyclic compounds having activities as bradykinin antagonists have been known as described in EP-A-596,406 and EP-A-622,361.

DISCLOSURE OF THE INVENTION

The object heterocyclic compounds of this invention are new and can be represented by the following general formula

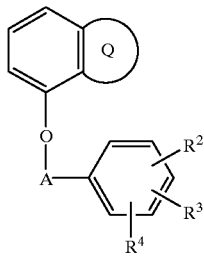

[I]

wherein a group of the formula:

is a group of the formula:

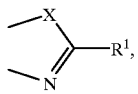

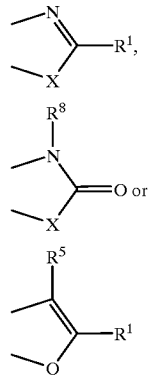

X is O, S or N—$R^5$, $R^1$ is lower alkyl, halo(lower)alkyl, lower alkylamino(lower) alkyl, hydroxy(lower) alkyl, lower alkoxy(lower)alkyl, lower alkoxy, lower alkylthio, lower alkylamino, acyl(lower)alkyl, acyl, hydroxy, mercapto, aryl or ar(lower)alkyl, and $R^5$ is hydrogen, lower alkyl, halo(lower)alkyl, lower alkylamino(lower)alkyl, hydroxy(lower)alkyl, lower alkoxy(lower)alkyl, lower alkoxy, lower alkylthio, lower alkylamino, acyl(lower)alkyl, acyl, aryl or ar(lower)alkyl, or $R^1$ and $R^5$ are taken together to form lower alkylene optionally having O, S or N or lower alkenylene optopnally having O, S or N, $R^2$ is hydrogen, halogen, lower alkyl or lower alkoxy, $R^3$ is halogen, lower alkyl or lower alkoxy, $R^4$ is amino optionally having suitable substituent(s), $R^8$ is lower alkyl or acyl(lower)alkyl, and A is lower alkylene.

The object compound [I] or its salt can be prepared by processes as illustrated in the following reaction schemes.

Process 1

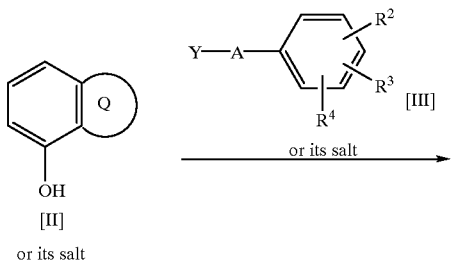

[II]
or its salt

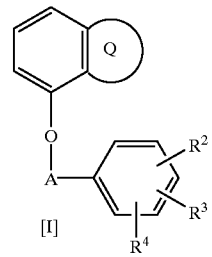

[I]

or its salt

Process 2

[Ia] or its salt →(Acylation)→ [Ib] or its salt

Process 3

[IV] or its salt + (R$_a^1$)$_4$C [V] → [Ic] or its salt wherein
R$_a^1$ is lower alkoxy,
R$^6$ is hydrogen or lower alkyl,
Ra$^7$ is acyl having amino,
R$_b^7$ is acyl having acylamino,
Y is a leaving group, and
a group of the formula:

$\bigcirc$ Q,

R$^2$, R$^3$, R$^4$, R$^5$ and A are each as defined above.

In the above and subsequent description of the present specification and claims, suitable examples of the various definitions to be included within the scope of the invention are explained in detail in the following.

The term "lower" is intended to mean a group having 1 to 6 carbon atom(s), unless otherwise provided.

In this respect, the term "lower" in lower alkenyl moiety, lower alkynyl moiety, heterocyclic(lower)alkenyl moiety and ar(lower)alkenyl moiety in the various definitions is intended to mean a group having 2 to 6 carbon atoms.

Further, the term "lower" in lower alkenoyl moiety, lower alkynoyl moiety, cyclo(lower)alkyl moiety, cyclo(lower) alkenyl moiety, ar(lower)alkenoyl moiety, ar(lower) alkynoyl moiety and heterocyclic(lower)alkenoyl moiety in the various definitions is intended to mean a group having 3 to 6 carbon atoms.

Suitable "halogen" may be fluorine, chlorine, bromine and iodine.

Suitable "aryl" and aryl moiety in the term "ar(lower) alkenoyl" may be phenyl, naphthyl, phenyl substituted with lower alkyl [e.g. tolyl, xylyl, mesityl, cumenyl, di(tert-butyl) phenyl, etc.] and the like, in which preferable one is phenyl, naphthyl and tolyl.

Suitable "lower alkyl" and lower alkyl moiety in the terms "acyl(lower)alkyl", "lower alkylamino(lower)alkyl", "hydroxy(lower)alkyl", "lower alkoxy(lower)alkyl", "heterocyclic(lower)alkyl", "lower alkylthio" and "lower alkylamino" may be straight or branched one such as methyl, ethyl, propyl, isopropyl, butyl, isobutyl, tert-butyl, pentyl, hexyl or the like, in which preferable one is $C_1$–$C_4$ alkyl such as methyl, ethyl, propyl, isobutyl or tert-butyl.

Suitable "lower alkoxy" and lower alkoxy moiety in the term "lower alkoxy(lower)alkyl" may be straight or branched one such as methoxy, ethoxy, propoxy, isopropoxy, butoxy, isobutoxy, tert-butoxy, pentyloxy, hexyloxy or the like, in which preferable one is $C_1$–$C_4$ alkoxy such as methoxy, ethoxy or isopropoxy.

Suitable "lower alkylene" may be a straight or branched one such as methylene, ethylene, trimethylene, methylmethylene, tetramethylene, ethylethylene, propylene, pentamethylene, hexamethylene or the like, in which the most preferable one is methylene.

Suitable "lower alkenylene" may be a straight or branched $C_2$–$C_6$ alkenylene such as vinylene, methylvinylene, propenylene, 1,3-butadienylene, pentenylene or the like.

Suitable "halo(lower)alkyl" may be chloromethyl, dichloromethyl, bromomethyl, fluoromethyl, trifluoromethyl, pentafluoroethyl, trifluoroethyl or the like.

Suitable "ar(lower)alkyl" may be benzyl, phenethyl, phenylpropyl, naphthylmethyl or the like, in which the most preferable one is benzyl.

Suitable "heterocyclic group" and all heterocyclic moieties in the various definitions mentioned in this specification and claims such as in the term "heterocyclic(lower) alkyl", "heterocyclic(lower)alkenyl", "heterocyclic(lower) alkenoyl", etc., may include saturated or unsaturated, monocyclic or polycyclic one containing at least one hetero atom such as oxygen atom, sulfur atom and/or nitrogen atom, preferably N, O and/or S containing heterocyclic group, in which preferable ones may be morpholinyl, piperazinyl, pyridyl, tetrahydropyridyl, pyrimidinyl, piperidyl, thienyl, furyl, oxazolyl, isoxazolyl, thiazolyl, tetrazolyl, imidazolyl, pyrrolidinyl, pyrrolyl, quinolyl, tetrahydroquinolyl, isoquinolyl or the like.

Suitable "acyl" and acyl moiety in the term "acyl(lower) alkyl" may be substituted or unsubstituted alkanoyl such as alkanoyl [e.g. formyl, acetyl, propionyl, butyryl, isobutyryl, valeryl, isovaleryl, pivaloyl, hexanoyl, heptanoyl, 3,3-dimethylbutyryl, etc.], halo(lower)alkanoyl [e.g. chloroacetyl, trifluoroacetyl, bromoacetyl, bromobutyryl, heptafluorobutyryl, etc.], hydroxy(lower)alkanoyl [e.g. glycoloyl, lactoyl, 3-hydroxypropionyl, glyceroyl, etc.], lower alkylsulfonyloxy(lower)alkanoyl [e.g. mesyloxyacetyl, ethylsulfonyloxyacetyl, mesyloxypropionyl, etc.], lower alkoxy(lower)alkanoyl [e.g. methoxyacetyl, ethoxyacetyl, methoxypropionyl, ethoxypropionyl, propoxypropionyl, methoxybutyryl, etc.], lower alkylthio(lower)alkanoyl [e.g. methylthioacetyl, ethylthioacetyl, methylthiopropionyl, ethylthiopropionyl, propylthiopropionyl, methylthiobutyryl, etc.], lower alkanoyloxy(lower)alkanoyl [e.g. acetyloxyacetyl, acetyloxypropionyl, propionyloxyacetyl, etc.], aryloxy (lower)alkanoyl [e.g. phenyloxyacetyl, phenyloxypropionyl, tolyloxyacetyl, naphthyloxyacetyl, etc.], aroyl(lower) alkanoyl [e.g. phenyloxalyl, benzoylacetyl, benzoylpropionyl, etc.], carboxy(lower)alkanoyl [e.g. oxalo, carboxyacetyl, 3-carboxypropionyl, 3-carboxybutyryl, 4-carboxybutyryl, 4-carboxyvaleryl, etc.], esterified carboxy (lower)alkanoyl, for example, lower alkoxycarbonyl(lower) alkanoyl [e.g. methoxycarbonylacetyl, ethoxycarbonylacetyl, methoxycarbonylpropionyl, ethoxycarbonylpropionyl, etc.], carbamoyl(lower)alkanoyl [e.g. carbamoylacetyl, carbamoylpropionyl, etc.], lower alkylcarbamoyl(lower)alkanoyl [e.g. methylcarbamoylacetyl, methylcarbamoylpropionyl, ethylcarbamoylpropionyl, dimethylcarbamoylpropionyl, (N-methyl-N-ethylcarbamoyl)propionyl, etc.], ar(lower) alkanoyl [e.g. phenylacetyl, tolylacetyl, naphthylacetyl, 2-phenylpropionyl, 3-phenylpropionyl, 4-phenylbutyryl, tritylcarbonyl, etc.], optionally substituted heterocyclic (lower)alkanoyl [e.g. morpholinoacetyl, thiomorpholinoacetyl, morpholinopropionyl, thiomorpholinopropionyl, piperidinopropionyl, piperazinylpropionyl, pyridylacetyl, pyrrolidinylpropionyl, imidazolidinylpropionyl, piperidinoacetyl, pyrrolidinylacetyl, hexamethyleneiminoacetyl, hexamethyleneiminopropionyl, imidazolylacetyl, furylacetyl, thienylacetyl, methylpiperazinylacetyl, pyridylpiperazinylacetyl, etc.], heterocyclicthio(lower) alkanoyl [e.g. pyridylthioacetyl, pyrimidinylthioacetyl, imidazolylthiopropionyl, etc.], etc., lower alkenoyl [e.g. acryloyl, crotonoyl, isocrotonoyl, 3-butenoyl, 3-pentenoyl, 4-pentenoyl, methacryloyl, etc.], lower alkynoyl [e.g. propioloyl, 2-butynoyl, 3-butynoyl, etc.], cyclo(lower) alkylcarbonyl [e.g. cyclopropylcarbonyl, cyclobutylcarbonyl, cyclopentylcarbonyl, cyclohexylcarbonyl, etc.], cyclo(lower)alkenylcarbonyl [e.g. cyclopentenylcarbonyl, cyclohexenylcarbonyl, etc.], carboxy, esterified carboxy such as lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], aryloxycarbonyl [e.g. phenoxycarbonyl, etc.], etc., substituted or unsubstituted aroyl such as aroyl [e.g. benzoyl, toluoyl, xyloyl, naphthoyl, etc.], lower alkoxyaroyl [e.g. methoxybenzoyl, etc.], haloaroyl [e.g. chlorobenzoyl, fluorobenzoyl, etc.], acylaroyl, for example, lower alkoxycarbonylaroyl [e.g. methoxycarbonylbenzoyl, etc.], etc., substituted or unsubstituted ar(lower)alkenoyl, in which said aryl group may be substituted with the above-mentioned lower alkyl or lower alkoxy, such as ar(lower)alkenoyl [e.g. cinnamoyl, allocinnamoyl, α-methylcinnamoyl, 4-methylcinnamoyl, etc.], lower alkoxy-ar(lower)alkenoyl [e.g. methoxycinnamoyl, ethoxycinnamoyl, dimethoxycinnamoyl, etc.], lower alkylenedioxy-ar(lower) alkenoyl [e.g. methylenedioxycinnamoyl, ethylenedioxycinnamoyl, etc.], nitro-ar(lower)alkenoyl [e.g. nitrocinnamoyl, etc.], cyano-ar(lower)alkenoyl [e.g. cyanocinnamoyl, etc.], halo-ar(lower)alkenoyl [e.g. chlorocinnamoyl, fluorocinnamoyl, etc.], hydroxy-ar(lower) alkenoyl [e.g. hydroxycinnamoyl, etc.], hydroxy(lower) alkoxy-ar(lower)alkenoyl [e.g. hydroxymethoxycinnamoyl, hydroxyethoxycinnamoyl, etc.], amino(lower)alkoxy-ar (lower)alkenoyl [e.g. aminoethoxycinnamoyl, etc.], lower alkylamino(lower)alkoxy-ar(lower)alkenoyl [e.g. methylaminomethoxycinnamoyl, dimethylaminomethoxycinnamoyl, etc.], heterocyclic (lower)alkoxy-ar(lower)alkenoyl [e.g. pyridylmethoxycinnamoyl, etc.], optionally substituted heterocyclic-ar(lower)alkenoyl [e.g. morpholinocinnamoyl, methylpiperazinylcinnamoyl, pyrrolidinylcinnamoyl, oxopyrrolidinylcinnamoyl, oxopiperidinocinnamoyl, dioxopyrrolidinylcinnamoyl, oxooxazolidinylcinnamoyl, pyrrolylcinnamoyl, tetrazolylcinnamoyl, etc.], heterocyclic (lower)alkyl-ar(lower)alkenoyl [e.g. pyridylmethylcinnamoyl, pyridylethylcinnamoyl, quinolylethylcinnamoyl, etc.], heterocyclic(lower)alkenylar (lower)alkenoyl [e.g. pyridylvinylcinnamoyl, quinolylvinylcinnamoyl, etc.], amino-ar(lower)alkenoyl [e.g. aminocinnamoyl, etc.], lower alkylamino-ar(lower) alkenoyl [e.g. methylaminocinnamoyl, dimethylaminocinnamoyl, etc.], acylamino-ar(lower) alkenoyl, for example, lower alkanoylamino-ar(lower) alkenoyl [e.g. acetylaminocinnamoyl, propionylaminocinnamoyl, isobutyrylaminocinnamoyl, etc.], cycloalkyl(lower)alkanoylamino-ar(lower)alkenoyl [e.g. cyclopentylacetylaminocinnamoyl, cyclohexylacetylaminocinnamoyl, adamantylacetylaminocinnamoyl, etc.], cycloalkylcarbonylamino-ar(lower)alkenoyl [e.g. cyclopropylcarbonylaminocinnamoyl, cyclopentylcarbonylaminocinnamoyl, cyclohexylcarbonylaminocinnamoyl, adamantylcarbonylaminocinnamoyl, etc.], lower alkenoylamino-ar(lower)alkenoyl [e.g. acryloylaminocinnamoyl, crotonoylaminocinnamoyl, etc.], lower alkoxycarbonylamino-ar (lower)alkenoyl [e.g. methoxycarbonylaminocinnamoyl, ethoxycarbonylaminocinnamoyl, etc.], hydroxy(lower) alkanoylamino-ar(lower)alkenoyl [e.g. hydroxyacetylaminocinnamoyl, hydroxypropionylaminocinnamoyl, etc.], lower alkoxy (lower)alkanoylamino-ar(lower)alkenoyl [e.g. methoxyacetylaminocinnamoyl, methoxypropionylaminocinnamoyl, etc.], halo(lower) alkanoylamino-ar(lower)alkenoyl [e.g. chloroacetylaminocinnamoyl, bromobutyrylaminocinnamoyl, trifluoroacetylaminocinnamoyl, etc.], amino(lower) alkanoylamino-ar(lower)alkenoyl [e.g. aminoacetylaminocinnamoyl, aminopropionylaminocinnamoyl, etc.], lower alkylamino (lower)alkanoylamino-ar(lower)-alkenoyl [e.g. methylaminoacetylaminocinnamoyl, dimethylaminoacetylaminocinnamoyl, etc.], lower alkanoylamino(lower)alkanoylamino-ar(lower)alkenoyl [e.g. acetylaminoacetylaminocinnamoyl, acetylaminopropionylaminocinnamoyl, etc.], carboxy (lower)alkanoylamino-ar(lower)alkenoyl [e.g. carboxyacetylaminocinnamoyl, carboxypropionylaminocinnamoyl, etc.], lower alkoxycarbonyl(lower)alkanoylamino-ar(lower)alkenoyl [e.g. ethoxycarbonylacetylaminocinnamoyl, ethoxycarbonylpropionylaminocinnamoyl, etc.], lower alkoxycarbonyl(lower)alkenoylamino-ar(lower)alkenoyl [e.g. ethoxycarbonylacryloylaminocinnamoyl, etc.], halo (lower)alkoxycarbonylamino-ar(lower)alkenoyl [e.g. chloroethoxycarbonylaminocinnamoyl, etc.], optionally substituted heterocyclic(lower)alkanoylamino-ar(lower)alkenoyl [e.g. pyridylacetylaminocinnamoyl, thienylacetylaminocinnamoyl, methylpyrrolylacetylaminocinnamoyl, etc.], aroylamino-ar (lower)alkenoyl [e.g. benzoylaminocinnamoyl, etc.], optionally substituted heterocycliccarbonylamino-ar(lower) alkenoyl [e.g. pyridylcarbonylaminocinnamoyl, morpholinocarbonylaminocinnamoyl, furylcarbonylaminocinnamoyl, thienylcarbonylaminocinnamoyl, oxazolylcarbonylaminocinnamoyl, methyloxazolylcarbonylaminocinnamoyl, dimethylisoxazolylcarbonylaminocinnamoyl, imidazolylcarbonylaminocinnamoyl, methylimidazolylcarbonylaminocinnamoyl, piperidylcarbonylaminocinnamoyl, ethylpiperidylcarbonylaminocinnamoyl, acetylpiperidylcarbonylaminocinnamoyl, pyrrolidinylcarbonylaminocinnamoyl, acetylpyrrolidinylcarbonylaminocinnamoyl, tert-butoxycarbonylpyrrolidinylcarbonylaminocinnamoyl, etc.], lower alkylsulfonylamino-ar(lower)alkenoyl [e.g. mesylaminocinnamoyl, ethylsulfonylaminocinnamoyl, etc.], etc., N-(lower alkanoyl)-N-(lower alkyl)amino-ar (lower)alkenoyl [e.g. N-acetyl-N-methylaminocinnamoyl, N-acetyl-N-ethylaminocinnamoyl, N-propionyl-N-methylaminocinnamoyl, etc.], N-[lower alkoxy(lower)-alkanoyl]-N-(lower alkyl)amino-ar(lower)alkenoyl [e.g. N-methoxyacetyl-N-methylaminocinnamoyl, N-methoxypropionyl-N-methylaminocinnamoyl, etc.], N-(lower alkanoyl)-N-[heterocyclic(lower)alkyl]amino-ar (lower)alkenoyl [e.g. N-acetyl-N-pyridylmethylaminocinnamoyl, etc.], N-(lower alkanoyl)-N-[lower alkoxy(lower)alkyl]amino-ar(lower)alkenoyl [e.g. N-acetyl-N-methoxyethylaminocinnamoyl, N-acetyl-N-methoxymethylaminocinnamoyl, N-propionyl-N-methoxyethylaminocinnamoyl, etc.], N-(lower alkanoyl)-N-[lower alkoxycarbonyl(lower)alkyl]-amino-ar(lower) alkenoyl [e.g. N-acetyl-N-tert-butoxycarbonylmethylaminocinnamoyl, N-acetyl-N-tert-butoxycarbonylethylaminocinnamoyl, N-propionyl-N-tert-butoxycarbonylmethylaminocinnamoyl, etc.], N-(lower alkanoyl)-N-[carboxy(lower)alkyl]amino-ar(lower)alkenoyl [e.g. N-acetyl-N-carboxymethylaminocinnamoyl, N-acetyl-N-carboxyethylaminocinnamoyl, N-propionyl-N-carboxymethylaminocinnamoyl, etc.], N-[lower alkoxy (lower)alkanoyl]-N-[heterocyclic(lower)alkyl]amino-ar (lower)alkenoyl [e.g. N-methoxyacetyl-N-pyridylmethylaminocinnamoyl, N-methoxypropionyl-N-pyridylmethylaminocinnamoyl, etc.], N-[heterocycliccarbonyl]-N-[lower alkoxy(lower)alkyl] amino-ar(lower)alkenoyl [e.g. N-pyridylcarbonyl-N-methoxymethylaminocinnamoyl, N-pyridylcarbonyl-N-methoxyethylaminocinnamoyl, N-thienylcarbonyl-N-methoxyethylaminocinnamoyl, etc.], ureido-ar(lower) alkenoyl [e.g. ureidocinnamoyl, etc.], lower alkylureido-ar (lower)alkenoyl [e.g. methylureidocinnamoyl, ethylureidocinnamoyl, dimethylureidocinnamoyl, etc.], heterocyclicureido-ar(lower)alkenoyl [e.g. pyridylureidocinnamoyl, pyrimidinylureidocinnamoyl, thienylureidocinnamoyl, etc.], acyl-ar(lower)alkenoyl, for example, lower alkanoyl-ar(lower)alkenoyl [e.g. formylcinnamoyl, acetylcinnamoyl, propionylcinnamoyl, etc.], carboxy-ar(lower)alkenoyl [e.g. carboxycinnamoyl, etc.], lower alkoxycarbonyl-ar(lower)alkenoyl [e.g. methoxycarbonylcinnamoyl, ethoxycarbonylcinnamoyl, etc.], carbamoyl-ar(lower)alkenoyl [e.g. carbamoylcinnamoyl, etc.], lower alkylcarbamoyl-ar(lower) alkenoyl [e.g. methylcarbamoylcinnamoyl, ethylcarbamoylcinnamoyl, dimethylcarbamoylcinnamoyl, propylcarbamoylcinnamoyl, isopropylcarbamoylcinnamoyl, diethylcarbamoylcinnamoyl, N-methyl-N-ethylcarbamoylcinnamoyl, etc.], hydroxy(lower) alkylcarbamoyl-ar(lower)alkenoyl [e.g. hydroxyethylcarbamoylcinnamoyl, bis(hydroxyethyl) carbamoylcinnamoyl, etc.], N-[hydroxy(lower)alkyl]-N-(lower alkyl)carbamoyl-ar(lower)alkenoyl [e.g. N-hydroxyethyl-N-methylcarbamoylcinnamoyl, etc.], lower alkoxy(lower)alkylcarbamoyl-ar(lower)alkenoyl [e.g. methoxymethylcarbamoylcinnamoyl, methoxyethylcarbamoylcinnamoyl, bis(methoxyethyl) carbamoylcinnamoyl, ethoxyethylcarbamoylcinnamoyl, methoxypropylcarbamoylcinnamoyl, bis(ethoxyethyl) carbamoylcinnamoyl, etc.], N-[lower alkoxy(lower)alkyl]-N-(lower alkyl)carbamoyl-ar(lower)alkenoyl [e.g. N-methoxyethyl-N-methylcarbamoylcinnamoyl, N-ethoxyethyl-N-methylcarbamoylcinnamoyl, etc.], heterocyclic(lower)alkylcarbamoyl-ar(lower)alkenoyl [e.g. pyridylmethylcarbamoylcinnamoyl, furylmethylcarbamoylcinnamoyl, thienylmethylcarbamoylcinnamoyl, etc.], N-[heterocyclic (lower)alkyl]-N-(lower alkyl) carbamoyl-ar (lower)alkenoyl [e.g. N-pyridylmethyl-N-methylcarbamoylcinnamoyl, etc.], heterocycliccarbamoyl-ar(lower)alkenoyl [e.g. morpholinylcarbamoylcinnamoyl, thienylcarbamoylcinnamoyl, pyridylcarbamoylcinnamoyl, pyrimidinylcarbamoylcinnamoyl, tetrazolylcarbamoylcinnamoyl, etc.], optionally substituted heterocycliccarbonyl-ar(lower)alkenoyl [e.g. morpholinocarbonylcinnamoyl, pyrrolidinylcarbonylcinnamoyl, piperidinocarbonylcinnamoyl, tetrahydropyridylcarbonylcinnamoyl, methylpiperazinylcarbonylcinnamoyl, etc.], lower alkenylcarbamoyl-ar(lower)alkenoyl [e.g. vinylcarbamoylcinnamoyl, allylcarbamoylcinnamoyl, methylpropenylcarbamoylcinnamoyl, etc.], lower alkynylcarbamoyl-ar(lower)alkenoyl [e.g. ethynylcarbamoylcinnamoyl, propynylcarbamoylcinnamoyl, etc.], amino(lower) alkylcarbamoyl-ar(lower)alkenoyl [e.g. aminomethylcarbamoylcinnamoyl, aminoethylcarbamoylcinnamoyl, etc.], lower alkylamino (lower)alkylcarbamoyl-ar(lower)alkenoyl [e.g. methylaminomethylcarbamoylcinnamoyl, methylaminoethylcarbamoylcinnamoyl, ethylaminoethylcarbamoylcinnamoyl, dimethylaminoethylcarbamoylcinnamoyl, etc.], lower alkylcarbamoyloxy(lower)alkylcarbamoyl-ar(lower) alkenoyl [e.g. methylcarbamoyloxymethylcarbamoylcinnamoyl, methylcarbamoyloxyethylcarbamoylcinnamoyl, ethylcarbamoyloxyethylcarbamoylcinnamoyl, dimethylcarbamoyloxyethylcarbamoylcinnamoyl, etc.], lower alkylcarbamoyl(lower)alkylcarbamoyl-ar(lower) alkenoyl [e.g. methylcarbamoylmethylcarbamoylcinnamoyl, methylcarbamoylethylcarbamoylcinnamoyl, ethylcarbamoylethylcarbamoylcinnamoyl, dimethylcarbamoylethylcarbamoylcinnamoyl, etc.], lower alkoxycarbonyl(lower)alkylcarbamoyl-ar(lower)alkenoyl [e.g. methoxycarbonylmethylcarbamoylcinnamoyl, methoxycarbonylethylcarbamoylcinnamoyl, ethoxycarbonylmethylcarbamoylcinnamoyl, ethoxycarbonylethylcarbamoylcinnamoyl, etc.], carboxy (lower)alkylcarbamoyl-ar(lower)alkenoyl [e.g. carboxymethylcarbamoylcinnamoyl, carboxyethylcarbamoylcinnamoyl, etc.], [lower alkylcarbamoyl-ar(lower)alkyl]carbamoyl-ar(lower) alkenoyl [e.g. (methylcarbamoyl-phenethyl) carbamoylcinnamoyl, (ethylcarbamoyl-phenethyl) carbamoylcinnamoyl, etc.], [lower alkoxycarbonyl-ar (lower)alkyl]carbamoyl-ar(lower)alkenoyl [e.g. (methoxycarbonyl-phenethyl)-carbamoylcinnamoyl, (ethoxycarbonyl-phenethyl)-carbamoylcinnamoyl, etc.], [carboxy-ar(lower)alkyl]carbamoyl-ar(lower)alkenoyl [e.g. carboxy-phenethyl)carbamoylcinnamoyl, etc.], N-[lower alkylcarbamoyl(lower)alkyl]-N-(lower alkyl)carbamoyl-ar (lower)alkenoyl [e.g. N-(methylcarbamoylmethyl)-N-methylcarbamoylcinnamoyl, N-(methylcarbamoylethyl)-N-methylcarbamoylcinnamoyl, N-(ethylcarbamoylethyl)-N-methylcarbamoylcinnamoyl, N-(dimethylcarbamoylethyl)-N-methylcarbamoylcinnamoyl, etc.], N-[lower alkoxycarbonyl(lower)alkyl]-N-(lower alkyl)carbamoyl-ar (lower)alkenoyl [e.g. N-methoxycarbonylmethyl-N-methylcarbamoylcinnamoyl, N-methoxycarbonylethyl-N-methylcarbamoylcinnamoyl, N-ethoxycarbonylmethyl-N-methylcarbamoylcinnamoyl, N-ethoxycarbonylethyl-N-methylcarbamoylcinnamoyl, etc.], N-[carboxy(lower)alkyl]-N-(lower alkyl)carbamoyl-ar(lower)alkenoyl [e.g. N-carboxymethyl-N-methylcarbamoylcinnamoyl, N-carboxyethyl-N-methylcarbamoylcinnamoyl, etc.], arylcarbamoyl-ar(lower)alkenoyl [e.g. phenylcarbamoylcinnamoyl, naphthylcarbamoylcinnamoyl, etc.], etc., etc., ar(lower)alkynoyl [e.g. phenylpropioloyl, etc.], substituted or unsubstituted heterocyclic(lower)alkenoyl, in which said heterocyclic group may be substituted with the above-mentioned lower alkyl or lower alkoxy, such as heterocyclic(lower)alkenoyl [e.g. morpholinylacryloyl, pyridylacryloyl, thienylacryloyl, etc.], heterocyclic(lower)alkyl-heterocyclic(lower)alkenoyl [e.g. pyridylmethylpyridylacryloyl, pyridylethylpyridylacryloyl, quinolylethylpyridylacryloyl, etc.], heterocyclic(lower) alkenyl-heterocyclic(lower)alkenoyl [e.g. pyridylvinylpyridylacryloyl, quinolylvinylpyridylacryloyl, etc.], amino-heterocyclic(lower)alkenoyl [e.g. aminopyridylacryloyl, etc.], lower alkylamino-heterocyclic (lower)alkenoyl [e.g. methylaminopyridylacryloyl, dimethylaminopyridylacryloyl, etc.], acylamino-heterocyclic(lower)alkenoyl, for example, lower alkanoylamino-heterocyclic(lower)alkenoyl [e.g. acetylaminopyridylacryloyl, propionylaminopyridylacryloyl, etc.], lower alkenoylamino-heterocyclic(lower)alkenoyl [e.g. acryloylaminopyridylacryloyl, crotonoylaminopyridylacryloyl, etc.], heterocyclic(lower) alkanoylamino-heterocyclic(lower)-alkenoyl [e.g. pyridylacetylaminopyridylacryloyl, thienylacetylaminopyridylacryloyl, etc.], heterocycliccarbonylamino-heterocyclic(lower)alkenoyl which may be substituted with lower alkyl [e.g. pyridylcarbonylaminopyridylacryloyl, furylcarbonylaminopyridylacryloyl, methylpyridylcarbonylaminopyridylacryloyl, etc.], lower alkanoylamino(lower)alkanoylamino-heterocyclic(lower)-alkenoyl [e.g. acetylaminoacetylaminopyridylacryloyl, acetylaminopropionylaminopyridylacryloyl, etc.], lower alkoxycarbonyl(lower)alkanoylamino-heterocyclic(lower)-alkenoyl [e.g. ethoxycarbonylacetylaminopyridylacryloyl, ethoxycarbonylpropionylaminopyridylacryloyl, etc.], lower alkoxy(lower)alkanoylamino-heterocyclic(lower)alkenoyl [e.g. methoxyacetylaminopyridylacryloyl, methoxypropionyl-aminopyridylacryloyl, ethoxypropionylaminopyridylacryloyl, etc.], etc., lower alkylureido-heterocyclic(lower)alkenoyl [e.g. methylureidopyridylacryloyl, etc.], acyl-heterocyclic(lower) alkenoyl, for example, carboxyheterocyclic(lower)alkenoyl [e.g. carboxypyridylacryloyl, etc.], lower alkoxycarbonyl-heterocyclic(lower)alkenoyl [e.g. ethoxycarbonylpyridylacryloyl, etc.], lower alkanoyl-heterocyclic(lower)alkenoyl [e.g. acetylpyridylacryloyl, acetyltetrahydroquinolylacryloyl,etc.], lower alkylcarbamoyl-heterocyclic(lower)alkenoyl [e.g. methylcarbamoylpyridylacryloyl, ethylcarbamoylpyridylacryloyl, dimethylcarbamoylpyridylacryloyl, diethylcarbamoylpyridylacryloyl, isopropylcarbamoylpyridylacryloyl, N-ethyl-N-methylcarbamoylpyridylacryloyl, etc.], lower alkoxy(lower) alkylcarbamoyl-heterocyclic(lower)alkenoyl [e.g. methoxymethylcarbamoylpyridylacryloyl, methoxyethylcarbamoylpyridylacryloyl, methoxypropylcarbamoylpyridylacryloyl, ethoxyethylcarbamoylpyridylacryloyl, bis(methoxyethyl) carbamoylpyridylacryloyl, etc.], hydroxy(lower) alkylcarbamoyl-heterocyclic(lower)alkenoyl [e.g. hydroxymethylcarbamoylpyridylacryloyl, hydroxyethylcarbamoylpyridylacryloyl, bis(hydroxyethyl) carbamoylpyridylacryloyl, etc.], heterocycliccarbamoyl-heterocyclic(lower)alkenoyl [e.g. pyridylcarbamoylpyridylacryloyl, morpholinylcarbamoylpyridylacryloyl, thienylcarbamoylpyridylacryloyl, pyrimidinylcarbamoylpyridylacryloyl, etc.], heterocyclic (lower)alkylcarbamoyl-heterocyclic(lower)-alkenoyl [e.g. pyridylmethylcarbamoylpyridylacryloyl, furylmethylcarbamoylpyridylacryloyl, thienylmethylcarbamoylpyridylacryloyl, etc.], heterocycliccarbonyl-heterocyclic(lower)alkenoyl [e.g. morpholinocarbonylpyridylacryloyl, pyrrolidinylcarbonylpyridylacryloyl, piperidinocarbonylpyridylacryloyl, etc.], lower alkenylcarbamoyl-heterocyclic(lower)alkenoyl [e.g. vinylcarbamoylpyridylacryloyl, allylcarbamoylpyridylacryloyl, etc.], lower alkynylcarbamoyl-heterocyclic(lower)alkenoyl [e.g. ethynylcarbamoylpyridylacryloyl, propynylcarbamoylpyridylacryloyl, etc.], etc., etc., heterocycliccarbonyl which may be substituted with substituent [e.g. furoyl, thenoyl, nicotinoyl, isonicotinoyl, morpholinocarbonyl, piperidinocarbonyl, 4-methyl-1-piperazinylcarbonyl, 4-ethyl-1-piperazinylcarbonyl, dimethylaminopiperidinocarbonyl, 4-methylcarbamoyl-1-piperazinylcarbonyl, 1,2,3,6-tetrahydropyridylcarbonyl, pyrrolidinylcarbonyl, indolylcarbonyl, etc.], aryloxycarbonyl which may be substituted with nitro [e.g. phenyloxycarbonyl, nitrophenyloxycarbonyl, etc.], ar(lower)alkoxycarbonyl which may be substituted with nitro [e.g. benzyloxycarbonyl, nitrobenzyloxycarbonyl, etc.], substituted or unsubstituted carbamoyl or thiocarbamoyl such as carbamoyl, lower alkylcarbamoyl [e.g. methylcarbamoyl, ethylcarbamoyl, propylcarbamoyl, isopropylcarbamoyl, butylcarbamoyl, isobutylcarbamoyl, tert-butylcarbamoyl, pentylcarbamoyl, dimethylcarbamoyl, diethylcarbamoyl, N-ethyl-N-methylcarbamoyl, etc.], carboxy(lower)alkylcarbamoyl [e.g. carboxymethylcarbamoyl, carboxyethylcarbamoyl, etc.], esterified carboxy(lower)alkylcarbamoyl, for example, lower alkoxycarbonyl(lower)alkylcarbamoyl [e.g. methoxycarbonylmethylcarbamoyl, ethoxycarbonylmethylcarbamoyl, ethoxycarbonylethylcarbamoyl, etc.], lower alkenylcarbamoyl [e.g. vinylcarbamoyl, allylcarbamoyl, etc.], cyclo(lower) alkylcarbamoyl [e.g. cyclopropylcarbamoyl, cyclobutylcarbamoyl, cyclopentylcarbamoyl, cyclohexylcarbamoyl, etc.], halo(lower)alkanoylcarbamoyl [e.g. trichloroacetylcarbamoyl, etc.], substituted or unsubstituted arylcarbamoyl, for example, arylcarbamoyl [e.g. phenylcarbamoyl, tolylcarbamoyl, xylylcarbamoyl, naphthylcarbamoyl, ethylphenylcarbamoyl, etc.], arylthiocarbamoyl [e.g. phenylthiocarbamoyl, etc.], lower alkoxy-arylcarbamoyl [e.g. methoxyphenylcarbamoyl, etc.], haloarylcarbamoyl [e.g. fluorophenylcarbamoyl, chlorophenylcarbamoyl, etc.], halo(lower)alkyl-arylcarbamoyl [e.g. trifluoromethylphenylcarbamoyl, etc.], nitro-arylcarbamoyl [e.g. nitrophenylcarbamoyl, etc.], cyanoarylcarbamoyl [e.g. cyanophenylcarbamoyl, etc.], hydroxy(lower)alkyl-arylcarbamoyl [e.g. hydroxymethylphenylcarbamoyl, hydroxyethylphenylcarbamoyl, etc.], aminoarylcarbamoyl [e.g. aminophenylcarbamoyl, etc.], lower alkylaminoaryl-carbamoyl [e.g. methylaminophenylcarbamoyl, ethylaminophenylcarbamoyl, dimethylaminophenylcarbamoyl, etc.], lower alkanoylamino-arylcarbamoyl [e.g. acetylaminophenylcarbamoyl, propionylaminophenylcarbamoyl, etc.], N-(lower alkanoyl)-N-(lower alkyl)amino-arylcarbamoyl [e.g. N-acetyl-N-methylaminophenylcarbamoyl, N-propionyl-N-methylaminophenylcarbamoyl, etc.], lower alkoxy(lower)alkanoylamino-arylcarbamoyl [e.g. methoxyacetylaminophenylcarbamoyl, methoxypropionylaminophenylcarbamoyl, etc.], lower alkoxycarbonyl(lower)alkanoylamino-arylcarbamoyl [e.g. ethoxycarbonylacetylaminophenylcarbamoyl, methoxycarbonylpropionylaminophenylcarbamoyl, etc.], carboxyamino-arylcarbamoyl [e.g. carboxyaminophenylcarbamoyl, etc.], lower alkoxycarbonylamino-arylcarbamoyl [e.g. ethoxycarbonylaminophenylcarbamoyl, etc.], heterocycliccarbonylamino-arylcarbamoyl [e.g. pyridylcarbonylaminophenylcarbamoyl, furylcarbonylaminophenylcarbamoyl, morpholinocarbonylaminophenylcarbamoyl, etc.], heterocyclic(lower)alkanoylamino-arylcarbamoyl [e.g. pyridylacetylaminophenylcarbamoyl, thienylacetylaminophenylcarbamoyl, etc.], aroylaminoaryl-carbamoyl [e.g. benzoylaminophenylcarbamoyl, etc.], ureido-arylcarbamoyl [e.g. ureidophenylcarbamoyl, etc.], lower alkylureido-arylcarbamoyl [e.g. methylureidophenylcarbamoyl, ethylureidophenylcarbamoyl, etc.], hydroxyimino(lower)alkyl-arylcarbamoyl [e.g. hydroxyiminoethylphenylcarbamoyl, etc.], lower alkoxyimino(lower)alkyl-arylcarbamoyl [e.g. methoxyiminoethylphenylcarbamoyl, etc.], lower alkylhydrazono(lower)alkyl-arylcarbamoyl [e.g. methylhydrazonoethylphenylcarbamoyl, dimethylhydrazonoethylphenylcarbamoyl, etc.], optionally substituted heterocyclic-arylcarbamoyl [e.g. oxopyrrolidinylphenylcarbamoyl, oxopiperidinophenylcarbamoyl, dioxopyrrolidinylphenylcarbamoyl, oxooxazolidinylphenylcarbamoyl, pyrrolylphenylcarbamoyl, etc.], acyl-arylcarbamoyl, for example, carboxy-arylcarbamoyl [e.g. carboxyphenylcarbamoyl, etc.], lower alkoxycarbonyl-arylcarbamoyl [e.g. ethoxycarbonylphenylcarbamoyl, etc.], heterocycliccarbonyl-arylcarbamoyl [e.g. morpholinocarbonylphenylcarbamoyl, pyrrolidinylcarbonylphenylcarbamoyl, piperidinocarbonylphenylcarbamoyl, 1,2,3,6-tetrahydropyridylcarbonylphenylcarbamoyl, piperazinylcarbonylphenylcarbamoyl, thiomorpholinocarbonylphenylcarbamoyl, etc.], heterocycliccarbonyl-arylcarbamoyl substituted with lower alkyl [e.g. methylpiperazinylcarbonylphenylcarbamoyl, ethylpiperazinylcarbonylphenylcarbamoyl, etc.], heterocycliccarbonyl-arylcarbamoyl substituted with aryl [e.g. phenylpiperazinylcarbonylphenylcarbamoyl, etc.], heterocycliccarbonyl-arylcarbamoyl substituted with a heterocyclic group [e.g. pyridylpiperazinylcarbonyl-phenylcarbamoyl, etc.], heterocycliccarbonyl-arylcarbamoyl substituted with lower alkanoyl [e.g. acetylpiperazinyl-carbonylphenylcarbamoyl, etc.], heterocycliccarbonyl-arylcarbamoyl substituted with lower alkoxycarbonyl [e.g. ethoxycarbonylpiperazinylcarbonylphenylcarbamoyl, etc.], heterocycliccarbonyl-arylcarbamoyl substituted with lower alkylamino [e.g. methylaminopiperazinylcarbonyl-phenylcarbamoyl, dimethylaminopiperidinocarbonylphenyl-carbamoyl, etc.], heterocycliccarbonyl-arylcarbamoyl substituted with lower alkylcarbamoyl [e.g. methylcarbamoylpiperazinylcarbonylphenylcarbamoyl, etc.], carbamoyl-arylcarbamoyl [e.g. carbamoylphenylcarbamoyl, etc.], lower alkylcarbamoyl-arylcarbamoyl [e.g. methylcarbamoylphenylcarbamoyl, ethylcarbamoylphenyl-carbamoyl, propylcarbamoylphenylcarbamoyl, dimethylcarbamoylphenylcarbamoyl, diethylcarbamoylphenylcarbamoyl, N-ethyl-N-methylcarbamoylphenylcarbamoyl, N-isopropyl-N-methylcarbamoylphenylcarbamoyl, etc.], hydroxy (lower) alkylcarbamoyl-arylcarbamoyl [e.g. hydroxymethylcarbamoylphenylcarbamoyl, hydroxyethylcarbamoylphenylcarbamoyl, bis (hydroxyethyl)carbamoylphenylcarbamoyl, etc.], N-[hydroxy(lower)alkyl]-N-(lower alkyl)carbamoyl-arylcarbamoyl [e.g. N-(hydroxyethyl)-N-methylcarbamoylphenylcarbamoyl, etc.], lower alkoxy (lower)alkylcarbamoyl-arylcarbamoyl [e.g. methoxymethylcarbamoylphenylcarbamoyl, methoxyethylcarbamoylphenylcarbamoyl, ethoxyethylcarbamoylphenylcarbamoyl, bis(methoxyethyl) carbamoylphenylcarbamoyl, bis(ethoxyethyl) carbamoylphenylcarbamoyl, etc.], N-[lower alkoxy(lower) alkyl]-N-(lower alkyl)carbamoylarylcarbamoyl [e.g. N-(methoxyethyl)-N-methylcarbamoylphenylcarbamoyl, N-(methoxypropyl)-N-methylcarbamoylphenylcarbamoyl, etc.], lower alkylamino(lower)alkylcarbamoyl-arylcarbamoyl [e.g. methylaminoethylcarbamoylphenylcarbamoyl, dimethylaminoethylcarbamoylphenylcarbamoyl, etc.], N-[lower alkylamino(lower)alkyl]-N-(lower alkyl) carbamoyl-arylcarbamoyl [e.g. N-(dimethylaminoethyl)-N-methyl-carbamoylphenylcarbamoyl, N-(dimethylaminopropyl)-N-methylcarbamoylphenylcarbamoyl, etc.], heterocycliccarbamoylarylcarbamoyl-arylcarbamoyl [e.g. morpholinylcarbamoylphenylcarbamoyl, thienylcarbamoylphenylcarbamoyl, pyridylcarbamoylphenylcarbamoyl, pyrimidinylcarbamoylphenylcarbamoyl, etc.], N-(heterocyclic)-N-(lower alkyl)carbamoyl-arylcarbamoyl [e.g. N-pyridyl-N-methylcarbamoylphenylcarbamoyl, etc.], heterocyclic(lower)alkylcarbamoyl-arylcarbamoyl [e.g. pyridylmethylcarbamoylphenylcarbamoyl, pyridylethylcarbamoylphenylcarbamoyl, thienylmethylcarbamoylphenylcarbamoyl, etc.], N-[heterocyclic(lower)alkyl]-N-(lower alkyl)carbamoyl-arylcarbamoyl [e.g. N-pyridylmethyl-N-methylcarbamoylphenylcarbamoyl, etc.], N-[heterocyclic (lower alkyl]-N-[lower alkoxy(lower)alkyl]-carbamoyl-arylcarbamoyl [e.g. N-pyridylmethyl-N- methoxyethylcarbamoylphenylcarbamoyl, etc.] arylcarbamoyl-arylcarbamoyl [e.g. phenylcarbamoylphenylcarbamoyl, etc.], lower alkylamino-arylcarbamoyl-arylcarbamoyl [e.g. dimethylaminophenylcarbamoylphenylcarbamoyl, etc.], lower alkanoyl-arylcarbamoyl [e.g. acetylphenylcarbamoyl, propionylphenylcarbamoyl, etc.], etc., etc., ar(lower) alkylcarbamoyl [e.g. benzylcarbamoyl, phenethylcarbamoyl, etc.], heterocycliccarbamoyl [e.g. furylcarbamoyl, thienylcarbamoyl, pyridylcarbamoyl, quinolylcarbamoyl, isoquinolylcarbamoyl, pyrimidinylcarbamoyl, pyrazolylcarbamoyl, etc.], heterocyclic(lower)alkylcarbamoyl [e.g. pyridylmethylcarbamoyl, pyridylethylcarbamoyl, furylmethylcarbamoyl, thienylmethylcarbamoyl, etc.], arylaminocarbamoyl [e.g. phenylaminocarbamoyl, etc.], aroylcarbamoyl [e.g. benzoylcarbamoyl, etc.], etc., lower alkylsulfonyl [e.g. mesyl, ethylsulfonyl, propylsulfonyl, isopropylsulfonyl, tert-butylsulfonyl, pentylsulfonyl, etc.], arylsulfonyl [e.g. tosyl, phenylsulfonyl, etc.], ar(lower) alkylsulfonyl [e.g. benzylsulfonyl, phenethylsulfonyl, etc.], ar(lower) alkenylsulfonyl [e.g. styrylsulfonyl, cinnamoylsulfonyl, etc.], phthaloyl, substituted or unsubstituted amino acid residue mentioned below, or the like.

Suitable "amino acid residue" may include natural or artificial ones, and such amino acid may be glycine, sarcosine, alanine, β-alanine, valine, norvaline, leucine, isoleucine, norleucine, serine, threonine, cysteine, methionine, phenylalanine, phenylglycine, tryptophan, tyrosine, proline, hydroxyproline, glutamic acid, aspartic acid, glutamine, asparagine, lysine, arginine, histidine, ornithine, or the like, in which more preferable one is glycine, sarcosine, alanine, β-alanine and proline, and the most preferable one is glycine. And said amino acid residue may be substituted with suitable substituent(s) such as the above-mentioned lower alkyl, the above-mentioned aryl, the above-mentioned acyl, ar(lower)alkyl [e.g. benzyl, phenethyl, trityl, etc.], cycloalkyl [e.g. cyclopropyl, cyclobutyl, cyclopentyl, cyclohexyl, cycloheptyl, cyclooctyl, adamantyl, etc.], a heterocyclic group mentioned above, heterocyclic(lower)alkyl [e.g. pyridylmethyl, pyridylethyl, imidazolylmethyl, furylmethyl, thienylmethyl, morpholinomethyl, piperidinomethyl, etc.], substituted or unsubstituted amidino [e.g. amidino, methylamidino, N-ethyl-N'-cyanoamidino, etc.], or the like.

Preferred example of said amino acid residue substituted with suitable substituent(s) may be amino acid residue substituted with lower alkyl [e.g. ethylglycyl, isopropylglycyl, dimethylglycyl, diethylglycyl, ethylsarcosyl, isopropylsarcosyl, methylalanyl, methyl-β-alanyl, dimethyl-β-alanyl, etc.], amino acid residue substituted with aryl [e.g. N-phenylglycyl, N-tolylglycyl, N-phenylalanyl, N-phenylsarcosyl, etc.], amino acid residue substituted with ar(lower)alkyl [e.g. benzylglycyl, tritylglycyl, phenethylglycyl, benzylsarcosyl, benzylalanyl, etc.], amino acid residue substituted with a heterocyclic group [e.g. morpholinoglycyl, piperidinoglycyl, pyridylglycyl, etc.], amino acid residue substituted with heterocyclic(lower)alkyl [e.g. pyridylmethylglycyl, imidazolylmethylglycyl, furylmethylglycyl, thienylmethylglycyl, etc.], amino acid residue substituted with cycloalkyl [e.g. cyclopropylglycyl, cyclobutylglycyl, cyclopentylglycyl, cyclohexylglycyl, cycloheptylglycyl, cyclooctylglycyl, adamantylglycyl, cyclohexylsarcosyl, cycloheptylsarcosyl, cyclohexylalanyl, etc.], amino acid residue substituted with optionally substituted amidino [e.g. amidinoglycyl, methylamidinoglycyl, N-ethyl-N'-cyanoamidinoglycyl, etc.], amino acid residue substituted with acyl such as amino acid residue substituted with alkanoyl [e.g. formylglycyl, acetylglycyl, acetylsarcosyl, acetylalanyl, acetyl-β-alanyl, propionylglycyl, butyrylglycyl, isobutyrylglycyl, valerylglycyl, isovalerylglycyl, pivaloylglycyl, hexanoylglycyl, heptanoylglycyl, etc.], amino acid residue substituted with halo(lower)alkanoyl [e.g. trifluoroacetylglycyl, trifluoroacetylsarcosyl, trifluoroacetylalanyl, bromoacetylglycyl, heptafluorobutyrylglycyl, etc.], amino acid residue substituted with hydroxy(lower)alkanoyl [e.g. glycoloylglycyl, glycoloylsarcosyl, lactoylglycyl, lactoylalanyl, etc.], amino acid residue substituted with lower alkylsulfonyloxy(lower)alkanoyl [e.g. mesyloxyacetylglycyl, ethylsulfonyloxyacetylglycyl, mesyloxyacetylsarcosyl, etc.], amino acid residue substituted with lower alkoxy(lower)alkanoyl [e.g. methoxyacetylglycyl, ethoxyacetylglycyl, methoxyacetylsarcosyl, methoxypropionylalanyl, etc.], amino acid residue substituted with aryloxy(lower)alkanoyl [e.g. phenyloxyacetylglycyl, phenyloxypropionylglycyl, phenyloxyacetylsarcosyl, etc.], amino acid residue substituted with lower alkylthio(lower)alkanoyl [e.g. methylthioacetylglycyl, methylthiopropionylglycyl, etc.], amino acid residue substituted with lower alkylcarbamoyl (lower)alkanoyl [e.g. methylcarbamoylpropionylglycyl, methylcarbamoylpropionylalanyl, etc.], amino acid residue substituted with lower alkanoyloxy(lower)alkanoyl [e.g. acetyloxyacetylglycyl, acetyloxyacetylsarcosyl, propionyloxyacetylglycyl, acetyloxypropionylalanyl, etc.], amino acid residue substituted with carboxy(lower)alkanoyl [e.g. carboxyacetylglycyl, carboxypropionylglycyl, carboxypropionylsarcosyl, carboxyacetylalanyl, etc.], amino acid residue substituted with lower alkoxycarbonyl (lower)alkanoyl [e.g. methoxycarbonylacetylglycyl, ethoxycarbonylpropionylglycyl, methoxycarbonylacetylsarcosyl, etc.], amino acid residue substituted with ar(lower)alkanoyl [e.g. phenylacetylglycyl, phenylacetylsarcosyl, phenylpropionylalanyl, phenylpropionylglycyl, naphthylacetylglycyl, phenylbutyrylglycyl, etc.], amino acid residue substituted with optionally substituted heterocyclic(lower)alkanoyl [e.g. morpholinoacetylglycyl, thiomorpholinoacetylglycyl, its oxide or dioxide, pyridylacetylglycyl, morpholinopropionylalanyl, imidazolylacetylglycyl, piperidinoacetylglycyl, pyrrolidinylacetylglycyl, hexamethyleneiminoacetylglycyl, methylpiperazinylacetylglycyl, pyridylpiperazinylacetylglycyl, etc.], amino acid residue substituted with lower alkenoyl [e.g. acryloylglycyl, crotonoylglycyl, 3-pentenoylglycyl, 3-butenoylglycyl, 4-pentenoylglycyl, 3-butenoylsarcosyl, etc.], amino acid residue substituted with substituted or unsubstituted ar(lower)alkenoyl, in which said aryl group may be substituted with the above-mentioned lower alkyl or lower alkoxy, such as amino acid residue substituted with ar(lower) alkenoyl [e.g. cinnamoylglycyl, allocinnamoylglycyl, α-methylcinnamoylglycyl, 4-methylcinnamoylglycyl, cinnamoylsarcosyl, etc.], amino acid residue substituted with lower alkoxy-ar(lower)alkenoyl [e.g. methoxycinnamoylglycyl, ethoxycinnamoylglycyl, dimethoxycinnamoylglycyl, etc.], amino acid residue substituted with lower alkylenedioxy-ar(lower)alkenoyl [e.g. methylenedioxycinnamoylglycyl, ethylenedioxycinnamoylglycyl, etc.], amino acid residue substituted with nitro-ar(lower)alkenoyl [e.g. nitrocinnamoylglycyl, etc.], amino acid residue substituted with cyano-ar(lower)alkenoyl [e.g. cyanocinnamoylglycyl, etc.], amino acid residue substituted with halo-ar(lower) alkenoyl [e.g. chlorocinnamoylglycyl, fluorocinnamoylglycyl, etc.], amino acid residue substituted with hydroxy-ar(lower)alkenoyl [e.g. hydroxycinnamoylglycyl, etc.], amino acid residue substituted with hydroxy(lower)alkoxy-ar(lower)alkenoyl [e.g. hydroxymethoxycinnamoylglycyl, hydroxyethoxycinnamoylglycyl, etc.], amino acid residue substituted with amino(lower)alkoxy-ar(lower)alkenoyl [e.g. aminoethoxycinnamoylglycyl, etc.], amino acid residue substituted with lower alkylamino(lower)alkoxy-ar(lower)alkenoyl [e.g. methylaminomethoxycinnamoylglycyl, dimethylaminoethoxycinnamoylglycyl, etc.], amino acid residue substituted with heterocyclic(lower)alkoxy-ar(lower)alkenoyl [e.g. pyridylmethoxycinnamoylglycyl, etc.], amino acid residue substituted with optionally substituted heterocyclic-ar(lower)alkenoyl [e.g. morpholinocinnamoylglycyl, methylpiperazinylcinnamoylglycyl, pyrrolidinylcinnamoylglycyl, oxopyrrolidinylcinnamoylglycyl, oxopiperidinocinnamoylglycyl, dioxopyrrolidinylcinnamoylglycyl, oxooxazolidinylcinnamoylglycyl, pyrrolylcinnamoylglycyl, tetrazolylcinnamoylglycyl, etc.], amino acid residue substituted with heterocyclic(lower)alkyl-ar(lower)alkenoyl [e.g. pyridylmethylcinnamoylglycyl, pyridylethylcinnamoylglycyl, quinolylethylcinnamoylglycyl, etc.], amino acid residue substituted with heterocyclic(lower)alkenyl-ar(lower)alkenoyl [e.g. pyridylvinylcinnamoylglycyl, quinolylvinylcinnamoylglycyl, etc.], amino acid residue substituted with amino-ar(lower)alkenoyl [e.g. aminocinnamoylglycyl, etc.], amino acid residue substituted with lower alkylamino-ar(lower)alkenoyl [e.g. methylaminocinnamoylglycyl, dimethylaminocinnamoylglycyl, etc.], amino acid residue substituted with acylamino-ar(lower)alkenoyl, for example, amino acid residue substituted with lower alkanoylamino-ar(lower)alkenoyl [e.g. acetylaminocinnamoylglycyl, propionylaminocinnamoylglycyl, isobutyrylaminocinnamoyl-glycyl, etc.], amino acid residue substituted with cycloalkyl(lower)alkanoylamino-ar(lower)alkenoyl [e.g. cyclopentylacetylaminocinnamoylglycyl, cyclohexylacetylaminocinnamoylglycyl, adamantylacetylaminocinnamoylglycyl, etc.], amino acid residue substituted with cycloalkylcarbonylamino-ar(lower)alkenoyl [e.g. cyclopropylcarbonylaminocinnamoylglycyl, cyclopentylcarbonylaminocinnamoylglycyl, cyclohexylcarbonylaminocinnamoylglycyl, adamantylcarbonylaminocinnamoylglycyl, etc.], amino acid residue substituted with lower alkenoylamino-ar(lower)alkenoyl [e.g. acryloylaminocinnamoylglycyl, crotonoylaminocinnamoylglycyl, etc.], amino acid residue substituted with lower alkoxycarbonylamino-ar(lower)-alkenoyl [e.g. methoxycarbonylaminocinnamoylglycyl, ethoxycarbonylaminocinnamoylglycyl, etc.], amino acid residue substituted with hydroxy(lower)alkanoylamino-ar(lower)alkenoyl [e.g. hydroxyacetylaminocinnamoylglycyl, hydroxypropionylaminocinnamoylglycyl, etc.], amino acid residue substituted with lower alkoxy(lower)alkanoylamino-ar(lower)alkenoyl [e.g. methoxyacetylaminocinnamoylglycyl, methoxypropionylaminocinnamoylglycyl, etc.], amino acid residue substituted with halo(lower)alkanoylamino-ar(lower)alkenoyl [e.g. chloroacetylaminocinnamoylglycyl, bromobutyrylaminocinnamoylglycyl, trifluoroacetylaminocinnamoylglycyl, etc.], amino acid residue substituted with amino(lower)alkanoylamino-ar(lower)alkenoyl [e.g. aminoacetylaminocinnamoylglycyl, aminopropionylaminocinnamoylglycyl, etc.], amino acid residue substituted with lower alkylamino(lower)alkanoylamino-ar(lower)alkenoyl [e.g. methylaminoacetylaminocinnamoylglycyl, dimethylaminoacetylaminocinnamoylglycyl, etc.], amino acid residue substituted with lower alkanoylamino(lower)alkanoylamino-ar(lower)alkenoyl [e.g. acetylaminoacetylaminocinnamoylglycyl, acetylaminopropionylaminocinnamoylglycyl, etc.], amino acid residue substituted with carboxy(lower)alkanoylamino-ar(lower)alkenoyl [e.g. carboxyacetylaminocinnamoylglycyl, carboxypropionylaminocinnamoylglycyl, etc.], amino acid residue substituted with lower alkoxycarbonyl(lower)alkanoylamino-ar(lower)alkenoyl [e.g. ethoxycarbonylacetylaminocinnamoylglycyl, ethoxycarbonylpropionylaminocinnamoylglycyl, etc.], amino acid residue substituted with lower alkoxycarbonyl(lower)alkenoylamino-ar(lower)alkenoyl [e.g. ethoxycarbonylacryloylaminocinnamoylglycyl, etc.], amino acid residue substituted with halo(lower)alkoxycarbonylamino-ar(lower)alkenoyl [e.g. chloroethoxycarbonylaminocinnamoylglycyl, etc.], amino acid residue substituted with optionally substituted heterocyclic(lower)alkanoylamino-ar(lower)alkenoyl [e.g. pyridylacetylaminocinnamoylglycyl, thienylacetylaminocinnamoylglycyl, methylpyrrolylacetylaminocinnamoylglycyl, etc.], amino acid residue substituted with aroylamino-ar(lower)alkenoyl [e.g. benzoylaminocinnamoylglycyl, etc.], amino acid residue substituted with optionally substituted heterocycliccarbonylamino-ar(lower)alkenoyl [e.g. pyridylcarbonylaminocinnamoylglycyl, morpholinocarbonylaminocinnamoylglycyl, furylcarbonylaminocinnamoylglycyl, thienylcarbonylaminocinnamoylglycyl, oxazolylcarbonylaminocinnamoylglycyl, methyloxazolylcarbonylaminocinnamoylglycyl, dimethylisoxazolylcarbonylaminocinnamoylglycyl, imidazolylcarbonylaminocinnamoylglycyl, methylimidazolylcarbonylaminocinnamoylglycyl, piperidylcarbonylaminocinnamoylglycyl, ethylpiperidylcarbonylaminocinnamoylglycyl, acetylpiperidylcarbonylaminocinnamoylglycyl, pyrrolidinylcarbonylaminocinnamoylglycyl, acetylpyrrolidinylcarbonylaminocinnamoylglycyl, tert-butoxycarbonylpyrrolidinylcarbonylaminocinnamoylglycyl, etc.], amino acid residue substituted with lower alkylsulfonylamino-ar(lower)alkenoyl [e.g. mesylaminocinnamoylglycyl, ethylsulfonylaminocinnamoylglycyl, etc.], etc., amino acid residue substituted with N-(lower alkanoyl)-N-(lower alkyl)amino-ar(lower)alkenoyl [e.g. N-acetyl-N-methylaminocinnamoylglycyl, N-acetyl-N-ethylaminocinnamoylglycyl, N-propionyl-N-methylaminocinnamoylglycyl, etc.], amino acid resieue substituted with N-[lower alkoxy(lower)alkanoyl]-N-(lower alkyl)amino-ar(lower)alkenoyl [e.g. N-methoxyacetyl-N-methylaminocinnamoylglycyl, N-methoxypropionyl-N-methylaminocinnamoylglycyl, etc.], amino acid residue substituted with N-(lower alkanoyl)-N-[heterocyclic(lower)alkyl]amino-ar(lower)alkenoyl [e.g. N-acetyl-N-pyridylmethylaminocinnamoylglycyl, etc.], amino acid residue substituted with N-(lower alkanoyl)-N-[lower alkoxy (lower)alkyl]amino-ar(lower)alkenoyl [e.g. N-acetyl-N-methoxyethylaminocinnamoylglycyl, N-acetyl-N-methoxymethylaminocinnamoylglycyl, N-propianyl-N-methoxyethylaminocinnamoylglycyl, etc.], amino acid residue substituted with N-(lower alkanoyl)-N-[lower alkoxycarbonyl(lower)alkyl]amino-ar(lower)alkenoyl [e.g. N-acetyl-N-tert-butoxycarbonylmethylaminocinnamoylglycyl, N-acetyl-N-tert-butoxycarbonylethylaminocinnamoylglycyl, N-propionyl-N-tert-butoxycarbonylmethylaminocinnamoylglycyl, etc.], amino acid residue substituted with N-(lower alkanoyl)-N-[carboxy(lower)alkyl]amino-ar(lower)-alkenoyl [e.g. N-acetyl-N-carboxymethylaminocinnamoylglycyl, N-acetyl-N-carboxyethylaminocinnamoylglycyl, N-propionyl-N-carboxymethylaminocinnamoylglycyl, etc.], amino acid residue substituted with N-[lower alkoxy(lower)alkanoyl]-N-[heterocyclic(lower)alkyl]amino-ar(lower)alkenoyl [e.g. N-methoxyacetyl-N-pyridylmethylaminocinnamoylglycyl, N-methoxypropionyl-N-pyridylmethylaminocinnamoylglycyl, etc.], amino acid residue substituted with N-[heterocycliccarbonyl]-N-[lower alkoxy(lower)alkyl]amino-ar(lower)alkenoyl [e.g. N-pyridylcarbonyl-N-methoxymethylaminocinnamoylglycyl, N-pyridylcarbonyl-N-methoxyethylaminocinnamoylglycyl, N-thienylcarbonyl-N-methoxyethylaminocinnamoylglycyl, etc.], amino acid residue substituted with ureido-ar(lower)alkenoyl [e.g. ureidocinnamoylglycyl, etc.], amino acid residue substituted with lower alkylureido-ar(lower)alkenoyl [e.g. methylureidocinnamoylglycyl, ethylureidocinnamoylglycyl, dimethylureidocinnamoylglycyl, etc.], amino acid residue substituted with heterocyclicureido-ar(lower)alkenoyl, [e.g. pyridylureidocinnamoylglycyl, pyrimidinylureidocinnamoylglycyl, thienylureidocinnamoylglycyl, etc.], amino acid residue substituted with acyl-ar(lower)alkenoyl, for example, amino acid residue substituted with lower alkanoyl-ar(lower) alkenoyl [e.g. formylcinnamoylglycyl, acetylcinnamoylglycyl, propionylcinnamoylglycyl, etc.], amino acid residue substituted with carboxy-ar(lower)-alkenoyl [e.g. carboxycinnamoylglycyl, etc.], amino acid residue substituted with lower alkoxycarbonyl-ar(lower) alkenoyl [e.g. methoxycarbonylcinnamoylglycyl, ethoxycarbonylcinnamoylglycyl, etc.], amino acid residue substituted with carbamoyl-ar(lower)-alkenoyl [e.g. carbamoylcinnamoylglycyl, etc.], amino acid residue substituted with lower alkylcarbamoyl-ar(lower)alkenoyl [e.g. methylcarbamoylcinnamoylglycyl, ethylcarbamoylcinnamoylglycyl, dimethylcarbamoylcinnamoylglycyl, propylcarbamoylcinnamoylglycyl, isopropylcarbamoylcinnamoylglycyl, diethylcarbamoylcinnamoylglycyl, N-methyl-N-ethylcarbamoylcinnamoylglycyl, etc.], amino acid residue substituted with hydroxy(lower)alkylcarbamoyl-ar(lower) alkenoyl [e.g. hydroxyethylcarbamoylcinnamoylglycyl, bis (hydroxyethyl)carbamoylcinnamoylglycyl, etc.], amino acid residue substituted with N-[hydroxy(lower)alkyl]-N-(lower alkyl)carbamoyl-ar(lower)alkenoyl [e.g. N-hydroxyethyl-N-methylcarbamoylcinnamoylglycyl, etc.], amino acid residue substituted with lower alkoxy(lower)alkylcarbamoyl-ar (lower)alkenoyl [e.g. methoxymethylcarbamoylcinnamoylglycyl, methoxyethylcarbamoylcinnamoylglycyl, bis (methoxyethyl)-carbamoylcinnamoylglycyl, ethoxyethylcarbamoylcinnamoylglycyl, methoxypropylcarbamoylcinnamoylglycyl, bis (ethoxyethyl)carbamoylcinnamoylglycyl, etc.], amino acid residue substituted with N-[lower alkoxy(lower)alkyl]-N-(lower alkyl)carbamoyl-ar(lower)-alkenoyl [e.g. N-methoxyethyl-N-methylcarbamoylcinnamoylglycyl, N-ethoxyethyl-N-methylcarbamoylcinnamoylglycyl, etc.], amino acid residue substituted with heterocyclic(lower) alkylcarbamoyl-ar(lower)alkenoyl [e.g. pyridylmethylcarbamoylcinnamoylglycyl, furylmethylcarbamoylcinnamoylglycyl, thienylmethylcarbamoylcinnamoylglycyl, etc.], amino acid residue substituted with N-[heterocyclic(lower)alkyl]-N-(lower alkyl)carbamoyl-ar(lower)alkenoyl [e.g. N-pyridylmethyl-N-methylcarbamoylcinnamoylglycyl, etc.], amino acid residue substituted with heterocycliccarbamoyl-ar(lower)alkenoyl [e.g. morpholinylcarbamoylcinnamoylglycyl, thienylcarbamoylcinnamoylglycyl, pyridylcarbamoylcinnamoylglycyl, pyrimidinylcarbamoylcinnamoylglycyl, tetrazolylcarbamoylcinnamoylglycyl, etc.], amino acid residue substituted with optionally substituted heterocycliccarbonyl-ar(lower)alkenoyl [e.g. morpholinocarbonylcinnamoylglycyl, pyrrolidinylcarbonylcinnamoylglycyl, piperidinocarbonylcinnamoylglycyl, tetrahydropyridylcarbonylcinnamoylglycyl, methylpiperazinylcarbonylcinnamoylglycyl, etc.], amino acid residue substituted with lower alkenylcarbamoyl-ar (lower)alkenoyl [e.g. vinylcarbamoylcinnamoylglycyl, allylcarbamoylcinnamoylglycyl, methylpropenylcarbamoylcinnamoylglycyl, etc.], amino acid residue substituted with lower alkynylcarbamoyl-ar (lower)alkenoyl [e.g. ethynylcarbamoylcinnamoylglycyl, propynylcarbamoylcinnamoylglycyl, etc.], amino acid residue substituted with amino(lower)alkylcarbamoyl-ar(lower) alkenoyl [e.g. aminomethylcarbamoylcinnamoylglycyl, aminoethylcarbamoylcinnamoylglycyl, etc.], amino acid residue substituted with lower alkylamino(lower) alkylcarbamoyl-ar(lower)alkenoyl [e.g. methylaminomethylcarbamoylcinnamoylglycyl, methylaminoethylcarbamoylcinnamoylglycyl, ethylaminoethylcarbamoylcinnamoylglycyl, dimethylaminoethylcarbamoylcinnamoylglycyl, etc.], amino acid residue substituted with lower alkylcarbamoyloxy(lower)alkylcarbamoyl-ar(lower) alkenoyl [e.g. methylcarbamoyloxymethylcarbamoylcinnamoylglycyl, methylcarbamoyloxyethylcarbamoylcinnamoylglycyl, ethylcarbamoyloxyethylcarbamoylcinnamoylglycyl, dimethylcarbamoyloxyethylcarbamoylcinnamoylglycyl, etc.], amino acid residue substituted with lower alkylcarbamoyl(lower)alkylcarbamoyl-ar(lower)alkenoyl [e.g. methylcarbamoylmethylcarbamoylcinnamoylglycyl, methylcarbamoylethylcarbamoylcinnamoylglycyl, ethylcarbamoylethylcarbamoylcinnamoylglycyl, dimethylcarbamoylethylcarbamoylcinnamoylglycyl, etc.], amino acid residue substituted with lower alkoxycarbonyl (lower)alkylcarbamoyl-ar(lower)alkenoyl [e.g. methoxycarbonylmethylcarbamoylcinnamoylglycyl, methoxycarbonylethylcarbamoylcinnamoylglycyl, ethoxycarbonylmethylcarbamoylcinnamoylglycyl, ethoxycarbonylethylcarbamoylcinnamoylglycyl, etc.], amino acid residue substituted with carboxy(lower) alkylcarbamoyl-ar(lower)alkenoyl [e.g.

carboxymethylcarbamoylcinnamoylglycyl, carboxyethylcarbamoylcinnamoylglycyl, etc.], amino acid residue substituted with [lower alkylcarbamoyl-ar(lower)alkyl]carbamoyl-ar(lower)alkenoyl [e.g. (methylcarbamoylphenethyl)carbamoylcinnamoylglycyl, (ethylcarbamoylphenethyl)carbamoylcinnamoylglycyl, etc.], amino acid residue substituted with [lower alkoxycarbonyl-ar(lower)alkyl]carbamoyl-ar(lower)alkenoyl [e.g. (methoxycarbonylphenethyl)carbamoylcinnamoylglycyl, (ethoxycarbonylphenethyl)carbamoylcinnamoylglycyl, etc.], amino acid residue substituted with [carboxy-ar(lower)alkyl]carbamoyl-ar(lower)alkenoyl [e.g. (carboxy-phenethyl)carbamoylcinnamoylglycyl, etc.], amino acid residue substituted with N-[lower alkylcarbamoyl(lower)alkyl]-N-(lower alkyl) carbamoyl-ar(lower)alkenoyl [e.g. N-(methylcarbamoylmethyl)-N-methylcarbamoylcinnamoylglycyl, N-(methylcarbamoylethyl)-N-methylcarbamoylcinnamoylglycyl, N-(ethylcarbamoylethyl)-N-methylcarbamoylcinnamoylglycyl, N-(dimethylcarbamoylethyl)-N-methylcarbamoylcinnamoylglycyl, etc.], amino acid residue substituted with N-[lower alkoxycarbonyl(lower)alkyl]-N-(lower alkyl)carbamoyl-ar(lower)alkenoyl [e.g. N-methoxycarbonylmethyl-N-methylcarbamoylcinnamoylglycyl, N-methoxycarbonylethyl-N-methylcarbamoylcinnamoylglycyl, N-ethoxycarbonylmethyl-N-methylcarbamoylcinnamoylglycyl, N-ethoxycarbonylethyl-N-methylcarbamoylcinnamoylglycyl, etc.], amino acid residue substituted with N-[carboxy(lower)alkyl]-N-(lower alkyl)carbamoyl-ar(lower)alkenoyl [e.g. N-carboxymethyl-N-methylcarbamoylcinnamoylglycyl, N-carboxyethyl-N-methylcarbamoylcinnamoylglycyl, etc.], amino acid residue substituted with arylcarbamoyl-ar(lower)alkenoyl [e.g. phenylcarbamoylcinnamoylglycyl, naphthylcarbamoylcinnamoylglycyl, etc.], etc., etc., amino acid residue substituted with ar(lower)alkynoyl [e.g. phenylpropioloylglycyl, etc.], amino acid residue substituted with substituted or unsubstituted heterocyclic(lower)alkenoyl, in which said heterocyclic group may be substituted with the above-mentioned lower alkyl or lower alkoxy, such as amino acid residue substituted with heterocyclic(lower)alkenoyl [e.g. morpholinylacryloylglycyl, pyridylacryloylglycyl, thienylacryloylglycyl, etc.], amino acid residue substituted with heterocyclic(lower)alkyl-heterocyclic(lower)alkenoyl [e.g. pyridylmethylpyridylacryloylglycyl, pyridylethylpyridylacryloylglycyl, quinolylethylpyridylacryloylglycyl, etc.], amino acid residue substituted with heterocyclic(lower)alkenyl-heterocyclic(lower)alkenoyl [e.g. pyridylvinylpyridylacryloylglycyl, quinolylvinylpyridylacryloylglycyl, etc.], amino acid residue substituted with amino-heterocyclic(lower)alkenoyl [e.g. aminopyridylacryloylglycyl, etc.], amino acid residue substituted with lower alkylamino-heterocyclic(lower)alkenoyl [e.g. methylaminopyridylacryloylglycyl, dimethylaminopyridylacryloylglycyl, etc.], amino acid residue substituted with acylamino-heterocyclic(lower)alkenoyl, for example, amino acid residue substituted with lower alkanoylamino-heterocyclic(lower)alkenoyl [e.g. acetylaminopyridylacryloylglycyl, propionylaminopyridylacryloylglycyl, etc.], amino acid residue substituted with lower alkenoylamino-heterocyclic(lower)alkenoyl [e.g. acryloylaminopyridylacryloylglycyl, crotonoylaminopyridylacryloylglycyl, etc.], amino acid residue substituted with heterocyclic(lower)alkanoylamino-heterocyclic (lower)-alkenoyl [e.g. pyridylacetylaminopyridylacryloylglycyl, thienylacetylaminopyridylacryloylglycyl, etc.], amino acid residue substituted with heterocycliccarbonylamino-heterocyclic(lower)alkenoyl which may be substituted with lower alkyl [e.g. pyridylcarbonylaminopyridylacryloylglycyl, furylcarbonylaminopyridylacryloylglycyl, methylpyridylcarbonylaminopyridylacryloylglycyl, etc.], amino acid residue substituted with lower alkanoylamino-(lower) alkanoylamino-heterocyclic(lower)alkenoyl [e.g. acetylaminoacetylaminopyridylacryloylglycyl, acetylaminopropionylaminopyridylacryloylglycyl, etc.], amino acid residue substituted with lower alkoxycarbonyl-(lower) alkanoylamino-heterocyclic(lower)alkenoyl [e.g. ethoxycarbonylacetylaminopyridylacryloylglycyl, ethoxycarbonylpropionylaminopyridylacryloylglycyl, etc.], amino acid residue substituted with lower alkoxy(lower) alkanoylamino-heterocyclic(lower)alkenoyl [e.g. methoxyacetylaminopyridylacryloylglycyl, methoxypropionylaminopyridylacryloylglycyl, ethoxypropionylaminopyridylacryloylglycyl, etc.], etc., amino acid residue substituted with lower alkylureido-heterocyclic(lower)alkenoyl [e.g. methylureidopyridylacryloylglycyl, etc.], amino acid residue substituted with acyl-heterocyclic(lower)alkenoyl, for example, amino acid residue substituted with carboxy-heterocyclic(lower)alkenoyl [e.g. carboxypyridylacryloylglycyl, etc.], amino acid residue substituted with lower alkoxycarbonyl-heterocyclic(lower)alkenoyl [e.g. ethoxycarbonylpyridylacryloylglycyl, etc.], amino acid residue substituted with lower alkanoyl-heterocyclic(lower)alkenoyl [e.g. acetylpyridylacryloylglycyl, acetyltetrahydroquinolylacryloylglycyl, etc.], amino acid residue substituted with lower alkylcarbamoyl-heterocyclic(lower)alkenoyl [e.g. methylcarbamoylpyridylacryloylglycyl, ethylcarbamoylpyridylacryloylglycyl, dimethylcarbamoylpyridylacryloylglycyl, diethylcarbamoylpyridylacryloylglycyl, isopropylcarbamoylpyridylacryloylglycyl, N-ethyl-N-methylcarbamoylpyridylacryloylglycyl, etc.], amino acid residue substituted with lower alkoxy(lower) alkylcarbamoyl-heterocyclic(lower)alkenoyl [e.g. methoxymethylcarbamoylpyridylacryloylglycyl, methoxyethylcarbamoylpyridylacryloylglycyl, methoxypropylcarbamoylpyridylacryloylglycyl, ethoxyethylcarbamoylpyridylacryloylglycyl, bis(methoxyethyl) carbamoylpyridylacryloylglycyl, etc.], amino acid residue substituted with hydroxy(lower)alkylcarbamoyl-heterocyclic(lower)alkenoyl [e.g. hydroxymethylcarbamoylpyridylacryloylglycyl, hydroxyethylcarbamoylpyridylacryloylglycyl, bis(hydroxyethyl) carbamoylpyridylacryloylglycyl, etc.], amino acid residue substituted with heterocycliccarbamoyl-heterocyclic(lower)alkenoyl [e.g. pyridylcarbamoylpyridylacryloylglycyl, morpholinylcarbamoylpyridylacryloylglycyl, thienylcarbamoylpyridylacryloylglycyl, pyrimidinylcarbamoylpyridylacryloylglycyl, etc.], amino acid residue substituted with heterocyclic-(lower) alkylcarbamoyl-heterocyclic(lower)alkenoyl [e.g. pyridylmethylcarbamoylpyridylacryloylglycyl, furylmethylcarbamoylpyridylacryloylglycyl, thienylmethylcarbamoylpyridylacryloylglycyl, etc.], amino acid residue substituted with heterocycliccarbonyl-heterocyclic (lower)alkenoyl [e.g. morpholinocarbonylpyridylacryloylglycyl, pyrrolidinylcarbonylpyridylacryloylglycyl, piperidinocarbonylpyridylacryloylglycyl, etc.], amino acid residue substituted with lower alkenylcarbamoyl-heterocyclic(lower)alkenoyl [e.g. vinylcarbamoylpyridylacryloylglycyl, allylcarbamoylpyridylacryloylglycyl, etc.], amino acid residue substituted with lower alkynylcarbamoyl-heterocyclic (lower)alkenoyl [e.g. ethynylcarbamoylpyridylacryloylglycyl, propynylcarbamoylpyridylacryloylglycyl, etc.], etc., etc., amino acid residue substituted with heterocyclicthio(lower) alkanoyl [e.g. pyridylthioacetylglycyl, pyrimidinylthioacetylglycyl, imidazolylthiopropionylglycyl, etc.], amino acid residue substituted with optionally substituted heterocycliccarbonyl [e.g. morpholinocarbonylglycyl, indolylcarbonylglycyl, 4-methyl-1-piperazinylcarbonylglycyl, etc.], amino acid residue substituted with cyclo(lower)alkylcarbonyl [e.g. cyclopropylcarbonylglycyl, cyclopentylcarbonylglycyl, cyclohexylcarbonylglycyl, cyclohexylcarbonylsarcosyl, etc.], amino acid residue substituted with lower alkoxycarbonyl [e.g. methoxycarbonylglycyl, tert-butoxycarbonylglycyl, tert-butoxycarbonylsarcosyl, tert-butoxycarbonylalanyl, etc.], amino acid residue substituted with aryloxycarbonyl [e.g. phenoxycarbonylglycyl, etc.], amino acid residue substituted with aroyl(lower)alkanoyl [e.g. phenyloxalylglycyl, benzoylpropionylglycyl, etc.], amino acid residue substituted with aroyl [e.g. benzoylglycyl, naphthoylglycyl, benzoylsarcosyl, benzoylalanyl, etc.], amino acid residue substituted with nitro-aryloxycarbonyl [e.g. nitrophenyloxycarbonylglycyl, etc.], amino acid residue substituted with carbamoyl [e.g. carbamoylglycyl, carbamoylalanyl, carbamoylsarcosyl, carbamoyl-β-alanyl, etc.], amino acid residue substituted with lower alkylcarbamoyl [e.g. methylcarbamoylglycyl, ethylcarbamoylglycyl, propylcarbamoylglycyl, isopropylcarbamoylglycyl, methylcarbamoylsarcosyl, ethylcarbamoylalanyl, isopropylcarbamoyl-β-alanyl, pentylcarbamoylglycyl, etc.], amino acid residue substituted with lower alkoxycarbonyl(lower)alkylcarbamoyl [e.g. methoxycarbonylmethylcarbamoylglycyl, ethoxycarbonylmethylcarbamoylglycyl, etc.], amino acid residue substituted with lower alkenylcarbamoyl [e.g. vinylcarbamoylglycyl, allylcarbamoylglycyl, allylcarbamoylsarcosyl, etc.], amino acid residue substituted with cyclo(lower)alkylcarbamoyl [e.g. cyclopropylcarbamoylglycyl, cyclohexylcarbamoylglycyl, cyclohexylcarbamoylsarcosyl, etc.], amino acid residue substituted with arylcarbamoyl [e.g. phenylcarbamoylglycyl, naphthylcarbamoylglycyl, tolylcarbamoylglycyl, ethylphenylcarbamoylglycyl, phenylcarbamoylalanyl, phenylcarbamoylsarcosyl, etc.], amino acid residue substituted with lower alkoxy-arylcarbamoyl [e.g. methoxyphenylcarbamoylglycyl, ethoxyphenylcarbamoylglycyl, methoxyphenylcarbamoylalanyl, etc.], amino acid residue substituted with halo(lower)alkyl-arylcarbamoyl [e.g. triluoromethylphenylcarbamoylglycyl, trifluoromethylphenylcarbamoylalanyl, trifluoromethylphenylcarbamoylsarcosyl, etc.], amino acid residue substituted with halo-arylcarbamoyl [e.g. chlorophenylcarbamoylglycyl, fluorophenylcarbamoylglycyl, fluorophenylcarbamoylalanyl, etc.], amino acid residue substituted with hydroxy(lower)alkyl-arylcarbamoyl [e.g. hydroxymethylphenylcarbamoylglycyl, hydroxyethylphenylcarbamoylglycyl, hydroxyethylphenylcarbamoylalanyl, etc.], amino acid residue substituted with nitro-arylcarbamoyl [e.g. nitrophenylcarbamoylglycyl, etc.], amino acid residue substituted with cyano-arylcarbamoyl [e.g. cyanophenylcarbamoylglycyl, etc.], amino acid residue substituted with amino-arylcarbamoyl [e.g. aminophenylcarbamoylglycyl, etc.], amino acid residue substituted with lower alkylamino-arylcarbamoyl [e.g. methylaminophenylcarbamoylglycyl, ethylaminophenylcarbamoylglycyl, dimethylaminophenylcarbamoylglycyl, etc.], amino acid residue substituted with lower alkanoylamino-arylcarbamoyl [e.g. acetylaminophenylcarbamoylglycyl, propionylaminophenylcarbamoylglycyl, etc.], amino acid residue substituted with N-(lower alkanoyl)-N-(lower alkyl)amino-arylcarbamoyl [e.g. N-acetyl-N-methylaminophenylcarbamoylglycyl, N-propionyl-N-methylaminophenylcarbamoylglycyl, etc.], amino acid residue substituted with lower alkoxy(lower)alkanoylamino-arylcarbamoyl [e.g. methoxyacetylaminophenylcarbamoylglycyl, methoxypropionylaminophenylcarbamoylglycyl, etc.], amino acid residue substituted with lower alkoxycarbonyl(lower)alkanoylamino-arylcarbamoyl [e.g. ethoxycarbonylacetylaminophenylcarbamoylglycyl, methoxycarbonylpropionylaminophenylcarbamoylglycyl, etc.], amino acid residue substituted with carboxyamino-arylcarbamoyl [e.g. carboxyaminophenylcarbamoylglycyl, etc.], amino acid residue substituted with lower alkoxycarbonylamino-arylcarbamoyl [e.g. ethoxycarbonylaminophenyl-carbamoylglycyl, etc.], amino acid residue substituted with aroylamino-arylcarbamoyl [e.g. benzoylaminophenylcarbamoylglycyl, etc.], amino acid residue substituted with heterocycliccarbonylamino-arylcarbamoyl [e.g. pyridylcarbonylaminophenylcarbamoylglycyl, furylcarbonylaminophenylcarbamoylglycyl, morpholinocarbonylaminophenylcarbamoylglycyl, etc.], amino acid residue substituted with heterocyclic(lower)alkanoylamino-arylcarbamoyl [e.g. pyridylacetylaminophenylcarbamoylglycyl, thienylacetylaminophenylcarbamoylglycyl, etc.], amino acid residue substituted with ureido-arylcarbamoyl [e.g. ureidophenylcarbamoylglycyl, etc.], amino acid residue substituted with lower alkylureido-arylcarbamoyl [e.g. methylureidophenylcarbamoylglycyl, ethylureidophenylcarbamoylglycyl, etc.], amino acid residue substituted with hydroxyimino(lower)alkyl-arylcarbamoyl [e.g. hydroxyiminoethylphenylcarbamoylglycyl, etc.], amino acid residue substituted with lower alkoxyimino(lower)alkyl-arylcarbamoyl [e.g. methoxyiminoethylphenylcarbamoylglycyl, etc.], amino acid residue substituted with lower alkylhydrazono(lower)alkyl-arylcarbamoyl [e.g. methylhydrazonoethylphenylcarbamoylglycyl, dimethylhydrazonoethylphenylcarbamoylglycyl, etc.], amino acid residue substituted with optionally substituted heterocyclic-arylcarbamoyl [e.g. oxopyrrolidinylphenylcarbamoylglycyl, oxopiperidinophenylcarbamoylglycyl, dioxopyrrolidinylphenylcarbamoylglycyl, oxooxazolidinylphenylcarbamoylglycyl, pyrrolylphenylcarbamoylglycyl, etc.], amino acid residue substituted with acyl-arylcarbamoyl, for example, amino acid residue substituted with lower alkanoyl-arylcarbamoyl [e.g. acetylphenylcarbamoylglycyl, propionylphenylcarbamoylglycyl, etc.], amino acid residue substituted with heterocycliccarbonyl-arylcarbamoyl [e.g. morpholinocarbonylphenylcarbamoylglycyl, piperidinocarbonylphenylcarbamoylglycyl, piperazinylcarbonylphenylcarbamoylglycyl, thiomorpholinocarbonylphenylcarbamoylalanyl, pyrrolidinylcarbonylphenylcarbamoylglycyl, 1,2,3,6-tetrahydropyridylcarbonylphenylcarbamoylglycyl, etc.], amino acid residue substituted with carboxy-arylcarbamoyl [e.g. carboxyphenylcarbamoylglycyl, etc.], amino acid residue substituted with lower alkoxycarbonyl-arylcarbamoyl [e.g. methoxycarbonylphenylcarbamoylglycyl, ethoxycarbonyl-phenylcarbamoylglycyl, etc.], amino acid residue substituted with carbamoyl-arylcarbamoyl [e.g. carbamoylphenylcarbamoylglycyl, etc.], amino acid residue substituted with lower alkylcarbamoyl-arylcarbamoyl [e.g. methylcarbamoylphenylcarbamoylglycyl, ethylcarbamoylphenylcarbamoylglycyl, propylcarbamoylphenylcarbamoylglycyl, dimethylcarbamoylphenylcarbamoylglycyl, diethylcarbamoylphenylcarbamoylglycyl, N-ethyl-N-methylcarbamoylphenylcarbamoylglycyl, N-isopropyl-N-methylcarbamoylphenylcarbamoylglycyl, etc.], amino acid residue substituted with heterocycliccarbonyl-arylcarbamoyl having lower alkyl [e.g. methylpiperazinylcarbonylphenylcarbamoylglycyl, ethylpiperazinylcarbonylphenylcarbamoylglycyl, etc.], amino acid residue substituted with heterocycliccarbonyl-arylcarbamoyl having aryl [e.g. phenylpiperazinylcarbonylphenylcarbamoylglycyl, etc.], amino acid residue substituted with heterocycliccarbonyl-arylcarbamoyl having a heterocyclic group [e.g. pyridylpiperazinylcarbonylphenylcarbamoylglycyl, etc.], amino acid residue substituted with heterocycliccarbonyl-arylcarbamoyl having lower alkanoyl [e.g. acetylpiperazinylcarbonylphenylcarbamoylglycyl, etc.], amino acid residue substituted with heterocycliccarbonyl-arylcarbamoyl having lower alkoxycarbonyl [e.g. ethoxycarbonylpiperazinylcarbonyl-phenylcarbamoylglycyl, etc.], amino acid residue substituted with heterocycliccarbonyl-arylcarbamoyl having lower alkylamino [e.g. methylaminopiperazinylcarbonyl-phenylcarbamoylglycyl, dimethylaminopiperidinocarbonyl-phenylcarbamoylglycyl, etc.], amino acid residue substituted with heterocycliccarbonyl-arylcarbamoyl having lower alkylcarbamoyl [e.g. methyl-carbamoylpiperazinylcarbonylphenylcarbamoylglycyl, etc.], amino acid residue substituted with hydroxy(lower)alkylcarbamoyl-arylcarbamoyl [e.g. hydroxymethylcarbamoylphenylcarbamoylglycyl, hydroxyethylcarbamoylphenylcarbamoylglycyl, bis(hydroxyethyl)carbamoylphenylcarbamoylglycyl, etc.], amino acid residue substituted with N-[hydroxy(lower)alkyl]-N-(lower alkyl)carbamoyl-arylcarbamoyl [e.g. N-(hydroxyethyl)-N-methylcarbamoyl-phenylcarbamoylglycyl, etc.], amino acid residue substituted with lower alkoxy(lower)alkylcarbamoyl-arylcarbamoyl [e.g. methoxymethylcarbamoylphenylcarbamoylglycyl, methoxyethylcarbamoylphenylcarbamoylglycyl, methoxyethylcarbamoylphenylcarbamoylglycyl, bis(methoxyethyl)carbamoylphenylcarbamoylglycyl, bis(ethoxyethyl)carbamoylphenylcarbamoylglycyl, etc.], amino acid residue substituted with N-[lower alkoxy(lower) alkyl]-N-(lower alkyl)carbamoyl-arylcarbamoyl [e.g. N-(methoxyethyl)-N-methylcarbamoylphenylcarbamoylglycyl, N-(methoxypropyl)-N-methylcarbamoylphenylcarbamoylglycyl, etc.], amino acid residue substituted with lower alkylamino (lower) alkylcarbamoyl-arylcarbamoyl [e.g. methylaminoethylcarbamoylphenylcarbamoylglycyl, dimethylaminoethylcarbamoylphenylcarbamoylglycyl, etc.], amino acid residue substituted with N-[lower alkylamino(lower)alkyl-N-(lower alkyl)carbamoyl-arylcarbamoyl [e.g. N-(dimethyaminoethyl)-N-methylcarbamoylphenylcarbamoylglycyl, N-(dimethylaminopropyl)-N-methylcarbamoylphenylcarbamoylglycyl, etc.], amino acid residue substituted with heterocycliccarbamoyl-arylcarbamoyl [e.g. morpholinylcarbamoylphenylcarbamoylglycyl, thienylcarbamoylphenylcarbamoylglycyl, pyridylcarbamoylphenylcarbamoylglycyl, pyrimidinylcarbamoylphenylcarbamoylglycyl, etc.], amino acid residue substituted with N-(heterocyclic)-N-(lower alkyl)carbamoyl-arylcarbamoyl [e.g. N-pyridyl-N-methylcarbamoylphenylcarbamoylglycyl, etc.], amino acid residue substituted with heterocyclic(lower)alkylcarbamoyl-arylcarbamoyl [e.g. pyridylmethylcarbamoylphenylcarbamoylglycyl, pyridylethylcarbamoylphenylcarbamoylglycyl, thienylmethylcarbamoylphenylcarbamoylglycyl, etc.], amino acid residue substituted with N-[heterocyclic(lower)alkyl]-N-(lower alkyl)carbamoyl-arylcarbamoyl [e.g. N-pyridylmethyl-N-methylcarbamoyl-phenylcarbamoylglycyl, etc.], amino acid residue substituted with N-[heterocyclic(lower)alkyl]-N-[lower alkoxy(lower)alkyl]-carbamoyl-arylcarbamoyl [e.g. N-pyridylmethyl-N-methoxyethylcarbamoylphenylcarbamoylglycyl, etc.], amino acid residue substituted with arylcarbamoyl-arylcarbamoyl [e.g. phenylcarbamoylphenylcarbamoylglycyl, etc.], amino acid residue substituted with lower alkylaminoarylcarbamoyl-arylcarbamoyl [e.g. dimethylamino-phenylcarbamoylphenylcarbamoylglycyl, etc.], etc., amino acid residue substituted with arylthiocarbamoyl [e.g. phenylthiocarbamoylglycyl, naphthylthiocarbamoylglycyl, phenylthiocarbamoylalanyl, phenylthiocarbamoylsarcosyl, etc.], amino acid residue substituted with ar(lower)alkylcarbamoyl [e.g. benzylcarbamoylglycyl, benzylcarbamoylsarcosyl, benzylcarbamoylalanyl, etc.], amino acid residue substituted with aroylcarbamoyl [e.g. benzoylcarbamoylglycyl, etc.], amino acid residue substituted with heterocycliccarbamoyl [e.g. pyridylcarbamoylglycyl, pyridylcarbamoylalanyl, pyridylcarbamoylsarcosyl, thienylcarbamoylglycyl, pyrazolylcarbamoylglycyl, pyrimidinylcarbamoylglycyl, quinolylcarbamoylglycyl, isoquinolylcarbamoylglycyl, etc.], amino acid residue substituted with heterocyclic(lower)alkylcarbamoyl [e.g. pyridylmethylcarbamoylglycyl, pyridylethylcarbamoylglycyl, thienylmethylcarbamoylglycyl, etc.], amino acid residue substituted with arylaminocarbamoyl [e.g. phenylaminocarbamoylglycyl, etc.], amino acid residue substituted with ar(lower)alkenylsulfonyl [e.g. styrylsulfonylglycyl, cinnamylsulfonylglycyl, etc.], amino acid residue substituted with lower alkylsulfonyl [e.g. mesylglycyl, ethylsulfonylglycyl, mesylsarcosyl, mesylalanyl, etc.], amino acid residue substituted with phthaloyl [e.g. phthaloylglycyl, phthaloylalanyl, phthaloyl-β-alanyl, etc.], amino acid residue having unsubstituted amino acid residue [e.g. glycylglycyl, alanylglycyl, sarcosylglycyl, prolylglycyl, glycylsarcosyl, prolylsarcosyl, etc.], amino acid residue having substituted amino acid residue [e.g. amino acid residue having amino acid residue substituted with lower alkyl (e.g. dimethylglycylglycyl, diethylglycylglycyl, dimethylglycylsarcosyl, ethylsarcosylglycyl, isopropylsarcosylglycyl, ethylglycylglycyl, propylglycylglycyl, isopropylglycylglycyl, ethylglycylalanyl, dimethylglycylalanyl, dimethylalanylglycyl, dimethyl-β-alanylglycyl, etc.), amino acid residue having amino acid residue substituted with a heterocyclic group (e.g. morpholinoglycylglycyl, piperidinoglycylglycyl, pyridylglycylglycyl, piperidinosarcosylglycyl, etc.), amino acid residue having amino acid residue substituted with heterocyclic(lower)alkyl (e.g. pyridylmethylglycylglycyl, imidazolylmethylglycylglycyl, furylmethylglycylglycyl, thienylmethylsarcosylglycyl, etc.), amino acid residue having amino acid residue substituted with cycloalkyl (e.g. cyclopropylglycylglycyl, cyclobutylglycylglycyl, cyclopentylglycylglycyl, cyclohexylglycylglycyl, cycloheptylglycylglycyl, cyclooctylglycylglycyl, adamantylglycylglycyl, cyclohexylsarcosylglycyl, cycloheptylsarcosylglycyl, cyclohexylglycylsarcosyl, cyclohexylglycylalanyl, etc.), amino acid residue having amino acid residue substituted with aryl (e.g. phenylglycylglycyl, phenylsarcosylglycyl, etc.), amino acid residue having amino acid residue substituted with acyl {e.g. amino acid residue having amino acid residue substituted with alkanoyl (e.g. acetylglycylglycyl, acetylprolylglycyl, propionylglycylglycyl, acetylalanylglycyl, etc.), amino acid residue having amino acid residue substituted with lower alkoxycarbonyl (e.g. tert-butoxycarbonylglycylglycyl, tert-butoxycarbonylprolylglycyl, etc.), amino acid residue having amino acid residue substituted with phthaloyl (e.g. phthaloylglycylglycyl, etc.), etc.}, amino acid residue having amino acid residue substituted with ar(lower)alkyl (e.g. benzylglycylglycyl, etc.), etc.], etc., or the like.

Suitable "acyl having amino" may be unsubstituted amino acid residue, amino acid residue having unsubstituted amino acid residue, or the like, and preferred examples thereof can be referred to those exemplified above.

Suitable "acyl having acylamino" may be amino acid residue substituted with acyl, amino acid residue having amino acid residue substituted with acyl, or the like, and preferred examples thereof can be referred to those exemplified above.

Suitable substituents in the term "amino optionally having suitable substituent(s)" may be the above-mentioned lower alkyl, the above-mentioned acyl, ar(lower)alkyl [e.g. benzyl, phenethyl, trityl, etc.], carboxy(lower)alkyl [e.g. carboxymethyl, carboxyethyl, carboxypropyl, etc.], lower alkoxycarbonyl(lower)alkyl [e.g. methoxycarbonylmethyl, ethoxycarbonylmethyl, methoxycarbonylethyl, ethoxycarbonylpropyl, etc.], heterocyclic(lower)alkyl [e.g. pyridylmethyl, pyridylethyl, etc.], or the like.

Suitable "a leaving group" may be a conventional acid residue such as halogen [e.g. fluoro, chloro, bromo and iodo], arenesulfonyloxy [e.g. benzenesulfonyloxy, tosyloxy, etc.], alkanesulfonyloxy [e.g. mesyloxy, ethanesulfonyloxy, etc.], and the like.

Suitable pharmaceutically acceptable salts of the object compound [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid addition salt [e.g. formate, acetate, trifluoroacetate, maleate, tartrate, oxalate, methanesulfonate, benzenesulfonate, toluenesulfonate, etc.], an inorganic acid addition salt [e.g. hydrochloride, hydrobromide, sulfate, phosphate, etc.], a salt with an amino acid (e.g. arginine salt, aspartic acid salt, glutamic acid salt, etc.], an intramolecular salt and the like.

Preferred embodiments of the object compound [I] are as follows:

(i) a compound of the formula

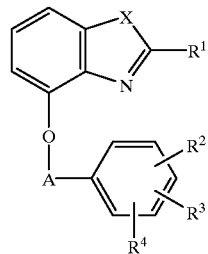

wherein

X is O, S or N—$R^5$, $R^1$ and $R^5$ are each lower alkyl, aryl or ar(lower)alkyl, $R^2$ is hydrogen or halogen, $R^3$ is halogen, $R^4$ is amino optionally having suitable substituent(s), and A is lower alkylene; or (ii) a compound of the formula:

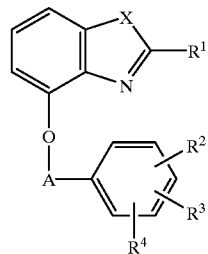

wherein

X is O, S or N—$R^5$, $R^1$ and $R^5$ are each lower alkyl, lower alkoxy(lower)alkyl, lower alkoxy, lower alkylthio, lower alkylamino, acyl(lower)alkyl, acyl, aryl or ar(lower)alkyl, $R^2$ is hydrogen, halogen, lower alkyl or lower alkoxy, $R^3$ is halogen, lower alkyl or lower alkoxy, $R^4$ is amino optionally having suitable substituent(s), and A is lower alkylene.

With respect to the salts of the compounds [Ia] to [Ic] in the Processes 2 to 3, it is to be noted that these compounds are included within the scope of the compound [I], and accordingly the suitable examples of the salts of these compounds are to be referred to those as exemplified for the object compound [I].

The processes for preparing the object compound [I] are explained in detail in the following.

Process 1

The object compound [I] or its salt can be prepared by reacting a compound [II] or its salt with a compound [III] or its salt.

Suitable salts of the compounds [II] and [III] may be the same as those exemplified for the compound [I].

The reaction is preferably carried out in the presence of a base such as alkali metal [e.g. lithium, sodium, potassium, etc.], the hydroxide or carbonate or bicarbonate thereof [e.g. sodium hydroxide, potassium carbonate, potassium bicarbonate, etc.], alkali metal alkoxide [e.g. sodium methoxide, sodium ethoxide, potassium tert-butoxide, etc.], or the like.

This reaction is usually carried out in a conventional solvent such as tetrahydrofuran, dioxane, N,N-dimethylformamide, acetone, or the like.

The reaction temperature is not critical, and the reaction is usually carried out under cooling to heating.

Process 2

The object compound [Ib] or its salt can be prepared by acylating a compound [Ia] or its salt.

The acylation is carried out in the presence of an acylating agent.

Suitable acylating agents are the corresponding carboxylic acid or sulfonic acid compounds, which are represented by the formula: R—OH wherein R is acyl, and reactive derivatives thereof, and the corresponding isocyanate or isothiocyanate compounds.

As suitable said reactive derivatives, there may be mentioned acid halides, acid anhydrides, active amides and active esters. Suitable examples are acid halides such as acid chloride and acid bromide, mixed acid anhydrides with various acids [e.g. substituted phosphoric acid such as dialkyl phosphoric acid, sulfuric acid, aliphatic carboxylic acid, aromatic carboxylic acid, etc.], symmetric acid anhydrides, active amides with various imidazoles, and active esters such as p-nitrophenyl ester and N-hydroxysuccinimide ester. The kind of such reactive derivatives can be selected depending on the kind of acyl group to be introduced.

The reaction is usually carried out in a conventional solvent, such as methylene chloride, chloroform, pyridine, dioxane, tetrahydrofuran, N,N-dimethylformamide, or the like. In case that the acylating agent is liquid, it can also be used as a solvent. In case that the carboxylic acid or sulfonic acid compounds are used as acylating agent in the free acid form or salt form, it is preferable to carry out the reaction in the presence of a conventional condensing agent such as N,N'-dicyclohexylcarbodiimide or the like.

The reaction temperature is not critical and the reaction can be carried out under cooling, at ambient temperature, or under heating.

This reaction is preferably carried out in the presence of a conventional inorganic base or in the presence of a conventional organic base.

Process 3

The object compound [Ic] or its salt can be prepared by reacting a compound [IV] or its salt with a compound [V].

Suitable salts of the compound [IV] can be referred to the ones as exemplified for the compound [I].

The reaction is usually carried out in a conventional solvent such as acetic acid, or the like under cooling or at ambient temperature.

The starting compound [IV] or its salt can be prepared, for example, by a process as illustrated in the following reaction scheme.

Process A

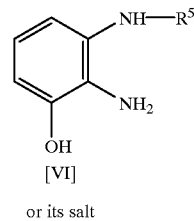 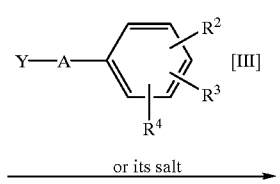

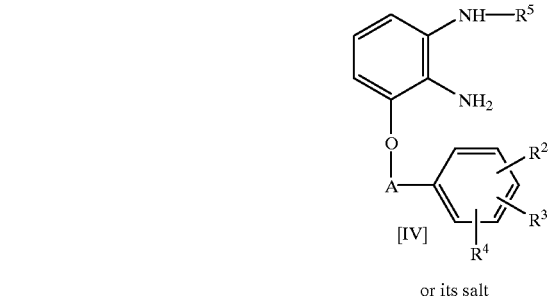

wherein $R^2$, $R^3$, $R^4$, $R^5$, A and Y are each as defined above.

The compound [IV] or its salt can be prepared by reacting a compound [VI] or its salt with a compound [III] or its salt.

Suitable salts of the compound [VI] can be referred to the ones as exemplified for the compound [I].

This reaction can be carried out in substantially the same manner as Process 1, and therefore the reaction mode and reaction condition of this reaction are to be referred to those explained in Process 1.

The object compound [I] and the starting compounds can also be prepared by the methods of Examples and Preparations mentioned below, similar manners thereto or to those described in EP-A-596,406 and EP-A-622,361, or conventional manners.

The compounds obtained by the above processes can be isolated and purified by a conventional method such as pulverization, recrystallization, chromatography, reprecipitation or the like.

It is to be noted that the compound [I] and the other compounds may include one or more stereoisomers and geometrical isomers due to asymmetric carbon atoms and double bonds, and all of such isomers and mixture thereof are included within the scop of this invention.

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral such as intravenous, intramuscular, subcutaneous or intraarticular, external such as topical, enteral, intrarectal, transvaginal, inhalant, ophthalmic, nasal of hypoglossal administration. The pharmaceutical preparations may be capsules, tablets, dragees, granules, suppositories, solution, lotion, suspension, emulsion, ointment, gel, cream, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for preventing and/or treating the above-mentioned diseases. In general, amounts between 0.1 mg/body and about 1,000 mg/body may be administered per day.

In order to illustrate the usefulness of the object compound [I], the pharmacological test data of some representative compounds of the compound [I] are shown in the following.

$^3$H-Bradykinin Receptor Binding (i) Test Method:

(a) Crude ileum membrane preparation

Male Hartly strain guinea pigs were sacrificed by decapitation. The ileum was removed and homogenized in buffer (50 mM trimethylaminoethanesulfonic acid (TES), 1 mM 1,10-phenanthroline pH 6.8). The homogenate was centrifuged (1000×g, 20 minutes) to remove tissue clumps and the supernatant was centrifuges (100,000×g, 60 minutes) to yield a pellet. The pellet was resuspended in buffer (50 mM TES, 1 mM 1,10-phenanthroline, 140 mg/l bacitracin, 1 mM dithiothreiol, 0.1% bovine serum albumin pH 6.8) and homogenized with a glass-teflon homogenizer to yield suspension which was referred to as crude membrane suspension. The obtained membrane suspension was stored at $-80°$ C. until use.

(b) $^3$H-Bradykinin Binding to the Membrane

The frozen crude membrane suspension was thawed. In binding assays, $^3$H-Bradykinin (0.06 nM) and drug ($1\times10^{-5}$ M) were incubated with 50 μl of the membrane suspension at room temperature for 60 minutes in a final volume of 250 μl. Separation of receptor-bound from free $^3$H-Bradykinin is achieved by immediate filtration under vacuum and washed three times with 5 ml of ice-cold buffer (50 mM Tris-HCl pH 7.5). Non-specific binding was defined as binding in the presence of 0.1 μM Bradykinin. The radioactivity retained on rinsed filters was determined by a liquid-scintillation counter.

(ii) Test Results

| Test Compound (Example No.) | Inhibition % of $^3$H-Bradykinin binding (concentration: $1 \times 10^{-5}$M) |
| --- | --- |
| 7 | 99 |
| 15-(9) hydrochloride | 94 |
| 15-(20) | 98 |

The effects of the compound [I] on bradykinin-induced bronchoconstriction and carrageenin-induced paw edema were measured according to similar manners described in British Journal of Pharmacology, 102, 774–777 (1991).

The object compound [I] and pharmaceutically acceptable salts thereof possess strong activities as bradykinin antagonists, and are useful for the treatment and/or the prevention of bradykinin or its analogues mediated diseases such as allergy, inflammation, autoimmune disease, shock, pain, or the like, and more particularly for the prevention and/or the treatment of asthma, cough, bronchitis, rhinitis, rhinorrhea, obstructive pulmonary disease [e.g. pulmonary emphysema, etc.], expectoration, pneumonitis, systemic inflammatory response syndrome (SIRS), septic shock, endotoxin shock, anaphylactic shock, adult respiratory distress syndrome, disseminated intravascular coagulopathy, arthritis, rheumatism, osteoarthritis, lumbago, inflammation-induced bone resorption, conjunctivitis, vernal conjunctivitis, uveitis, iritis, iridocyclitis, headache, migraine, toothache, backache, superficial pain, cancerous pain, postoperative pain, tenalgia, trauma [e.g. wound, burn, etc.], rash, erythema, eczema or dermatitis [e.g. contact dermatitis, atopic dermatitis, etc.], urticaria, herpes, itching, psoriasis, lichen, inflammatory bowel disease [e.g. ulcerative colitis, Crohn's disease, etc.], diarrhea, emesis, hepatitis, pancreatitis, gastritis, esophagitis, food allergy, ulcer, irritable bowel syndrome, nephritis, angina, periodontitis, edema, hereditary angioneurotic edema, cerebral edema, low blood pressure, thrombosis, myocardial infarction, cerebral vasospasm, congestion, coagulation, gout, central nervous system injury, premature labor, arteriosclerosis (hyperlipidemia, hypercholesterolemia), post-gastrectomy dumping syndrome, carcinoid syndrome, altered sperm mobility, diabetic neuropathy, neuralgia, graft rejection in transplantation, or the like, in human being or animals.

And further, it is known that bradykinin relates to the release of mediators such as prostaglandins, leukotrienes, tachykinins, histamine, thromboxanes, or the like, so the compound [I] is expected to be useful for the prevention and/or the treatment of such mediators mediated diseases.

EXAMPLES

The following Preparations and Examples are given for the purpose of illustrating this invention.

Preparation 1

(1) A suspension of 3-methoxy-2-nitrobenzoic acid (10.0 g), triethylamine (5.13 g) and diphenylphosphoryl azide (14 g) in benzene (100 ml) was refluxed for 40 minutes, and ethanol (2.57 g) was added thereto, and the mixture was refluxed for 30 minutes. After cooling, the solvent was removed in vacuo, and the residue was dissolved in ethyl acetate. Insoluble material was filtered off, and the filtrate was washed with saturated sodium bicarbonate solution, water and brine, dried over magnesium sulfate and evaporated in vacuo. The residue was purified by silica gel column chromatography (hexane:ethyl acetate=4:1, v/v) to give ethyl N-(3-methoxy-2-nitrophenyl)carbamate (7.23 g).

mp: 131–132° C.

NMR (CDCl$_3$, δ): 1.31 (3H, d, J=7.5 Hz), 3.90 (3H, s), 4.22 (2H, q, J=7.5 Hz), 6.73 (1H, d, J=7.5 Hz), 7.41 (1H, t, J=7.5 Hz), 7.71 (1H, br s), 7.78 (1H, d, J=7.5 Hz)

(2) To a suspension of lithium aluminum hydride (2.27 g) in tetrahydrofuran (50 ml) was added a suspension of ethyl N-(3-methoxy-2-nitrophenyl)carbamate (7.17 g) in tetrahydrofuran (15 ml) under ice-cooling, and the mixture was stirred for 1.5 hours at ambient temperature. Insoluble material was filtered off, and the filtrate was washed with water and brine, dried over magnesium sulfate and evaporated in vacuo. The residue was purified by silica gel column chromatography (hexane:ethyl acetate=3:1, v/v) to give 2-amino-3-methoxy-N-methylaniline (687 mg).

mp: 60–61° C.

NMR (CDCl$_3$, δ): 2.88 (3H, s), 3.40 (2H, br s), 3.84 (3H, s), 6.38 (1H, d, J=7.5 Hz), 6.42 (1H, d, J=7.5 Hz), 6.81 (1H, t, J=7.5 Hz)

(3) A suspension of 2-amino-3-methoxy-N-methylaniline (671 mg) and acetic acid (265 mg) in 4N hydrochloric acid (3.5 ml) was refluxed for 10 hours. Insoluble material was filtered off, and the filtrate was adjusted to pH 7 with saturated sodium bicarbonate solution, and extracted with dichloromethane. The organic layers were combined, washed with brine, dried over magnesium sulfate and evaporated in vacuo. The residue was purified by silica gel flash chromatography (dichloromethane:methanol=40:1, v/v) to give 1,2-dimethyl-4-methoxy-1H-benzimidazole (680 mg).

mp 122.5–124° C.

NMR (CDCl$_3$, δ): 2.59 (3H, s), 3.70 (3H, s), 4.00 (3H, s), 6.67 (1H, d, J=7.5 Hz), 6.89 (1H, d, J=7.5 Hz), 7.17 (1H, t, J=7.5 Hz)

(4) To a solution of 1,2-dimethyl-4-methoxy-1H-benzimidazole (560 mg) in dichloromethane (2 ml) was added 1M boron tribromide-dichloromethane solution (6.36 ml) under ice-cooling, and the mixture was stirred for 30 minutes at the same temperature and then for 2 hours at ambient temperature, and refluxed for 14 hours. After cooling, the solution was adjusted to pH 7 with saturated sodium bicarbonate solution, and extracted with dichloromethane twice. The organic layers were combined, washed with brine, dried over magnesium sulfate and evaporated in vacuo. The residue was crystallized with ethyl acetate to give 4-hydroxy-1,2-dimethyl-1H-benzimidazole (297 mg).

mp: 242.7–245° C.

NMR (CDCl$_3$, δ): 2.64 (3H, s), 3.69 (3H, s), 6.81 (2H, d, J=7.5 Hz), 7.17 (1H, t, J=7.5 Hz)

Preparation 2

(1) To a suspension of 3-hydroxy-2-nitrobenzoic acid (500 mg) and potassium carbonate (1.13 g) in dimethylformamide (5 ml) was added benzyl bromide (1.12 g) at ambient temperature, and the mixture was stirred overnight. To the reaction mixture was added water, and extracted with ethyl acetate twice. The organic layers were combined, washed with water and brine, dried over magnesium sulfate and evaporated in vacuo. The residue was purified by silica gel flash chromatography (hexane-ethyl acetate) and crystallized with diisopropyl ether to give benzyl 3-benzyloxy-2-nitrobenzoate (676 mg).

mp: 81.7–84.7° C.

NMR (CDCl$_3$, δ) 5.20 (2H, s), 5.32 (2H, s), 7.22–7.46 (12H, m), 7.61 (1H, d, J=7.5 Hz)

(2) To a suspension of benzyl 3-benzyloxy-2-nitrobenzoate (640 mg) in ethanol (5 ml) was added 1N sodium hydroxide solution (1.94 ml) at ambient temperature, and the mixture was stirred at 60° C. for 1 hour. The reaction mixture was adjusted to pH 4, and the resulting precipitates were collected by filtration and dried to give 3-benzyloxy-2-nitrobenzoic acid (439 mg).

mp: 198.4–200° C.

NMR (DMSO-d$_6$, δ): 5.30 (2H, s), 7.29–7.47 (5H, m), 7.51–7.70 (3H, m)

(3) tert-Butyl N-(3-benzyloxy-2-nitrophenyl)carbamate was obtained from 3-benzyloxy-2-nitrobenzoic acid, diphenylphosphoryl azide and tert-butanol according to a similar manner to that of Preparation 1-(1).

mp: 139.6–141° C.

NMR (CDCl$_3$, δ): 1.51 (9H, s), 5.18 (2H, s), 6.76 (1H, d, J=7.5 Hz), 7.29–7.45 (6H, m), 7.59 (1H, br s), 7.79 (1H, d, J=7.5 Hz)

Preparation 3

To a solution of tert-butyl N-(3-benzyloxy-2-nitrophenyl) carbamate (3 g) in dimethylformamide (30 ml) was added sodium hydride (60% in oil, 575 mg) under ice-cooling, and the mixture was stirred for 15 minutes. To the mixture was added ethyl iodide (1.49 g), and the mixture was stirred for 2 hours at ambient temperature. To the reaction mixture was added water (150 ml), and extracted with ethyl acetate. The organic layer was washed with water and brine, dried over magnesium sulfate and evaporated in vacuo. The residue was purified by silica gel column chromatography (hexane:ethyl acetate=5:1, v/v) and crystallized with hexane to give tert-butyl N-(3-benzyloxy-2-nitrophenyl)-N-ethylcarbamate (3.36 g).

mp: 86.7–92.9° C.

NMR (CDCl$_3$, δ): 1.17 (3H, t, J=7 Hz), 1.39 (9H, br s), 3.41–3.80 (2H, m), 15.19 (2H, s), 8.86 (1H, br d, J=7.5 Hz), 7.01 (1H, d, J=7.5 Hz), 7.29–7.32 (6H, m)

Preparation 4

The following compounds were obtained according to a similar manner to that of Preparation 3.

(1) tert-Butyl N-(3-benzyloxy-2-nitrophenyl)-N-methylcarbamate was obtained from tert-butyl N-(3-benzyloxy-2-nitrophenyl) carbamate and methyl iodide.

mp: 113–115° C.

NMR (CDCl$_3$, δ): 1.38 (9H, br s), 3.19 (3H, s), 5.19 (2H, s), 6.87 (1H, br d, J=8.5 Hz), 7.00 (1H, d, J=8.5 Hz), 7.31–7.43 (6H, m)

(2) tert-Butyl N-benzyl-N-(3-benzyloxy-2-nitrophenyl) carbamate was obtained from tert-butyl N-(3-benzyloxy-2-nitrophenyl)carbamate and benzyl bromide.

mp: 122.4° C.

NMR (CDCl$_3$, δ): 1.42 (9H, br s), 5.18 (2H, s), 6.97 (1H, d, J=7 Hz), 7.18 (1H, br t, J=7 Hz), 7.24–7.43 (11H, m)

Preparation 5

To tert-butyl N-(3-benzyloxy-2-nitrophenyl)-N-ethylcarbamate (3.30 g) was added 4N hydrogen chloride-ethyl acetate solution (15 ml) under ice-cooling, and the mixture was stirred for 10 minutes at the same temperature and then for 30 minutes at ambient temperature. The solvent was removed in vacuo, saturated sodium bicarbonate solution was added to the residue, and the mixture was extracted with ethyl acetate. The organic layer was washed with water and brine, dried over magnesium sulfate and evaporated in vacuo to give 3-benzyloxy-N-ethyl-2-nitroaniline (2.29 g).

NMR (CDCl$_3$, δ): 1.30 (3H, t, J=7 Hz), 3.13 (2H, q, J=7 Hz), 5.16 (2H, s), 6.31 (1H, d, J=7.5 Hz), 6.38 (1H, d, J=7.5 Hz), 7.21 (1H, t, J=7.5 Hz), 7.28–7.49 (5H, m)

Preparation 6

The following compounds were obtained according to a similar manner to that of Preparation 5.

(1) 3-Benzyloxy-N-methyl-2-nitroaniline mp: 80–81° C.

NMR (CDCl$_3$, δ): 2.91 (3H, d, J=7.0 Hz), 5.15 (2H, s), 6.21 (1H, br d, J=7.0 Hz), 6.33 (1H, d, J=8.5 Hz), 6.38 (1H, d, J=8.5 Hz), 7.25 (1H, t, J=8.5 Hz), 7.29–7.49 (5H, m)

(2) N-Benzyl-3-benzyloxy-2-nitroaniline mp: 91.5–93.7° C.

NMR (CDCl$_3$, δ): 4.42 (2H, d, J=6 Hz), 5.66 (2H, s), 6.33 (1H, d, J=7 Hz), 6.34 (1H, d, J=7 Hz), 6.47 (1H, br t, J=6 Hz), 7.15 (1H, t, J=7.5 Hz), 7.24–7.49 (10H, m)

Preparation 7

To a solution of 3-benzyloxy-N-ethyl-2-nitroaniline (2.20 g) and triethylamine (1.23 g) in dichloromethane (21 ml) was added acetyl chloride (698 mg) under ice-cooling, and the mixture was stirred for 3 hours at ambient temperature. The reaction mixture was washed with water, saturated sodium bicarbonate solution, water and brine successively, dried over magnesium sulfate and evaporated in vacuo. The residue was purified by silica gel flash chromatography (dichloromethane-ethyl acetate) to give N-acetyl-3-benzyloxy-N-ethyl-2-nitroaniline (1.71 g).

NMR (CDCl$_3$, δ): 1.15 (3H, t, J=7 Hz), 2.18 (3H, s), 3.16–4.10 (2H, m), 5.13 (2H, s), 6.90 (1H, d, J=7.5 Hz), 7.18 (1H, d, J=7.5 Hz), 7.33–7.50 (6H, m)

Preparation 8

The following compounds were obtained according to a similar manner to that of Preparation 7.

(1) 3-Benzyloxy-N-benzoyl-N-methyl-2-nitroaniline was obtained from 3-benzyloxy-N-methyl-2-nitroaniline and benzoyl chloride.

NMR (CDCl$_3$, δ): 3.37 (3H, s), 5.17 (2H, s), 6.60 (1H, br d, J=8.5 Hz), 6.93 (1H, d, J=8.5 Hz), 7.12–7.50 (11H, m)

(2) 3-Benzyloxy-N-methyl-2-nitro-N-propionylaniline was obtained from 3-benzyloxy-N-methyl-2-nitroaniline and propionyl chloride.

NMR (CDCl$_3$, δ) 0.91 (1H, t, J=7.5 Hz), 1.16 (2H, t, J=7.5 Hz), 1.95–2.22 (1.3H, m), 2.33–2.60 (0.7H, m), 3.15–3.27 (3H, m), 5.16–5.25 (2H, m), 6.83–6.94 (1H, m), 7.09–7.20 (1H, m), 7.30–7.53 (6H, m)

(3) N-Acetyl-N-benzyl-3-benzyloxy-2-nitroaniline was obtained from N-benzyl-3-benzyloxy-2-nitroaniline and acetyl chloride.

NMR (CDCl$_3$, δ): 1.92 (2H, s), 2.16 (1H, s), 3.22 (0.5H, d, J=15 Hz), 3.44 (0.5H, d, J=15 Hz), 3.98 (1H, d, J=15 Hz), 4.03 (1H, d, J=15 Hz), 5.19 (2H, s), 5.57 (0.5H, br s), 5.62 (0.5H, br s), 6.33 (0.6H, d, J=7.5 Hz), 6.38 (0.4H, d, J=7.5 Hz), 7.04–7.13 (1H, m), 7.17–7.45 (10H, m)

Preparation 9

To a solution of N-acetyl-3-benzyloxy-N-ethyl-2-nitroaniline (1.37 g) in acetic acid (11 ml) and ethanol (2.7 ml) was added iron (2.43 g), and the mixture was refluxed for 4 hours. Insoluble material was filtered off, and the filtrate was concentrated in vacuo. To the residue was added saturated sodium bicarbonate solution, and extracted with ethyl acetate. The organic layer was washed with saturated sodium bicarbonate solution, water and brine, dried over magnesium sulfate and evaporated in vacuo. The residue was purified by silica gel flash chromatography (hexane-ethyl acetate) to give 4-benzyloxy-1-ethyl-2-methyl-1H-benzimidazole (397 mg).

NMR (CDCl$_3$, δ): 1.40 (3H, t, J=7.5 Hz), 2.61 (3H, s), 4.13 (2H, q, J=7.5 Hz), 5.37 (2H, s), 6.67 (1H, d, J=7.5 Hz), 6.91 (1H, d, J=7.5 Hz), 7.09 (1H, t, J=7.5 Hz), 7.26–7.40 (3H, m), 7.51 (2H, br d, J=7.5 Hz)

Preparation 10

The following compounds were obtained according to a similar manner to that of Preparation 9.

(1) 4-Benzyloxy-1-methyl-2-phenyl-1H-benzimidazole mp: 118–120° C.

NMR (CDCl$_3$, δ): 3.85 (3H, s), 5.47 (2H, s), 6.73 (1H, d, J=7.5 Hz), 6.99 (1H, d, J=7.5 Hz), 7.17 (1H, t, J=7.5 Hz), 7.25–7.39 (3H, m), 7.48–7.57 (5H, m), 7.77–7.84 (2H, m)

(2) 4-Benzyloxy-2-ethyl-1-methyl-1H-benzimidazole mp: 94.9° C.

NMR (CDCl$_3$, δ) 1.43 (3H, t, J=7.5 Hz), 2.95 (2H, q, J=7.5 Hz), 3.70 (3H, s), 5.39 (2H, s), 6.65 (1H, d, J=8 Hz), 6.89 (1H, d, J=8 Hz), 7.09 (1H, t, J=8 Hz), 7.25–7.40 (3H, m), 7.51 (2H, d-like)

(3) 1-Benzyl-4-benzyloxy-2-methyl-1H-benzimidazole mp 128.5–136.8° C.

NMR (CDCl$_3$, δ): 2.56 (3H, s), 5.29 (2H, s), 5.37 (2H, s), 6.68 (1H, d, J=7.5 Hz), 6.83 (1H, d, J=7.5 Hz), 6.99–7.10 (3H, m), 7.24–7.44 (6H, m), 7.53 (2H, br d, J=9 Hz)

Preparation 11

To a solution of 4-benzyloxy-1-ethyl-2-methyl-1H-benzimidazole (370 mg) in ethyl acetate (3.7 ml) was added 10% palladium on carbon (18 mg), and the mixture was stirred for 5 hours at ambient temperature under hydrogen atmosphere. Insoluble material was filtered off, and the filtrate was concentrated in vacuo. The residue was crystallized with diisopropyl ether to give 1-ethyl-4-hydroxy-2-methyl-1H-benzimidazole (220 mg)

mp: 187–190° C.

NMR (CDCl$_3$, δ): 1.40 (3H, t, J=7.5 Hz), 2.68 (3H, s), 4.13 (2H, q, J=7.5 Hz), 6.81 (1H, d, J=7.5 Hz), 6.84 (1H, d, J=7.5 Hz), 7.17 (1H, t, J=7.5 Hz)

Preparation 12

The following compounds were obtained according to a similar manner to that of Preparation 11.

(1) 1-Methyl-4-hydroxy-2-phenyl-1H-benzimidazole mp: 210–211° C.

NMR (DMSO-d$_6$, δ): 3.82 (3H, s), 6.59 (1H, d, J=8.5 Hz), 7.00 (1H, d, J=8.5 Hz), 7.07 (1H, t, J=8.5 Hz), 7.50–7.62 (3H, m), 7.79–7.87 (2H, m)

(2) 2-Ethyl-4-hydroxy-1-methyl-1H-benzimidazole mp: 233.2° C.

NMR (CDCl$_3$, δ): 1.36 (3H, t, J=7.5 Hz), 2.98 (2H, q, J=7.5 Hz), 3.70 (3H, s), 6.77–6.86 (2H, m), 7.15 (1H, t, J=8 Hz)

(3) 1-Benzyl-4-hydroxy-2-methyl-1H-benzimidazole mp: 212.1° C.

NMR (CDCl$_3$, δ): 2.61 (3H, s), 5.28 (2H, s), 6.75 (1H, d, J=8 Hz), 6.80 (1H, d, J=8 Hz), 7.00–7.16 (2H, m), 7.11 (1H, t, J=8 Hz), 7.19–7.34 (3H, m)

Preparation 13

(1) To a solution of 2,6-dichloro-3-nitrobenzyl alcohol (5.0 g) in N,N-dimethylformamide (25 ml) were added imidazole (1.69 g) and tert-butyldiphenylsilyl chloride (6.0 ml) at ambient temperature with stirring. After 8 hours, the mixture was diluted with water (25 ml) and was extracted with ethyl acetate twice. The organic layer was washed with water and brine, dried over magnesium sulfate. The solvent was removed in vacuo to give 1-(tert-butyldiphenylsilyloxy-methyl)-2,6-dichloro-3-nitrobenzene (11.5 g) as an oil.

NMR (CDCl$_3$, δ): 1.05 (9H, s), 4.96 (2H, s), 7.27–7.51 (7H, m), 7.58–7.81 (5H, m)

(2) To a stirred mixture of 1-(tert-butyldiphenylsilyloxy-methyl)-2,6-dichloro-3-nitrobenzene (433 mg), ferric chloride hexahydrate (17.5 mg) and activated carbon (17.5 mg) in a mixture of methanol (2.78 ml) and water (0.69 ml) was added hydrazine monohydrate (0.135 ml) dropwise at 60–70° C. After the addition was finished, the mixture was refluxed for half an hour. The mixture was allowed to cool and filtered. The filtrate was concentrated in vacuo. The residue was extracted with dichloromethane and the organic phase was dried over anhydrous magnesium sulfate. After being filtered, the filtlate was concentrated in vacuo and the resulting residue was washed with n-hexane to give 3-amino-1-(tert-butyldiphenylsilyloxymethyl)-2,6-dichlorobenzene (348 mg) as a white mass.

NMR (CDCl$_3$, δ): 1.05 (9H, s), 4.07 (2H, br s), 4.87 (2H, s), 6.66 (1H, d, J=9 Hz), 7.08 (1H, d, J=9 Hz), 7.30–7.50 (6H, m), 7.70–7.84 (4H, m)

(3) To a mixture of 3-amino-1-(tert-butyldiphenylsilyloxy-methyl)-2,6-dichlorobenzene (348 mg) triethylamine (0.15 ml) and dichloromethane (3.5 ml) was added phthalimidoacetyl chloride (186 mg) under ice-cooling, and the mixture was stirred for 1.5 hours at ambient temperature. Water was added thereto, and the resulting precipitates were collected by vacuum filtration and washed with diisopropyl ether to give 1-(tert-butyldiphenylsilyloxymethyl)-2,6-dichloro-3-(phthalimidoacetylamino)benzene (460 mg) as crystals.

mp: 198.1° C.

NMR (CDCl$_3$, δ): 1.04 (9H, s), 4.57 (2H, s), 4.90 (2H, s), 7.25–7.50 (7H, m), 7.55–7.83 (6H, m), 7.85–8.07 (2H, m), 8.00 (1H, br s), 8.25 (1H, d, J=8 Hz)

(4) To a mixture of 1-(tert-butyldiphenylsilyloxymethyl)-2,6-dichloro-3-(phthalimidoacetylamino)benzene (453 mg) and N,N-dimethylformamide (2.2 ml) was added sodium hydride (60% in oil, 31 mg) under ice-cooling, and the mixture was stirred for 50 minutes. To the mixture was added methyl iodide (0.055 ml), and the mixture was stirred for 2.5 hours at ambient temperature. Water (88 ml) was added to the mixture under ice-cooling, and the resulting precipitates were collected by vacuum filtration and washed with water and ethyl acetate to give 1-(tert-butyldiphenylsilyloxymethyl)-2,6-dichloro-3-[N-methyl-N-(phthalimidoacetyl)amino]benzene (236 mg) as powder.

mp: 167–172° C.

NMR (CDCl$_3$, δ): 1.06 (9H, s), 3.20 (3H, s), 4.04 (2H, s), 4.98 (2H, s), 7.31–7.51 (9H, m), 7.65–7.79 (6H, m), 7.80–7.92 (2H, m)

(5) To a solution of 1-(tert-butyldiphenylsilyloxymethyl)-2,6-dichloro-3-[N-methyl-N-(phthalimidoacetyl)amino]benzene (119 mg) in tetrahydrofuran (0.6 ml) was added 1M tetrabutylammonium fluoride-tetrahydrofuran (0.4 ml) under ice-cooling, and the mixture was stirred for 1.5 hours at ambient temperature. The mixture was partitioned between ethyl acetate and water. The organic layer was concentrated in vacuo.

The resulting precipitates were collected by filtration and washed with methanol to give 2,6-dichloro-1-hydroxymethyl-3-[N-methyl-N-(phthalimidoacetyl)amino]benzene (43 mg) as powder.

mp 236.2–240.8° C.

NMR (CDCl$_3$, δ): 2.24 (1H, t, J=7 Hz), 3.21 (3H, s), 4.09 (2H, s), 5.04 (2H, d, J=7 Hz), 7.43 (1H, d, J=8 Hz), 7.48 (1H, d, J=8 Hz), 7.67–7.75 (2H, m), 7.80–7.88 (2H, m)

(6) To a mixture of 2,6-dichloro-1-hydroxymethyl-3-[N-methyl-N-(phthalimidoacetyl) amino]benzene (399 mg) and triethylamine (0.17 ml) in methylene chloride (8 ml) was added methanesulfonyl chloride (0.086 ml) under −20° C., and the mixture was stirred for 1 hour. The mixture was washed with sodium bicarbonate solution and brine, dried over magnesium sulfate and concentrated in vacuo to give 2,6-dichloro-1-methylsulfonyloxymethyl-3-[N-methyl-N-(phthalimidoacetyl)amino]benzene (561 mg).

NMR (CDCl$_3$, δ): 3.15 (3H, s), 3.24 (3H, s), 4.09 (2H, s), 5.48 (2H, s), 7.56 (2H, s), 7.67–7.78 (2H, m), 7.80–7.93 (2H, m)

Example 1

To a suspension of 4-hydroxy-1,2-dimethyl-1H-benzimidazole (250 mg) in N,N-dimethylformamide (2.5 ml) was added sodium hydride (60% in oil, 102 mg) under ice-cooling, and the mixture was stirred for 15 minutes at ambient temperature. To the mixture was added 2,6-dichloro-1-methylsulfonyloxymethyl-3-[N-methyl-N-(phthalimidoacetyl)-amino]benzene (799 mg), and the mixture was stirred for 3 hours at ambient temperature. Water was dropwise added thereto, and the resulting precipitates were collected by filtration to give 4-[2,6-dichloro-3-[N-(phthalimidoacetyl)-N-methylamino]benzyloxy]-1,2-dimethyl-1H-benzimidazole (418 mg).

mp: 225.6–227° C.

NMR (CDCl$_3$, δ): 2.59 (3H, s), 3.23 (3H, s), 3.71 (3H, s), 4.11 (2H, s), 5.60 (2H, s), 6.85 (1H, d, J=7.5 Hz), 6.98 (1H, d, J=7.5 Hz), 7.21 (1H, t, J=7.5 Hz), 7.48 (1H, d, J=8 Hz), 7.52 (1H, d, J=8 Hz), 7.69–7.77 (2H), 7.82–7.90 (2H)

Example 2

The following compounds were obtained according to a similar manner to that of Example 1.

(1) 4-[2,6-Dichloro-3-[N-(phthalimidoacetyl)-N-methylamino]-benzyloxy]-2-methylbenzoxazole was obtained from 4-hydroxy-2-methylbenzoxazole and 2,6-dichloro-1-methylsulfonyloxymethyl-3-[N-methyl-N-(phthalimidoacetyl) amino]benzene.

mp 204.7–206.5° C.

NMR (CDCl$_3$, δ): 2.62 (3H, s), 3.24 (3H, s), 4.12 (2H, s), 5.63 (2H, s), 6.94 (1H, d, J=7.5 Hz), 7.18 (1H, d, J=7.5 Hz), 7.23–7.31 (1H, overlapped with CDCl$_3$), 7.50 (1H, d, J=8 Hz), 7.54 (1H, t, J=8 Hz), 7.69–7.77 (2H), 7.82–7.89 (2H)

(2) 4-[2,6-Dichloro-3-[N-(phthalimidoacetyl)-N-methylamino]benzyloxy]-1-ethyl-2-methyl-1H-benzimidazole mp: 233–236° C.

NMR (CDCl$_3$, δ): 1.40 (3H, t, J=7.5 Hz), 2.59 (3H, s), 3.24 (3H, s), 4.09–4.20 (4H, m), 5.60 (2H, s), 6.85 (1H, d, J=7.5 Hz), 6.99 (1H, d, J=7.5 Hz), 7.21 (1H, t, J=7.5 Hz), 7.48 (1H, d, J=8 Hz), 7.51 (1H, d, J=8 Hz), 7.69–7.77 (2H, m), 7.83–7.89 (2H, m)

(3) 4-[2,6-Dichloro-3-[N-(phthalimidoacetyl)-N-methylamino]-benzyloxy]-1-methyl-2-phenyl-1H-benzimidazole mp: 154–156° C.

NMR (CDCl$_3$, δ): 3.21 (3H, s), 3.83 (3H, s), 4.09 (2H, s), 5.71 (2H, s), 6.91 (1H, d, J=7.5 Hz), 7.08 (1H, d, J=7.5 Hz), 7.27 (1H, t, J=7.5 Hz), 7.43–7.53 (5H, m), 7.66–7.77 (4H, m), 7.80–7.89 (2H, m)

(4) 4-[2,6-Dichloro-3-[N-(phthalimidoacetyl)-N-methylamino]-benzyloxy]-2-ethyl-1-methyl-1H-benzimidazole mp: 108.1° C.

NMR (CDCl$_3$, δ): 1.37 (3H, t, J=7.5 Hz), 2.93 (2H, q, J=7.5 Hz), 3.24 (3H, s), 3.73 (3H, s), 4.10 (2H, s), 5.63 (2H, s), 6.85 (1H, d, J=8 Hz), 6.97 (1H, d, J=8 Hz), 7.19 (1H, t, J=8 Hz), 7.46 (1H, d, J=8 Hz), 7.52 (1H, d, J=8 Hz), 7.67–7.75 (2H, m), 7.80–7.90 (2H, m)

(5) 4-[2,6-Dichloro-3-[N-(phthalimidoacetyl)-N-methylamino]-benzyloxy]-1-benzyl-2-methyl-1H-benzimidazole NMR (CDCl$_3$, δ): 2.54 (3H, s), 3.24 (3H, s), 4.14 (2H, s), 5.30 (2H, s), 5.60 (2H, s), 6.85 (1H, d, J=7.5 Hz), 6.93 (1H, d, J=7.5 Hz), 7.03–7.10 (2H, m), 7.17 (1H, t, J=7.5 Hz), 7.24–7.36 (3H, m), 7.47 (1H, d, J=8 Hz), 7.51 (1H, d, J=8 Hz), 7.68–7.75 (2H, m), 7.80–7.90 (2H, m)

Example 3

A mixture of 4-[2,6-dichloro-3-[N-(phthalimidoacetyl)-N-methylamino]benzyloxy]-1,2-dimethyl-1H-benzimidazole (405 mg), hydrazine monohydrate (75.4 mg) and ethanol (4.0 ml) was refluxed for 30 minutes. After cooling, the resulting precipitate was filtered off, and the filtrate was concentrated in vacuo to give 4-[3-(N-glycyl-N-methylamino)-2,6-dichlorobenzyloxy]-1,2-dimethyl-1H-benzimidazole (300 mg).

NMR (CDCl$_3$, δ): 2.59 (3H, s), 3.02 (1H, d, J=17 Hz), 3.12 (1H, d, J=17 Hz), 3.22 (3H, s), 3.71 (3H, s), 5.52 (1H, d, J=10 Hz), 5.58 (1H, d, J=10 Hz), 6.82 (1H, d,

J=7.5 Hz), 6.97 (1H, d, J=7.5 Hz), 7.20 (1H, t, J=7.5 Hz), 7.23 (1H, d, J=8 Hz), 7.43 (1H, d, J=8 Hz)

Example 4

The following compounds were obtained according to a similar manner to that of Example 3.

(1) 4-[3-(N-Glycyl-N-methylamino)-2,6-dichlorobenzyloxy]-2-methylbenzoxazole

NMR (CDCl$_3$, δ): 2.61 (3H, s), 3.02 (1H, d, J=17 Hz), 3.12 (1H, d, J=17 Hz), 3.22 (3H, s), 5.57 (1H, d, J=10 Hz), 5.61 (1H, d, J=10 Hz), 6.92 (1H, d, J=7.5 Hz), 7.17 (1H, d, J=7.5 Hz), 7.22–7.30 (2H, m), 7.46 (1H, d, J=7.5 Hz)

(2) 4-[3-(N-Glycyl-N-methylamino)-2,6-dichlorobenzyloxy]-1-ethyl-2-methyl-1H-benzimidazole NMR (CDCl$_3$, δ): 1.40 (3H, t, J=7.5 Hz), 2.59 (3H, s), 3.02 (1H, d, J=17 Hz), 3.12 (1H, d, J=17 Hz), 3.22 (3H, s), 4.14 (2H, d, J=7.5 Hz), 5.52 (1H, d, J=10 Hz), 5.58 (1H, d, J=10 Hz), 6.83 (1H, d, J=7.5 Hz), 6.98 (1H, d, J=7.5 Hz), 7.17–7.28 (2H, m), 7.43 (1H, d, J=8 Hz)

(3) 4-[3-(N-Glycyl-N-methylamino)-2,6-dichlorobenzyloxy]-1-methyl-2-phenyl-1H-benzimidazole NMR (CDCl$_3$, δ): 3.02 (1H, d, J=16.5 Hz), 3.12 (1H, d, J=16.5 Hz), 3.22 (3H, s), 3.84 (3H, s), 5.65 (1H, d, J=9.0 Hz), 5.70 (1H, d, J=9.0 Hz), 6.89 (1H, d, J=7.5 Hz), 7.07 (1H, d, J=7.5 Hz), 7.23 (1H, d, J=7.5 Hz), 7.29 (1H, t, J=7.5 Hz), 7.43 (1H, d, J=7.5 Hz), 7.47–7.53 (3H, m), 7.70–7.78 (2H, m)

(4) 4-[3-(N-Glycyl-N-methylamino)-2,6-dichlorobenzyloxy]-2-ethyl-1-methyl-1H-benzimidazole NMR (CDCl$_3$, δ) 1.36 (3H, t, J=7.5 Hz), 2.93 (2H, q, J=7.5 Hz), 3.03 (1H, d, J=18 Hz), 3.11 (1H, d, J=18 Hz), 3.23 (3H, s), 3.73 (3H, s), 5.53–5.65 (2H, m), 6.84 (1H, d, J=8 Hz), 6.97 (1H, d, J=8 Hz), 7.15–7.28 (2H, m), 7.45 (1H, d, J=8 Hz)

(5) 4-[3-(N-Glycyl-N-methylamino)-2,6-dichlorobenzyloxy]-1-benzyl-2-methyl-1H-benzimidazole NMR (CDCl$_3$, δ): 1.77 (2H, br s), 2.55 (3H, s), 3.03 (1H, d, J=17 Hz), 3.10 (1H, d, J=17 Hz), 3.21 (3H, s), 5.30 (2H, s), 5.54 (1H, d, J=9 Hz), 5.59 (1H, d, J=9 Hz), 6.83 (1H, d, J=7 Hz), 6.90 (1H, d, J=7 Hz), 7.00–7.10 (2H, m), 7.16 (1H, t, J=7 Hz), 7.20–7.35 (4H, m), 7.43 (1H, d, J=7 Hz)

Example 5

To a solution of 4-[3-(N-glycyl-N-methylamino)-2,6-dichlorobenzyloxy]-1,2-dimethyl-1H-benzimidazole (80 mg) in dichloromethane (0.8 ml) were added pyridine (23.3 mg) and acetic anhydride (30.1 mg) at ambient temperature, and the mixture was stirred for 1 hour at the same temperature. The solvent was removed with toluene azeotropically three times. The residue was purified by preparative thin layer chromatography (dichloromethane:methanol=10:1, v/v) to give 4-[3-[N-(acetylglycyl)-N-methylamino]-2,6-dichlorobenzyloxy]-1,2-dimethyl-1H-benzimidazole (75 mg).

NMR (CDCl$_3$, δ): 2.01 (3H, s), 2.58 (3H, s), 3.24 (3H, s), 3.52 (1H, dd, J=17, 4 Hz), 3.71 (3H, s), 3.80 (1H, dd, J=17, 5 Hz), 5.51 (1H, d, J=10 Hz), 5.58 (1H, d, J=10 Hz), 6.42 (1H, br s), 6.86 (1H, d, J=7.5 Hz), 6.98 (1H, d, J=7.5 Hz), 7.18–7.29 (2H, m), 7.47 (1H, d, J=7.5 Hz)

Example 6

4-[3-[N-(Acetylglycyl)-N-methylamino]-2,6-dichlorobenzyloxy]-2-methylbenzoxazole was obtained according to a similar manner to that of Example 5.

NMR (CDCl$_3$, δ): 2.01 (3H, s), 2.61 (3H, s), 3.24 (3H, s), 3.51 (1H, dd, J=17, 4 Hz), 3.80 (1H, dd, J=17, 4 Hz), 5.55 (1H, d, J=10 Hz), 5.60 (1H, d, J=10 Hz), 6.42 (1H, br s), 6.92 (1H, d, J=7.5 Hz), 7.16 (1H, d, J=7.5 Hz), 7.22–7.31 (2H, m), 7.48 (1H, d, J=7.5 Hz)

Example 7

To a mixture of 4-[3-(N-glycyl-N-methylamino)-2,6-dichlorobenzyloxy]-1,2-dimethyl-1H-benzimidazole (100 mg), 4-(methylcarbamoyl)cinnamic acid (55.4 mg) and dimethylformamide (1 ml) were added 1-ethyl-3-(3-dimethylaminopropyl)carbodiimide hydrochloride (61.2 mg) and 1-hydroxybenzotriazole (49.7 mg), and the mixture was stirred for 3 hours at ambient temperature. To the mixture was added water, and the mixture was extracted with dichloromethane. The separated organic layer was washed with saturated sodium bicarbonate solution and brine, dried over magnesium sulfate and evaporated in vacuo. The residue was purified by preparative thin layer chromatography (dichloromethane-methanol) to give 4-[2,6-dichloro-3-[N-methyl-N-[4-(methyl-carbamoyl)cinnamoylglycyl]amino]benzyloxy]]-1,2-dimethyl-1H-benzimidazole (121 mg).

NMR (CDCl$_3$, δ): 2.58 (3H, s), 3.02 (3H, d, J=5 Hz), 3.28 (3H, s), 3.61–3.72 (4H), 3.93 (1H, dd, J=17, 5 Hz), 5.52 (1H, d, J=10 Hz), 5.58 (1H, d, J=10 Hz), 6.20 (1H, br d, J=5 Hz), 6.52 (1H, d, J=15 Hz), 6.70 (1H, br s), 6.88 (1H, d, J=7.5 Hz), 6.98 (1H, d, J=7.5 Hz), 7.22 (1H, t, J=7.5 Hz), 7.30 (1H, d, J=8 Hz), 7.48 (1H, d, J=8 Hz), 7.51–7.62 (3H), 7.77 (2H, d, J=7.5 Hz)

Example 8

The following compounds were obtained according to a similar manner to that of Example 7.

(1) 4-[2,6-Dichloro-3-[N-methyl-N-[4-(methylcarbamoyl)-cinnamoylglycyl]amino]benzyloxy]-2-methylbenzoxazole NMR (CDCl$_3$, δ): 2.61 (3H, s), 3.02 (3H, d, J=5 Hz), 3.28 (3H, s), 3.67 (1H, dd, J=17, 4 Hz), 3.94 (1H, dd, J=17, 5 Hz), 5.58 (1H, d, J=10 Hz), 5.61 (1H, d, J=10 Hz), 6.15 (1H, br d, J=5 Hz), 6.52 (1H, d, J=15 Hz), 6.68 (1H, br s), 6.93 (1H, d, J=7.5 Hz), 7.16 (1H, d, J=7.5 Hz), 7.21–7.35 (3H), 7.46–7.62 (3H), 7.76 (2H, d, J=7.5 Hz)

(2) 4-[2,6-Dichloro-3-[N-methyl-N-[4-(methylcarbamoyl)-cinnamoylglycyl]amino]benzyloxy]-1-ethyl-2-methyl-1H-benzimidazole NMR (CDCl$_3$, δ) 1.40 (3H, t, J=7 Hz), 2.58 (3H, s), 3.02 (3H, d, J=5 Hz), 3.28 (3H, s), 3.68 (1H, dd, J=17, 4 Hz), 3.94 (1H, dd, J=17, 5 Hz), 5.52 (1H, d, J=10 Hz), 5.58 (1H, d, J=10 Hz), 6.20 (1H, br d, J=5 Hz), 6.52 (1H, d, J=15 Hz), 6.70 (1H, br t, J=5 Hz), 6.86 (1H, d, J=7.5 Hz), 6.99 (1H, d, J=7.5 Hz), 7.22 (1H, t, J=7.5 Hz), 7.31 (1H, d, J=8 Hz), 7.48 (1H, d, J=8 Hz), 7.51–7.62 (3H), 7.76 (2H, d, J=7.5 Hz)

(3) 4-[2,6-Dichloro-3-[N-methyl-N-[4-(methylcarbamoyl)-cinnamoylglycyl]amino]benzyloxy]-1-methyl-2-phenyl-1H-benzimidazole NMR (CDCl$_3$, δ): 2.98 (3H, d, J=4.5 Hz), 3.25 (3H, s), 3.66 (1H, dd, J=16.5, 4.5 Hz), 3.82 (3H, s), 3.93 (1H, dd, J=16.5, 4.5 Hz), 5.66 (2H, s), 6.24 (1H, br q, J=4.5 Hz), 6.51 (1H, d, J=16.0 Hz), 6.71 (1H, br t, J=4.5 Hz), 6.93 (1H, d, J=7.5 Hz), 7.08 (1H, d, J=7.5 Hz), 7.25–7.34 (2H, m), 7.43–7.61 (7H, m), 7.68–7.79 (4H, m)

its hydrochloride mp: 178–191° C.

NMR (DMSO-$d_6$, δ): 2.80 (3H, d, J=4.5 Hz), 3.16 (3H, s), 3.53 (1H, dd, J=16.0, 5.5 Hz), 3.82 (1H, dd, J=16.0, 5.5 Hz), 3.97 (3H, s), 5.58 (1H, d, J=10.0 Hz), 5.62 (1H, d, J=10.0 Hz), 6.89 (1H, d, J=16.0 Hz), 7.41 (1H, d, J=16.0 Hz), 7.37–7.49 (1H, m), 7.60–7.73 (7H, m), 7.81–7.94 (6H, m), 8.37 (1H, t, J=5.5 Hz), 8.52 (1H, q, J=4.5 Hz)

(4) 4-[2,6-Dichloro-3-[N-methyl-N-[4-(methylcarbamoyl)-cinnamoylglycyl]amino]benzyloxy]-2-ethyl-1-methyl-1H-benzimidazole NMR (CDCl$_3$, δ): 1.36 (3H, t, J=7.5 Hz), 2.93 (2H, q, J=7.5 Hz), 3.02 (3H, d, J=4.5 Hz), 3.27 (3H, s), 3.66 (1H, dd, J=4, 18 Hz), 3.73 (3H, s), 3.93 (1H, dd, J=4, 18 Hz), 5.53–5.64 (2H, m), 6.17 (1H, q-like), 6.52 (1H, d, J=16 Hz), 6.68 (1H, t-like), 6.86 (1H, d, J=8 Hz), 6.98 (1H, d, J=8 Hz), 7.21 (1H, t, J=8 Hz), 7.30 (1H, d, J=8 Hz), 7.46 (1H, d, J=8 Hz), 7.54 (2H, d, J=8 Hz), 7.59 (1H, d, J=16 Hz), 7.75 (2H, d, J=8 Hz)

its hydrochloride

NMR (DMSO-$d_6$, δ): 1.27–1.37 (3H, m), 2.78 (3H, d, J=4.5 Hz), 3.12 (2H, q, J=7.5 Hz), 3.15 (3H, s), 3.84 (1H, dd, J=4.5, 16 Hz), 3.95 (3H, s), 5.53 (1H, d, J=10 Hz), 5.60 (1H, d, J=10 Hz), 6.86–6.97 (1H, m), 7.37–7.49 (2H, m), 7.49–7.78 (4H, m), 7.78–7.91 (4H, m), 8.38 (1H, t-like), 8.52 (1H, q-like)

(5) 4-[2,6-Dichloro-3-[N-methyl-N-[4-(methylcarbamoyl)-cinnamoylglycyl]amino]benzyloxy]-1-benzyl-2-methyl-1H-benzimidazole NMR (CDCl$_3$, δ): 2.54 (3H, s), 3.00 (3H, d, J=5 Hz), 3.27 (3H, s), 3.66 (1H, dd, J=17, 4 Hz), 3.94 (1H, dd, J=17, 5 Hz), 5.30 (2H, s), 5.53 (1H, d, J=9 Hz), 5.58 (1H, d, J=9 Hz), 6.26 (1H, br q, J=5 Hz), 6.50 (1H, d, J=15 Hz), 6.70 (1H, t, J=5 Hz), 6.86 (1H, d, J=7 Hz), 6.91 (1H, d, J=7 Hz), 7.02–7.10 (2H, m), 7.17 (1H, t, J=7 Hz), 7.24–7.36 (4H, m), 7.44–7.61 (4H, m), 7.70–7.79 (2H, m)

its hydrochloride

NMR (CDCl$_3$—CD$_3$OD, δ) 2.89 (3H, s), 2.95 (3H, s), 3.27 (3H, s), 3.77 (1H, d, J=17 Hz), 3.88 (1H, d, J=17 Hz), 5.51 (1H, d, J=9 Hz), 5.58 (2H, br s), 5.60 (1H, d, J=9 Hz), 6.65 (1H, d, J=15 Hz), 7.10–7.25 (4H, m), 7.32–7.41 (2H, m), 7.45–7.60 (7H, m), 7.76 (2H, d, J=9 Hz)

Preparation 14

(1) To a solution of 2-amino-3-nitrophenol (10 g) in dimethylformamide (100 ml) was added potassium carbonate (17.9 g) under ice-cooling, and the mixture was stirred for 30 minutes at the same temperature. To the mixture was added 4-methoxybenzyl chloride (10.7 g) at ambient temperature, and the mixture was stirred for 30 minutes under ice-cooling and then overnight at ambient temperature. To the reaction mixture was added water, and the mixture was extracted with dichloromethane, and purified by silica gel column chromatography (ethyl acetate-n-hexane). The residue was crystallized with ethanol to give 2-(4-methoxybenzyloxy)-6-nitroaniline (13.6 mg) as yellow needles.

mp: 103° C.

NMR (CDCl$_3$, δ): 3.84 (3H, s), 5.04 (2H, s), 6.43 (2H, br s), 6.59 (1H, t, J=8 Hz), 6.87–7.01 (3H, m), 7.28–7.40 (2H, br d, J=9 Hz), 7.74 (1H, d, J=8 Hz)

(2) To a solution of 2-(4-methoxybenzyloxy)-6-nitroaniline (3 g) in acetic acid (6 ml) and ethanol (24 ml) was added iron (3.06 g), and the mixture was refluxed for 3 hours. Insoluble material was filtered off, and the filtrate was concentrated in vacuo. To the residue was added saturated sodium bicarbonate solution, and extracted with ethyl acetate. The organic layer was dried over magnesium sulfate and evaporated in vacuo. The residue was pulverized with diethyl ether to give 2-amino-3-(4-methoxybenzyloxy) aniline (2.25 g).

mp: 127.1° C.

NMR (CDCl$_3$, δ): 3.43 (4H, br s), 3.81 (3H, s), 4.98 (2H, s), 6.40 (1H, d, J=8 Hz), 6.48 (1H, d, J=8 Hz), 6.66 (1H, t, J=8 Hz), 6.91 (2H, d, J=9 Hz), 7.35 (2H, d, J=9 Hz)

(3) To a stirred solution of 2-amino-3-(4-methoxybenzyloxy)-aniline (1.15 g) in acetic acid (12 ml) was added triethyl orthopropionate (994 mg) at ambient temperature, and the mixture was stirred overnight. The reaction mixture was concentrated in vacuo, and the residue was extracted with dichloromethane. The organic layer was washed with saturated sodium bicarbonate solution and brine, dried over magnesium sulfate and evaporated in vacuo to give 2-ethyl-4-(4-methoxybenzyloxy)-1H-benzimidazole (900 mg) as pale yellow powder.

mp: 73.8–77.9° C.

NMR (CDCl$_3$, δ): 1.40 (3H, t, J=7.5 Hz), 2.91 (2H, q, J=7.5 Hz), 3.82 (3H, br s), 5.00–5.35 (2H, m), 6.57–7.20 (4H, m), 7.26–7.43 (1H, m), 7.38 (2H, d, J=9 Hz), 9.11–9.52 (1H, m)

(4) A solution of 2-ethyl-4-(4-methoxybenzyloxy)-1H-benzimidazole (282 mg), ethyl bromoacetate (184 mg) and potassium carbonate (414 mg) in dimethylformamide (3 ml) was stirred for 2 hours, and to the reaction mixture were added ethyl acetate and water. The separated organic layer was washed with brine, dried over magnesium sulfate and evaporated in vacuo. The residue was purified by flash chromatography (ethyl acetate:n-hexane=1:2 to 2:1, v/v) to give 1-ethoxycarbonylmethyl-2-ethyl-4-(4-methoxybenzyloxy)-1H-benzimidazole (245 mg) as white powder.

mp: 112.1° C.

NMR (CDCl$_3$, δ): 1.25 (3H, t, J=7.5 Hz), 1.42 (3H, t, J=7.5 Hz), 2.86 (2H, q, J=7.5 Hz), 3.80 (3H, s), 4.20 (2H, q, J=7.5 Hz), 4.78 (2H, s), 5.30 (2H, s), 6.18 (1H, d, J=7.5 Hz), 6.29 (1H, d, J=7.5 Hz), 6.38 (2H, d, J=9 Hz), 7.08 (1H, t, J=7.5 Hz), 7.42 (2H, d, J=9 Hz)

(5) 1-Ethoxycarbonylmethyl-2-ethyl-4-hydroxy-1H-benzimidazole was obtained according to a similar manner to that of Preparation 11.

mp: 148.2–150.5° C.

NMR (CDCl$_3$, δ): 1.25 (3H, t, J=7.5 Hz), 1.36 (3H, t, J=7.5 Hz), 2.90 (2H, q, J=7.5 Hz), 4.22 (2H, q, J=7.5 Hz), 4.78 (2H, s), 6.73 (1H, d, J=8 Hz), 6.79 (1H, d, J=8 Hz), 7.14 (1H, t, J=8 Hz)

Preparation 15

(1) To a mixture of 3-benzyloxy-N-methyl-2-nitroaniline (453.3 mg), 80% methanol (6.8 ml), anhydrous ferric chloride (13.6 mg) and carbon (13.6 mg) was dropwise added hydrazine monohydrate (255.6 μl), and the mixture was stirred for 5 hours at ambient temperature. Insoluble material was filtered off, and the filtrate was concentrated in vacuo. To the residue were added ethyl acetate and saturated sodium bicarbonate solution, and the separated organic layer was washed with water and brine, dried over magnesium sulfate and evaporated in vacuo. The residue was purified by silica gel column chromatography (ethyl acetate-n-hexane) to give 2-amino-3-benzyloxy-N-methylaniline (348.9 mg).

mp: 79–81° C.

NMR (CDCl₃, δ): 2.87 (3H, s), 3.43 (3H, br s), 5.07 (2H, s), 6.40 (1H, d, J=7.5 Hz), 6.49 (1H, d, J=7.5 Hz), 6.80 (1H, t, J=7.5 Hz), 7.29–7.47 (5H, m)

(2) To a solution of 2-amino-3-benzyloxy-N-methylaniline (318.5 mg) in acetic acid (3.2 ml) was added tetramethyl orthocarbonate (233 µl) at ambient temperature, and the mixture was stirred for 4 hours. The reaction mixture was concentrated in vacuo, and to the residue were added ethyl acetate and saturated sodium bicarbonate solution. The separated organic layer was washed with water and brine, and dried over magnesium sulfate. The solvent was removed in vacuo to give 4-benzyloxy-2-methoxy-1-methyl-1H-benzimidazole (273.3 mg).

mp: 98–102° C.

NMR (CDCl₃, δ): 3.53 (3H, s), 4.22 (3H, s), 5.40 (2H, s), 6.63 (1H, d, J=7.5 Hz), 6.77 (1H, d, J=7.5 Hz), 6.99 (1H, t, J=7.5 Hz), 7.22–7.41 (3H, m), 7.45–7.52 (2H, m)

(3) 4-Hydroxy-2-methoxy-1-methyl-1H-benzimidazole was obtained according to a similar manner to that of Preparation 11.

mp: 226–229° C.

NMR (DMSO-d₆, δ): 3.48 (3H, s), 4.08 (3H, s), 6.49 (1H, d, J=7.5 Hz), 6.76 (1H, d, J=7.5 Hz), 6.88 (1H, t, J=7.5 Hz), 9.39 (1H, br s)

Preparation 16

(1) 3-(N-Glycyl-N-methylamino)-1-(tert-butyldiphenylsilyloxymethyl)-2,6-dichlorobenzene was obtained from 1-(tert-butyldiphenylsilyloxymethyl)-2,6-dichloro-3-[N-methyl-N-(phthalimidoacetyl)amino]benzene according to a similar manner to that of Example 3.

NMR (CDCl₃, δ): 1.05 (9H, s), 2.94 (1H, d, J=17 Hz), 3.09 (1H, d, J=17 Hz), 3.20 (3H, s), 4.93 (2H, s), 7.18 (1H, d, J=8 Hz), 7.35–7.49 (7H, m), 6.69–7.77 (4H, m)

(2) 1-(tert-Butyldiphenylsilyloxymethyl)-2,6-dichloro-3-[N-methyl-N-[4-(methylcarbamoyl)cinnamoylglycyl]amino]benzene was obtained by reacting 3-(N-glycyl-N-methylamino)-1-(tert-butyldiphenylsilyloxymethyl)-2,6-dichlorobenzene with 4-(methylcarbamoyl)cinnamic acid according to a similar manner to that of Example 7.

mp: 219–222° C.

NMR (CDCl₃, δ): 1.05 (9H, s), 3.02 (3H, d, J=5 Hz), 3.21 (3H, s), 3.56 (1H, dd, J=17.4 Hz), 3.93 (1H, dd, J=17, 5 Hz), 4.91 (1H, d, J=10 Hz), 4.98 (1H, d, J=10 Hz), 6.15 (1H, br d, J=5 Hz), 6.51 (1H, d, J=15 Hz), 6.63 (1H, br s), 7.19–7.28 (2H, m), 7.32–7.48 (6H, m), 7.50–7.60 (3H, m), 7.68–7.78 (6H, m)

(3) To a suspension of 1-(tert-butyldiphenylsilyloxymethyl)-2,6-dichloro-3-[N-methyl-N-[4-(methylcarbamoyl)-cinnamoylglycyl]amino]benzene (17.6 g) in tetrahydrofuran (138 ml) was added 1M tetrabutylammonium fluoride in tetrahydrofuran (38.4 ml) at ambient temperature. The reaction mixture was stirred for 1 hour. The mixture was concentrated and diluted with dichloromethane. The organic layer was washed with 1N hydrochloric acid, saturated sodium bicarbonate solution and water, dried over magnesium sulfate and evaporated in vacuo to give 2,6-dichloro-1-hydroxymethyl-3-[N-methyl-N-[4-(methylcarbamoyl)cinnamoylglycyl]amino]-benzene (8.14 g).

mp: 207–211° C.

NMR (DMSO-d₆, δ): 2.79 (3H, d, J=5 Hz), 3.11 (3H, s), 3.47 (1H, dd, J=17, 4 Hz), 3.77 (1H, dd, J=17, 5 Hz), 4.74 (1H, d, J=5 Hz), 5.34 (1H, t, J=5 Hz), 6.87 (1H, d, J=15 Hz), 7.40 (1H, d, J=15 Hz), 7.59–7.68 (4H, m), 7.85 (2H, d, J=8 Hz), 8.29 (1H, t, J=5 Hz), 8.48 (1H, d, J=5 Hz)

(4) To a mixture of 2,6-dichloro-1-hydroxymethyl-3-[N-methyl-N-[4-(methylcarbamoyl)cinnamoylglycyl]amino]benzene (8.10 g) in dichloromethane (81 ml) were added triphenylphosphine (5.66 g) and carbon tetrabromide (8.95 g) at 0° C. After 15 minutes, the reaction mixture was stirred at ambient temperature for 3 hours. To the mixture were added triphenylphosphine (1.42 g) and carbon tetrabromide (2.39 g) and stirred for another 2 hours. The reaction mixture was washed with saturated sodium hydrogen carbonate, water and brine. After dried over anhydrous magnesium sulfate, the mixture was evaporated in vacuo. The residue was purified by flash column chromatography followed by crystallizing from ethyl acetate to give 2,6-dichloro-3-[N-methyl-N-[4-(methylcarbamoyl)cinnamoylglycyl]amino]benzyl bromide (6.40 g) as pale yellow crystals.

mp: 211.6–216.5° C.

NMR (CDCl₃, δ): 3.02 (3H, d, J=5 Hz), 3.27 (3H, s), 3.62 (1H, dd, J=17, 4 Hz), 3.92 (1H, dd, J=17, 5 Hz), 4.78 (1.2H, s), 4.90 (0.8H, s), 6.15 (1H, br d, J=5 Hz), 6.51 (1H, d, J=15 Hz), 6.67 (1H, br t, J=5 Hz), 7.29 (1H, overlapped with H₂O), 7.45–7.62 (4H, m), 7.76 (2H, d, J=8 Hz)

Preparation 17

(1) To a mixture of 2,6-dimethylbenzyl alcohol (17.1 g) and acetic anhydride (14.2 ml) was added 4-dimethylaminopyridine (17 mg), and the mixture was stirred at 70° C. for 5 hours. After cooling, the mixture was concentrated in vacuo, and ethyl acetate was added to the residue. The solution was washed with water, dried over magnesium sulfate and evaporated in vacuo to give 2,6-dimethylbenzyl acetate (22.5 g) as colorless oil.

NMR (CDCl₃, δ): 2.07 (3H, s), 2.38 (6H, s), 5.19 (2H, s), 7.05 (2H, d, J=8 Hz), 7.15 (1H, t, J=8 Hz)

(2) To a solution of acetic anhydride (70 ml) and acetic acid (35 ml) was added cupric nitrate trihydrate (34.2 g) under ice-cooling, and a solution of 2,6-dimethylbenzyl acetate (21.0 g) in acetic anhydride (21 ml) and acetic acid (10 ml) was dropwise added thereto over the period of 30 minutes with stirring. The mixture was stirred for 30 minutes at the same temperature and then for 30 minutes at ambient temperature. The reaction mixture was poured into ice water, and extracted with ethyl acetate. The organic layer was washed with water and brine, dried over magnesium sulfate and evaporated in vacuo to give 2,6-dimethyl 3-nitrobenzyl acetate (26.9 g) as pale yellow oil.

NMR (CDCl₃, δ): 2.08 (3H, s), 2.47 (3H, s), 2.50 (3H, s), 5.22 (2H, s), 7.18 (1H, d, J=8 Hz), 7.69 (1H, d, J=8 Hz)

(3) To a solution of 2,6-dimethyl-3-nitrobenzyl acetate (26.9 g) in methanol (266 ml) was added 1N sodium hydroxide solution (133 ml) at ambient temperature, and the mixture was stirred for 30 minutes. To the reaction mixture was added water, and the resulting precipitates were collected by filtration to give 2,6-dimethyl-3-nitrobenzyl alcohol (18.0 g) as pale yellow crystals.

mp: 99–102° C.

NMR (CDCl₃, δ): 1.44 (1H, t, J=5 Hz), 2.50 (3H, s), 2.56 (3H, s), 4.82 (2H, d, J=5 Hz), 7.17 (1H, d, J=8 Hz), 7.66 (1H, d, J=8 Hz)

(4) To a solution of tert-butyldiphenylsilyl chloride (30.7 g) in dimethylformamide (90 ml) was added 2,6-dimethyl-3-nitrobenzyl alcohol (18.4 g), and imidazole (8.99 g) was added thereto under ice-cooling. The mixture was stirred for 15 minutes at the same temperature and then for 3 hours at ambient temperature. The reaction mixture was poured into ice water, and extracted with ethyl acetate. The organic layer was washed with water and brine, dried over magnesium sulfate and evaporated in vacuo to give 1-(tert-butyldiphenylsilyloxymethyl)-2,6-dimethyl-3-nitrobenzene (46.67 g) as pale yellow oil.

NMR (CDCl$_3$, δ): 1.03 (9H, s), 2.20 (3H, s), 2.38 (3H, s), 5.73 (2H, s), 7.06 (1H, d, J=8 Hz), 7.33–7.49 (6H, m), 7.58–7.73 (5H, m)

(5) To a suspension of 1-(tert-butyldiphenylsilyloxymethyl)-2,6-dimethyl-3-nitrobenzene (42 g) and ammonium chloride (4.2 g) in ethanol (378 ml)-water (42 ml) was added iron (7.0 g), and the mixture was refluxed for 6 hours, during which iron (7.0 g) was added thereto twice. Insoluble materials were filtered off, and the filtrate was concentrated. To the residue was added water and extracted with ethyl acetate. The organic layer was washed with water and brine, dried over magnesium sulfate and concentrated to give 3-amino-1-(tert-butyldiphenylsilyloxymethyl)-2,6-dimethylbenzene (42.8 g) as pale yellow oil.

NMR (CDCl$_3$, δ): 1.04 (9H, s), 2.09 (3H, s), 2.11 (3H, s), 3.48 (2H, br s), 4.70 (2H, s), 6.58 (1H, d, J=8 Hz), 6.71 (1H, d, J=8 Hz), 7.33–7.48 (6H, m), 7.66–7.73 (4H, m)

(6) To a suspension of 3-amino-1-(tert-butyldiphenyl-silyloxymethyl)-2,6-dimethylbenzene (42.4 g) in pyridine (17.2 g) and dimethylformamide (212 ml) was dropwise added phthalimidoacetyl chloride (25.6 g) over the period of 15 minutes under ice-cooling, and the mixture was stirred for 1 hour at the same temperature. To the reaction mixture was added water, and the resulting precipitates were collected by filtration and washed with acetonitrile to give 1-(tert-butyldiphenylsilyloxymethyl)-2,6-dimethyl-3-(phthalimidoacetylamino)benzene (59.1 g) as colorless crystals.

mp: 207–210° C.

NMR (CDCl$_3$, δ): 1.02 (9H, s), 2.12 (3H, s), 2.19 (3H, s), 4.52 (2H, s), 4.70 (2H, s), 6.95 (1H, d, J=8 Hz), 7.25–7.50 (7H, m), 7.63–7.80 (6H, m), 7.86–7.96 (2H, m)

(7) To a suspension of 1-(tert-butyldiphenylsilyloxymethyl)-2,6-dimethyl-3-(phthalimidoacetylamino)benzene (57.4 g) and sodium hydride (4.78 g) in dimethylformamide (287 ml) was dropwise added methyl iodide (15.5 g) under ice-cooling, and the mixture was stirred for 15 minutes at the same temperature and then for 2 hours at ambient temperature. Water and ethyl acetate were added to the reaction mixture, and the resulting precipitates were collected by filtration and washed with water and ethyl acetate to give 1-(tert-butyldiphenylsilyloxymethyl)-2,6-dimethyl-3-[N-methyl-N-(phthalimidoacetyl)amino]benzene (28.18 g) as colorless crystals.

mp: 180–182° C.

NMR (CDCl$_3$, δ): 1.04 (9H, s), 2.21 (3H, s), 2.27 (3H, s), 3.17 (3H, s), 3.82 (1H, d, J=17 Hz), 4.12 (1H, d, J=17 Hz), 4.78 (2H, s), 7.09 (1H, d, J=8 Hz), 7.15 (1H, d, J=8 Hz), 7.34–7.49 (6H, m), 7.65–7.73 (6H, m), 7.80–7.88 (2H, m)

(8) 1-(tert-Butyldiphenylsilyloxymethyl)-2,6-dimethyl-3-(N-glycyl-N-methylamino)benzene was obtained according to a similar manner to that of Example 3.

NMR (CDCl$_3$, δ) 1.03 (9H, s), 2.02 (3H, s), 2.22 (3H, s), 2.82 (1H, d, J=17 Hz), 3.09 (1H, d, J=17 Hz), 3.15 (3H, s), 4.72 (2H, s), 6.92 (1H, d, J=8 Hz), 7.01 (1H, d, J=8 Hz), 7.32–7.49 (6H, m), 7.62–7.70 (4H, m)

(9) 3-[N-[(E)-3-(6-Acetylaminopyridin-3-yl) acryloylglycyl]-N-methylamino]-1-(tert-butyldiphenylsilyloxymethyl)-2,6-dimethylbenzene was obtained by reacting 1-(tert-butyldiphenylsilyloxymethyl)-2,6-dimethyl-3-(N-glycyl-N-methylamino)benzene with (E)-3-(6-acetylaminopyridin-3-yl)acrylic acid according to a similar manner to that of Example 7.

mp: 200–202° C.

NMR (CDCl$_3$, δ): 1.05 (9H, s), 2.04 (3H, s), 2.21 (3H, s), 2.26 (3H, s), 3.20 (3H, s), 3.52 (1H, dd, J=17, 5 Hz), 3.87 (1H, dd, J=17, 5 Hz), 4.73 (2H, s), 6.45 (1H, d, J=15 Hz), 6.69 (1H, br t, J=5 Hz), 6.98 (1H, d, J=8 Hz), 7.07 (1H, d, J=8 Hz), 7.35–7.47 (6H, m), 7.64–7.71 (4H, m), 7.84 (1H, dd, J=8, 3 Hz), 8.06 (1H, br s), 8.21 (1H, br d, J=8 Hz), 8.35 (1H, br s)

(10) 3-[N-[(E)-3-(6-Acetylaminopyridin-3-yl) acryloylglycyl]-N-methylamino]-1-hydroxymethyl-2,6-dimethylbenzene was obtained according to a similar manner to that of Preparation 16-(3).

mp: 215–216° C.

NMR (CDCl$_3$, δ) 1.64 (1H, t, J=5 Hz), 2.21 (3H, s), 2.30 (3H, s), 2.48 (3H, s), 3.24 (3H, s), 3.62 (1H, dd, J=17, 5 Hz), 3.82 (1H, dd, J=17, 5 Hz), 4.78 (2H, d, J=5 Hz), 6.45 (1H, d, J=15 Hz), 6.75 (1H, br t, J=5 Hz), 7.01 (1H, d, J=8 Hz), 7.12 (1H, d, J=8 Hz), 7.50 (1H, d, J=15 Hz), 7.84 (1H, dd, J=8, 2 Hz), 8.13 (1H, br s), 8.21 (1H, br d, J=8 Hz), 8.35 (1H, d, J=2 Hz)

(11) 3-[N-[(E)-3-(6-Acetylaminopyridin-3-yl) acryloylglycyl]-N-methylamino]-2,6-dimethylbenzyl bromide was obtained according to a similar manner to that of Preparation 16-(4).

NMR (CDCl$_3$, δ): 2.22 (3H, s), 2.28 (3H, s), 2.46 (3H, s), 3.25 (3H, s), 3.60 (1H, dd, J=17, 5 Hz), 3.82 (1H, dd, J=17, 4 Hz), 4.55 (2H, s), 6,46 (1H, d, J=15 Hz), 6.71 (1H, br s), 7.03 (1H, d, J=8 Hz), 7.13 (1H, d, J=8 Hz), 7.51 (1H, d, J=15 Hz), 7.84 (1H, dd, J=8, 2 Hz), 8.13 (1H, br s), 8.22 (1H, br d, J=8 Hz), 8.36 (1H, d, J=2 Hz)

Preparation 18

To a solution of 3-[N-[(E)-3-(6-acetylaminopyridin-3-yl) acryloylglycyl]-N-methylamino]-1-hydroxymethyl-2,6-dimethylbenzene (69 mg) and triethylamine (20.4 mg) in dichloromethane (4.2 ml) was added mesyl chloride (21.2 mg) under ice-cooling, and the mixture was stirred for 10 minutes at the same temperature and then for 75 minutes at ambient temperature. The reaction mixture was washed with water and saturated sodium bicarbonate solution, and dried over magnesium sulfate. The solvent was removed in vacuo to give a mixture of 3-[N-[(E)-3-(6-acetylaminopyridin-3-yl)acryloylglycyl]-N-methylamino]-2,6-dimethylbenzyl chloride and 3-[N-[(E)-3-(6-acetylaminopyridin-3-yl) acryloylglycyl]-N-methylamino]-2,6-dimethyl-1-(methylsulfonyloxymethyl)benzene.

Preparation 19

To a solution of 3-[N-[(E)-3-(6-acetylaminopyridin-3-yl) acryloylglycyl]-N-methylamino]-1-hydroxymethyl-2,6-dimethylbenzene (200 mg) in dimethylformamide (2 ml) were added triethylamine (136.1 μl) and mesyl chloride (52.9 μl) at 0° C., and the mixture was stirred for 1 hour at the same temperature and then for 1 hour at ambient temperature. Chloroform and saturated sodium bicarbonate solution were added to the reaction mixture, and the separated organic layer was washed with water, saturated sodium bicarbonate solution and brine, and dried over magnesium sulfate. The solvent was removed in vacuo to give 3-[N-[(E)-3-(6-acetylaminopyridin-3-yl)acryloylglycyl]-N-methylamino]-2,6-dimethylbenzyl chloride (191.0 mg) as pale yellow solid.

mp: 217.5–220.5° C.

NMR (DMSO-d$_6$, δ): 2.11 (3H, s), 2.28 (3H, s), 2.43 (3H, s), 3.09 (3H, s), 3.41 (1H, dd, J=16.5, 5.5 Hz), 3.60 (1H, dd, J=16.5, 5.5 Hz), 4.84 (2H, s), 6.76 (1H, d, J=15.0 Hz), 7.21 (1H, d, J=8.5 Hz), 7.27 (1H, d, J=8.5 Hz), 7.37 (1H, d, J=15.0 Hz), 7.98 (1H, dd, J=8.5, 1.5 Hz), 8.11 (1H, d, J=8.5 Hz), 8.17 (1H, t, J=,5.5 Hz), 8.47 (1H, d, J=1.5 Hz)

Preparation 20

(1) 1-(tert-Butyldiphenylsilyloxymethyl)-2,6-dimethyl-3-[N-[4-(methylcarbamoyl)cinnamoylglycyl]-N-methylamino]benzene was obtained by reacting 1-(tert-butyldiphenylsilyloxy-methyl)-2,6-dimethyl-3-(N-glycyl-N-methylamino)benzene with 4-(methylcarbamoyl) cinnamic acid according to a similar manner to that of Example 7.

mp: 204–208° C.

NMR (CDCl$_3$, δ) 1.05 (9H, s), 2.05 (3H, s), 2.26 (3H, s), 3.02 (3H, d, J=5 Hz), 3.20 (3H, s), 3.52 (1H, dd, J=17, 5 Hz), 3.87 (1H, dd, J=17, 5 Hz), 4.73 (2H, s), 6.16 (1H, br d, J=5 Hz), 6.51 (1H, d, J=15 Hz), 6.69 (1H, br t, J=5 Hz), 6.98 (1H, d, J=8 Hz), 7.06 (1H, d, J=8 Hz), 7.35–7.48 (6H, m), 7.51–7.60 (3H, m), 7.65–7.80 (6H, m)

(2) 1-Hydroxymethyl-2,6-dimethyl-3-[N-[4-(methylcarbamoyl)-cinnamoylglycyl]-N-methylamino]benzene was obtained according to a similar manner to that of Preparation 16-(3).

mp: 261–263° C.

NMR (DMSO-d$_6$, δ) 2.27 (3H, s), 2.40 (3H, s), 2.79 (3H, d, J=5 Hz), 3.08 (3H, s), 3.43 (1H, dd, J=17, 5 Hz), 3.65 (1H, dd, J=17, 5 Hz), 4.53 (2H, d, J=5 Hz), 4.88 (1H, t, J=5 Hz), 6.89 (1H, d, J=15 Hz), 7.15 (2H, s), 7.41 (1H, d, J=15 Hz), 7.64 (2H, d, J=8 Hz), 7.85 (2H, d, J=8 Hz), 8.21 (1H, br t, J=5 Hz), 8.48 (1H, br d, J=8 Hz)

(3) 2,6-Dimethyl-3-[N-[4-(methylcarbamoyl) cinnamoylglycyl]-N-methylamino]benzyl chloride was obtained according to a similar manner to that of Preparation 19.

mp: 232° C.

NMR (CDCl$_3$, δ): 2.29 (3H, s), 2.46 (3H, s), 3.03 (3H, d, J=5 Hz), 3.24 (3H, s), 3.59 (1H, d, J=17, 5 Hz), 3.82 (1H, dd, J=17, 4 Hz), 4.67 (2H, s), 6.20 (1H, m), 6.50 (1H, d, J=15 Hz), 6.70 (1H, d, J=5 Hz), 7.04 (1H, d, J=9 Hz), 7.14 (1H, d, J=9 Hz), 7.50–7.60 (3H, m), 7.75 (2H, d, J=9 Hz)

Example 9

(1) To a solution of 1-ethoxycarbonylmethyl-2-ethyl-4-hydroxy-1H-benzimidazole (140 mg) and 2,6-dichloro-3-[N-methyl-N-[4-(methylcarbamoyl)cinnamoylglycyl] amino]benzyl bromide (289 mg) in dimethylformamide (3 ml) was added potassium carbonate (117 mg) under ice-cooling, and the mixture was stirred for 30 minutes at the same temperature and then for 2 hours at ambient temperature. To the reaction mixture was added saturated sodium bicarbonate solution, and the mixture was extracted with ethyl acetate. The organic layer was dried over magnesium sulfate, and concentrated in vacuo. The residue was purified by silica gel flash chromatography (5% methanol-ethyl acetate) and pulverized with diisopropyl ether to give 4-[2,6-dichloro-3-[N-methyl-N-[4-(methylcarbamoyl) cinnamoylglycyl]amino]benzyloxy]-1-ethoxycarbonylmethyl-2-ethyl-1H-benzimidazole (317 mg) as pale yellow solid.

NMR (CDCl$_3$, δ): 1.26 (3H, t, J=7.5 Hz), 1.34 (3H, t, J=7.5 Hz), 2.86 (2H, q, J=7.5 Hz), 3.00 (3H, d, J=5 Hz), 3.25 (3H, s), 3.66 (1H, dd, J=17, 4 Hz), 3.92 (1H, dd, J=17, 5 Hz), 4.22 (2H, q, J=7.5 Hz), 4.80 (2H, s), 5.57 (1H, d, J=9 Hz), 5.61 (1H, d, J=9 Hz), 6.26 (1H, br q, J=5 Hz), 6.53 (1H, d, J=15 Hz), 6.70 (1H, dd, J=5, 4 Hz), 6.85 (1H, d, J=8 Hz), 6.89 (1H, d, J=8 Hz), 7.19 (1H, t, J=8 Hz), 7.29 (1H, d, J=8 Hz), 7.46 (1H, d, J=8 Hz), 7.52 (2H, d, J=9 Hz), 7.57 (1H, d, J=15 Hz), 7.74 (2H, d, J=9 Hz)

Example 10

To a solution of 4-[2,6-dichloro-3-[N-methyl-N-[4-(methylcarbamoyl)cinnamoylglycyl]amino]benzyloxy]-1-ethoxycarbonylmethyl-2-ethyl-1H-benzimidazole (270 mg) in ethanol (3 ml) was added 1N sodium hydroxide solution (0.44 ml), and the mixture was stirred for 2 hours at ambient temperature. The reaction mixture was acidified with 1N hydrochloric acid, and the solvent was removed in vacuo. The residue was pulverized with 99% acetonitrile to give 1-carboxymethyl-4-[2,6-dichloro-3-[N-methyl-N-[4-(methylcarbamoyl)cinnamoylglycyl]amino]benzyloxy]-2-ethyl-1H-benzimidazole (280 mg) as pale yellow solid.

NMR (DMSO-d$_6$, δ): 1.26 (3H, t, J=7.5 Hz), 2.78 (3H, d, J=5 Hz), 3.15 (3H, s), 3.34 (2H, overlapped with H$_2$O), 3.54 (1H, dd, J=17, 5 Hz), 3.83 (1H, dd, J=17, 4 Hz), 5.16 (2H, br s), 5.55 (2H, s), 6.87 (1H, d, J=15 Hz), 7.24 (2H, br s), 7.43 (1H, d, J=15 Hz), 7.64 (2H, d, J=9 Hz), 7.80 (1H, s), 7.88 (2H, d, J=9 Hz), 8.36 (1H, t, J=5 Hz), 8.52 (1H, q, J=5 Hz)

Example 11

(1) A solution of 1-carboxymethyl-4-[2,6-dichloro-3-[N-methyl-N-[4-(methylcarbamoyl)cinnamoylglycyl]amino]-benzyloxy]-2-ethyl-1H-benzimidazole (60 mg), dimethylamine hydrochloride (11.2 mg), 1-ethyl-3-(3-dimethylaminopropyl)-carbodiimide (17.1 mg) and 1-hydroxybenzotriazole (18.6 mg) in dimethylformamide (1 ml) was stirred for 1 day at ambient temperature. To the reaction mixture was added water, and the mixture was extracted with chloroform. The organic layer was washed with saturated sodium bicarbonate solution, dried over magnesium sulfate, and concentrated in vacuo. The residue was purified by preparative thin layer chromatography (10% methanol-chloroform) to give 4-[2,6-dichloro-3-[N-methyl-N-[4-(methyl-carbamoyl)cinnamoylglycyl]amino]-benzyloxy]-2-ethyl-1-dimethylcarbamoylmethyl-1H-benzimidazole (46 mg) as amorphous.

NMR (CDCl$_3$, δ): 1.34 (3H, t, J=7.5 Hz), 2.78 (2H, q, J=7.5 Hz), 2.98 (3H, d, J=5 Hz), 3.01 (3H, s), 3.15 (3H, s), 3.25 (3H, s), 3.67 (1H, dd, J=15, 4 Hz), 3.92 (1H, d, J=15, 5 Hz), 4.85 (2H, s), 5.59 (2H, s), 6.47 (1H, m), 6.53 (1H, d, J=15 Hz), 6.82 (2H, d, J=8 Hz), 6.85 (1H, m), 7.16 (1H, t, J=8 Hz), 7.28 (1H, d, J=9 Hz), 7.43 (1H, d, J=9 Hz), 7.49 (2H, d, J=9 Hz), 7.54 (1H, d, J=15 Hz), 7.70 (2H, d, J=9 Hz)

its hydrochloride

NMR (CDCl$_3$—CD$_3$OD, δ): 1.34–1.54 (3H, m), 2.97 (3H, s), 3.02 (3H, s), 3.07–3.30 (2H, m), 3.28 (3H, s), 3.31 (3H, s), 3.80 (1H, d, J=15 Hz), 3.88 (1H, d, J=15 Hz), 5.44–5.69 (2H, m), 5.50 (1H, d, J=9 Hz), 5.60 (1H, d, J=9 Hz), 6.64 (1H d, J=15 Hz), 7.13 (1H, d, J=9 Hz), 7.27 (1H, d, J=9 Hz), 7.44–7.58 (5H, m), 7.60 (1H, d, J=9 Hz), 7.80 (2H, d, J=9 Hz)

Example 12

1-Allylcarbamoylmethyl-4-[2,6-dichloro-3-[N-methyl-N-[4-(methylcarbamoyl)cinnamoylglycyl]amino] benzyloxy]-2-ethyl-1H-benzimidazole was obtained from 1-carboxymethyl-4-[2,6-dichloro-3-[N-methyl-N-[4-(methylcarbamoyl) cinnamoylglycyl]-amino]benzyloxy]-2-ethyl-1H-benzimidazole and allylamine according to a similar manner to that of Example 11.

NMR (CDCl₃, δ) 1.33 (3H, t, J=7.5 Hz), 2.84 (2H, q, J=7.5 Hz), 3.00 (3H, d, J=5 Hz), 3.28 (3H, s), 3.67 (1H, dd, J=15, 4 Hz), 3.80 (2H, br t, J=5 Hz), 3.91 (1H, dd, J=15, 5 Hz), 4.78 (2H, s), 5.00 (1H, br d, J=17 Hz), 5.05 (1H, br d, J=10 Hz), 5.58–5.76 (2H, m), 5.60 (2H, s), 6.15 (1H, m), 6.53 (1H, d, J=15 Hz), 6.67 (1H, m), 6.92 (1H, d, J=9 Hz), 6.95 (1H, d, J=9 Hz), 7.24 (1H, t, J=9 Hz), 7.31 (1H, d, J=9 Hz), 7.50 (1H, d, J=9 Hz), 7.54 (2H, d, J=9 Hz), 7.57 (1H, d, J=17 Hz), 7.74 (2H, d, J=9 Hz)

Example 13

2-Methoxy-1-methyl-4-[2,6-dichloro-3-[N-methyl-N-[4-(methylcarbamoyl) cinnamoylglycyl]amino]benzyloxy]-1H-benzimidazole was obtained from 4-hydroxy-2-methoxy-1-methyl-1H-benzimidazole and 2,6-dichloro-3-[N-methyl-N-[4-(methylcarbamoyl) cinnamoylglycyl] amino]benzyl bromide according to a similar manner to that of Example 9.

mp: 244–249° C.

NMR (CDCl₃, δ): 3.02 (3H, d, J=4.5 Hz), 3.27 (3H, s), 3.53 (3H, s), 3.67 (1H, dd, J=16.5, 4.5 Hz), 3.93 (1H, dd, J=16.5, 4.5 Hz), 4.17 (3H, s), 5.64 (2H, s), 6.29 (1H, q, J=4.5 Hz), 6.53 (1H, d, J=16.0 Hz), 6.70 (1H, t, J=4.5 Hz), 6.82–6.90 (2H, m), 7.11 (1H, t, J=8.5 Hz), 7.30 (1H, d, J=8.5 Hz), 7.46 (1H, d, J=8.5 Hz), 7.53 (2H, d, J=7.5 Hz), 7.58 (1H, d, J=16.0 Hz), 7.76 (2H, d, J=7.5 Hz)

Example 14

4-[3-[N-[(E)-3-(6-Acetylaminopyridin-3-yl)acryloylglycyl]-N-methylamino]-2,6-dimethylbenzyloxy]-2-methoxy-1-methyl-1H-benzimidazole was obtained from 4-hydroxy-2-methoxy-1-methyl-1H-benzimidazole and a mixture of 3-[N-[(E)-3-(6-acetylaminopyridin-3-yl)acryloylglycyl]-N-methylamino]-2,6-dimethyl-1-(methylsulfonyloxymethyl)benzene and 3-[N-[(E)-3-(6-acetylaminopyridin-3-yl) acryloylglycyl]-N-methylamino]-2,6-dimethylbenzyl chloride according to a similar manner to that of Example 1.

NMR (CDCl₃, δ): 2.21 (3H, s), 2.33 (3H, s), 2.50 (3H, s), 3.26 (3H, s), 3.54 (3H, s), 3.62 (1H, dd, J=17, 5 Hz), 3.88 (1H, dd, J=17, 5 Hz), 4.19 (3H, s), 5.40 (2H, s), 6.47 (1H, d, J=15 Hz), 6.72 (1H, br t, J=5 Hz), 6.81–6.89 (2H, m), 7.03–7.18 (3H, m), 7.51 (1H, d, J=15 Hz), 7.84 (1H, dd, J=8, 2 Hz), 8.11 (1H, br s), 7.21 (1H br d, J=8 Hz), 8.36 (1H, br s)

Example 15

The following compounds were obtained according to a similar manner to that of Example 9.

(1) 2-Methoxy-1-methyl-4-[3-[N-methyl-N-[4-(methylcarbamoyl)cinnamoylglycyl]amino]-2,6-dimethylbenzyloxy]-1H-benzimidazole (2) 4-[3-[N-[(E)-3-(6-Acetylaminopyridin-3-yl)acryloylglycyl]-N-methylamino]-2,6-dichlorobenzyloxy]-2-methoxy-1-methyl-1H-benzimidazole (3) 4-[3-[N-[(E)-3-(6-Acetylaminopyridin-3-yl)acryloylglycyl]-N-methylamino]-2,6-dichlorobenzyloxy]-1,2-dimethyl-1H-benzimidazole (4) 4-[3-[N-Methyl-N-[4-(methylcarbamoyl)cinnamoylglycyl]-amino]-2,6-dimethylbenzyloxy]-1,2-dimethyl-1H-benzimidazole (5) 4-[3-[N-[(E)-3-(6-Acetylaminopyridin-3-yl)acryloylglycyl]-N-methylamino]-2,6-dimethylbenzyloxy]-1,2-dimethyl-1H-benzimidazole (6) 4-(2,6-Dimethyl-3-[N-[4-(methylcarbamoyl) cinnamoylglycyl]-N-methylamino]benzyloxy]-2-ethoxy-1-methyl-1H-benzimidazole mp: 226–231° C.

NMR (CDCl₃, δ): 1.43 (3H, t, J=7.0 Hz), 2.32 (3H, s), 2.50 (3H, s), 3.00 (3H, d, J=4.5 Hz), 3.24 (3H, s), 3.53 (3H, s), 3.61 (1H, dd, J=17.5, 4.5 Hz), 3.87 (1H, dd, J=17.5, 4.5 Hz), 4.59 (2H, q, J=7.0 Hz), 5.41 (2H, s), 6.23 (1H, q, J=4.5 Hz), 6.52 (1H, d, J=15.0 Hz), 6.72 (1H, t, J=4.5 Hz), 6.80–6.89 (2H, m), 7.02–7.17 (3H, m), 7.52 (2H, d, J=8.5 Hz), 7.56 (1H, d, J=15.0 Hz), 7.74 (2H, d, J=8.5 Hz) (7) 4-[3-[N-[(E)-3-(6-Acetamidopyridin-3-yl)acryloylglycyl]-N-methylamino]-2,6-dimethylbenzyloxy]-2-ethoxy-1-methyl-1H-benzimidazole mp: 142.5–148.5° C.

NMR (CDCl₃, δ): 1.47 (3H, t, J=7.5 Hz), 2.22 (3H, s), 2.33 (3H, s), 2.50 (3H, s), 3.25 (3H, s), 3.56 (3H, s), 3.64 (1H, dd, J=17.5, 4.5 Hz), 3.88 (1H, dd, J=17.5, 4.5 Hz), 4.60 (2H, q, J=7.5 Hz), 5.42 (2H, s), 6.46 (1H, d, J=15.0 Hz), 6.73 (1H, t, J=4.5 Hz), 6.81–6.90 (2H, m), 7.01–7.19 (3H, m), 7.51 (1H, d, J=15.0 Hz), 7.84 (1H, dd, J=8.5, 1.5 Hz), 8.12 (1H, d, J=1.5 Hz), 8.20 (1H, d, J=8.5 Hz), 8.36 (1H, d, J=1.5 Hz)

(8) 4-[2,6-Dimethyl-3-[N-[4-(methylcarbamoyl) cinnamoylglycyl]-N-methylamino]benzyloxy]-2-methoxymethyl-1-methyl-1H-benzimidazole mp: 232–235° C.

NMR (DMSO-d₆, δ): 2.28 (3H, s), 2.40 (3H, s), 2.79 (3H, d, J=4.5 Hz), 3.10 (3H, s), 3.28 (3H, s), 3.49 (1H, dd, J=16.5, 5.0 Hz), 3.67 (1H, dd, J=16.5, 5.0 Hz), 3.78 (3H, s), 4.63 (2H, s), 5.34 (2H, s), 6.87 (1H, d, J=15.5 Hz), 6.92 (1H, d, J=7.5 Hz), 7.13–7.33 (4H, m), 7.42 (1H, d, J=15.5 Hz), 7.62 (2H, d, J=8.5 Hz), 7.84 (2H, d, J=8.5 Hz), 8.26 (1H, t, J=5.0 Hz), 8.48 (1H, q, J=4.5 Hz)

its hydrochloride mp: 225–233° C.

NMR (DMSO-d₆, δ): 2.29 (3H, s), 2.43 (3H, s), 2.79 (3H, d, J=4.5 Hz), 3.12 (3H, s), 3.38 (3H, s), 3.50 (1H, dd, J=16.5, 6.0 Hz), 3.70 (1H, dd, J=16.5, 6.0 Hz), 3.98 (3H, s), 4.89 (2H, s), 5.37 (1H, d, J=10.0 Hz), 5.44 (1H, d, J=10.0 Hz), 6.91 (1H, d, J=16.0 Hz), 7.27–7.46 (4H, m), 7.50–7.68 (2H, m), 7.63 (2H, d, J=8.5 Hz), 7.87 (2H, d, J=8.5 Hz), 8.30 (1H, t, J=6.0 Hz), 8.53 (1H, q, J=4.5 Hz)

(9) 2-Acetyl-4-[2,6-dimethyl-3-[N-[4-(methylcarbamoyl) cinnamoylglycyl]-N-methylamino]benzyloxy]-1-methyl-1H-benzimidazole mp: 234–236° C.

NMR (DMSO-d₆, δ): 2.32 (3H, s), 2.45 (3H, s), 2.67 (3H, s), 2.79 (3H, d, J=4.5 Hz), 3.12 (3H, s), 3.50 (1H, dd, J=16.5, 5.5 Hz), 3.67 (1H, dd, J=16.5, 5.5 Hz), 4.04 (3H, s), 5.38 (2H, s), 6.88 (1H, d, J=16.0 Hz), 7.08 (1H, d, J=7.5 Hz), 7.25–7.47 (5H, m), 7.63 (2H, d, J=8.5 Hz), 7.85 (2H, d, J=8.5 Hz), 8.25 (1H, t, J=5.5 Hz), 8.47 (1H, q, J=4.5 Hz)

its hydrochloride mp: 141–152° C.

NMR (DMSO-d₆, δ): 2.31 (3H, s), 2.43 (3H, s), 2.67 (3H, s), 2.78 (3H, d, J=4.5 Hz), 3.11 (3H, s), 3.50 (1H, dd,

J=16.5, 5.5 Hz), 3.67 (1H, dd, J=16.5, 5.5 Hz), 4.04 (3H, s), 5.38 (2H, s), 6.88 (1H, d, J=16.0 Hz), 7.08 (1H, d, J=7.5 Hz), 7.12–7.47 (5H, m), 7.63 (2H, d, J=8.5 Hz), 7.86 (2H, d, J=8.5 Hz), 8.27 (1H, t, J=5.5 Hz), 8.50 (1H, q, J=4.5 Hz)

(10) 4-[2,6-Dimethyl-3-[N-[4-(methylcarbamoyl)cinnamoylglycyl]-N-methylamino]benzyloxy]-2-ethoxycarbonylmethyl-1-methyl-1H-benzimidazole mp: 128–146° C.

NMR (DMSO-$d_6$, δ) 1.19 (3H, t, J=7.5 Hz), 2.29 (3H, s), 2.40 (3H, s), 2.79 (3H, d, J=4.5 Hz), 3.12 (3H, s), 3.49 (1H, d, J=16.5, 5.5 Hz), 3.67 (1H, dd, J=16.5, 5.5 Hz), 3.72 (3H, s), 4.09 (2H, s), 4.11 (2H, q, J=7.5 Hz), 5.33 (2H, s), 6.89 (1H, d, J=16.0 Hz), 6.92 (1H, d, J=8.5 Hz), 7.13–7.33 (4H, m), 7.42 (1H, d, J=16.0 Hz), 7.63 (2H, d, J=7.5 Hz), 7.84 (2H, d, J=7.5 Hz), 8.25 (1H, t, J=5.5 Hz), 8.48 (1H, q, J=4.5 Hz)

(11) 4-[2,6-Dimethyl-3-[N-[4-(methylcarbamoyl)cinnamoylglycyl]-N-methylamino]benzyloxy]-1-methyl-2-dimethylamino-1H-benzimidazole NMR (CDCl$_3$, δ): 2.34 (3H, s), 2.50 (3H, s), 2.95 (6H, s), 3.01 (3H, d, J=5 Hz), 3.23 (3H, s), 3.58–3.68 (4H, m), 3.88 (1H, dd, J=17, 5 Hz), 5.42 (2H, s), 6.20 (1H, br d, J=5 Hz), 6.52 (1H, t, J=15 Hz), 6.72 (1H, br t, J=5 Hz), 6.80–6.90 (2H, m), 7.01–7.17 (3H, m), 7.50–7.60 (2H, m), 7.75 (2H, d, J=8 Hz)

(12) 4-[2,6-Dimethyl-3-[N-[4-(methylcarbamoyl)cinnamoylglycyl]-N-methylamino]benzyloxy]-1-methyl-2-methylamino-1H-benzimidazole NMR (CDCl$_3$—CD$_3$OD, δ): 2.29 (3H, s), 2.40 (3H, br s), 2.98 (3H, s), 3.03 (3H, s), 3.22 (3H, s), 3.53 (3H, br s), 3.66 (1H, d, J=17 Hz), 3.87 (1H, d, J=17 Hz), 5.27 (2H, br s), 6.57 (1H, d, J=15 Hz), 6.80–6.89 (2H, m), 7.06–7.16 (3H, m), 7.50–7.61 (3H, m), 7.75 (2H, d, J=8 Hz)

(13) 4-[3-[N-[(E)-3-(6-Acetamidopyridin-3-yl)acryloylglycyl]-N-methylamino]-2,6-dichlorobenzyloxy]-2-isopropyl-1-methyl-1H-benzimidazole NMR (CDCl$_3$, δ): 1.41 (6H, d, J=7.5 Hz), 2.21 (3H, s), 3.13–3.30 (4H, m), 3.60–3.75 (4H, m), 3.93 (1H, dd, J=4, 18 Hz), 5.69 (2H, s), 6.45 (1H, d, J=16 Hz), 6.70 (1H, t-like), 6.85 (1H, d, J=8 Hz), 6.97 (1H, d, J=8 Hz), 7.19 (1H, t, J=8 Hz), 7.30 (1H, d, J=8 Hz), 7.41–7.56 (2H, m), 7.31 (1H, dd, J=2, 8 Hz), 8.03 (1H, s), 8.19 (8H, br d), 8.35 (1H, d, J=2 Hz)

(14) 4-[3-[N-[(E)-3-(6-Acetamidopyridin-3-yl)acryloylglycyl]-N-methylamino]-2,6-dichlorobenzyloxy]-2-ethyl-1-methyl-1H-benzimidazole NMR (CDCl$_3$, δ) 1.36 (3H, t, J=7.5 Hz), 2.22 (3H, s), 2.92 (2H, q, J=7.5 Hz), 3.28 (3H, s), 3.61–3.75 (4H, m), 3.93 (1H, dd, J=4, 18 Hz), 5.59 (2H, s), 6.46 (1H, d, J=16 Hz), 6.65–6.72 (1H, m), 6.85 (1H, d, J=8 Hz), 6.99 (1H, d, J=8 Hz), 7.22 (1H, t, J=8 Hz), 7.30 (1H, d, J=8 Hz), 7.44–7.57 (2H, m), 7.83 (1H, dd, J=2, 8 Hz), 8.05 (1H, s), 8.20 (1H, br d, J=8 Hz), 8.35 (1H, s)

(15) 4-[3-[N-[(E)-3-(6-Acetamidopyridin-3-yl)acryloylglycyl]-N-methylamino]-2,6-dichlorobenzyloxy]-2-pentafluoroethyl-1H-benzimidazole NMR (CDCl$_3$, δ) 2.22 (3H, s), 3.26 (3H, s), 3.67 (1H, dd, J=4, 18 Hz), 3.87–4.00 (4H, m), 5.73 (2H, s), 6.45 (1H, d, J=16 Hz), 6.64 (1H, t-like), 6.95 (1H, d, J=8 Hz), 7.10 (1H, d, J=8 Hz), 7.32 (1H, d, J=8 Hz), 7.40 (1H, t, J=8 Hz), 7.45–7.57 (2H, m), 7.83 (1H, dd, J=2, 8 Hz), 8.00 (1H, s), 8.20 (1H, br d, J=8 Hz), 8.35 (1H, s)

(16) 9-[3-[N-[(E)-3-(6-Acetamidopyridin-3-yl)acryloylglycyl]-N-methylamino]-2,6-dichlorobenzyloxy]-3,4-dihydro-2H-[1,3]-oxazino[3,2-a]benzimidazole NMR (CDCl$_3$, δ): 2.21 (3H, s), 2.28–2.38 (2H, m), 3.25 (3H, s), 3.65 (1H, dd, J=17, 4 Hz), 3.95 (1H, dd, J=17, 5 Hz), 4.10 (2H, br t, J=6 Hz), 4.50 (2H, br t, J=6 Hz), 5.61 (2H, s), 6.46 (1H, d, J=15 Hz), 6.69 (1H, br s), 7.10 (1H, t, J=7.5 Hz), 7.29 (1H, d, J=7.5 Hz), 7.47 (1H, d, J=7.5 Hz), 7.51 (1H, d, J=15 Hz), 7.82 (1H, br d, J=7.5 Hz), 8.05 (1H, br s), 8.20 (1H, br d, J=7.5 Hz), 7.34 (1H, br s)

(17) 7-[3-[N-[(E)-3-(6-Acetamidopyridin-3-yl)acryloylglycyl]-N-methylamino]-2,6-dichlorobenzyloxy]-2-methylbenzoxazole mp: 225–227° C.

NMR (CDCl$_3$, δ): 2.22 (3H, s), 2.65 (3H, s), 3.29 (3H, s), 3.67 (1H, dd, J=17, 4 Hz), 3.97 (1H, dd, J=17, 5 Hz), 5.52 (1H, d, J=10 Hz), 5.59 (1H, d, J=10 Hz), 6.46 (1H, d, J=15 Hz), 6.68 (1H, br s), 7.00 (1H, d, J=7.5 Hz), 7.21–7.39 (3H, m), 7.51 (1H, br s), 7.56 (1H, d, J=5 Hz), 7.85 (1H, dd, J=7.5, 2 Hz), 8.06 (1H, br s), 8.22 (1H, br d, J=7.5 Hz), 7.36 (1H, d, J=2 Hz)

(18) 7-[3-[N-[(E)-3-(6-Acetamidopyridin-3-yl)acryloylglycyl]-N-methylamino]-2,6-dichlorobenzyloxy]-3-methyl-2(3H)-benzoxazolone NMR (CDCl$_3$, δ) 2.22 (3H, s), 3.28 (3H, s), 3.40 (3H, s), 3.63 (1H, dd, J=17, 4 Hz), 3.95 (1H, dd, J=17, 5 Hz), 5.50 (1H, d, J=10 Hz), 5.56 (1H, d, J=10 Hz), 6.46 (1H, d, J=15 Hz), 6.60–6.70 (2H, m), 6.88 (1H, d, J=7.5 Hz), 7.16 (1H, t, J=7.5 Hz), 7.34 (1H, d, J=7.5 Hz), 7.48–7.56 (2H, m), 7.85 (1H, br d, J=7.5 Hz), 8.04 (1H, br s), 8.21 (1H, br d, J=7.5 Hz), 8.37 (1H, br s)

(19) 7-[3-[N-[(E)-3-(6-Acetamidopyridin-3-yl)acryloylglycyl]-N-methylamino-2,6-dichlorobenzyloxy]-3-ethoxycarbonylmethyl-2(3H)-benzoxazolone NMR (CDCl$_3$, δ): 1.29 (3H, t, J=7.5 Hz), 2.21 (3H, s), 3.28 (3H, s), 3.63 (1H, dd, J=17, 4 Hz), 3.94 (1H, dd, J=17, 5 Hz), 4.54 (2H, s), 5.51 (1H, d, J=10 Hz), 5.58 (1H, d, J=10 Hz), 6.45 (1H, d, J=15 Hz), 6.59 (1H, d, J=7.5 Hz), 6.67 (1H, br s), 6.90 (1H, d, J=7.5 Hz), 7.15 (1H, t, J=7.5 Hz), 7.34 (1H, d, J=7.5 Hz), 7.49–7.57 (2H, m), 7.84 (1H, br d, J=7.5 Hz), 8.07 (1H, br s), 8.21 (1H, br d, J=7.5 Hz), 8.36 (1H, br s)

(20) 7-[2,6-Dichloro-3-[N-[4-(methylcarbamoyl)cinnamoylglycyl]-N-methylamino]benzyloxy]-2,3-dimethylbenzofuran (from 7-hydroxy-2,3-dimethylbenzofuran and 2,6-dichloro-3-[N-[4-(methylcarbamoyl)cinnamoylglycyl]-N-methylamino] benzyl bromide)

mp: 237.2° C.

NMR (DMSO-$d_6$, δ): 2.10 (3H, s), 2.32 (3H, s), 2.77 (3H, d, J=5 Hz), 3.13 (3H, s), 3.49 (1H, dd, J=17, 5 Hz), 3.76 (1H, dd, J=17, 4 Hz), 5.43 (2H, s), 6.85 (1H, d, J=15 Hz), 7.01 (1H, d, J=8 Hz), 7.05–7.18 (2H, m), 7.40 (1H, d, J=15 Hz), 7.63 (2H, d, J=9 Hz), 7.73 (1H, d, J=9 Hz), 7.77 (1H, d, J=9 Hz), 7.85 (2H, d, J=9 Hz), 8.32 (1H, br t, J=5 Hz), 8.49 (1H, br q, J=5 Hz)

Preparation 21

4-Benzyloxy-2-ethoxy-1-methyl-1H-benzimidazole was obtained from 3-benzyloxy-2-amino-N-methylaniline and tetraethylorthocarbonate according to a similar manner to that of Preparation 15-(2).

mp: 99–100° C.

NMR (CDCl$_3$, δ): 1.47 (3H, t, J=7.5 Hz), 3.51 (3H, s), 4.66 (2H, q, J=7.5 Hz), 5.40 (2H, s), 6.61 (1H, d, J=8.5 Hz), 6.75 (1H, d, J=8.5 Hz), 6.97 (1H, t, J=8.5 Hz), 7.22–7.38 (3H, m), 7.49 (2H, d, J=7.5 Hz)

Preparation 22

(1) To a mixture of 3-benzyloxy-2-nitro-N-methylaniline (400 mg) and N,N-dimethylaniline (1 ml) was added methoxyacetyl chloride (310 μl) under nitrogen atmosphere, and the mixture was stirred for 2.5 hours at 90° C. After cooling, ethyl acetate was added to the reaction mixture, and the mixture was washed with water and brine, dried over magnesium sulfate and evaporated in vacuo. The residue was purified by silica gel column chromatography (ethyl acetate:n-hexane=2:1, v/v) to give 3-benzyloxy-2-nitro-N-methoxyacetyl-N-methylaniline (474.2 mg).

mp: 111–112.5° C.

NMR (CDCl$_3$, δ): 3.20 (3H, s), 3.34 (3H, s), 3.79 (1H, d, J=15.0 Hz), 3.87 (1H, d, J=15.0 Hz), 5.22 (2H, s), 6.89 (1H, d, J=8.5 Hz), 7.13 (1H, d, J=8.5 Hz), 7.29–7.42 (5H, m), 7.45 (1H, t, J=8.5 Hz)

(2) 4-Benzyloxy-2-methoxymethyl-1-methyl-1H-benzimidazole was obtained according to a similar manner to that of Preparation 9.

mp: 120–122° C.

NMR (CDCl$_3$, δ): 3.38 (3H, s), 3.82 (3H, s), 4.78 (2H, s), 5.38 (2H, s), 6.67 (1H, d, J=8.5 Hz), 6.93 (1H, d, J=8.5 Hz), 7.14 (1H, t, J=8.5 Hz), 7.23–7.39 (3H, m), 7.51 (2H, d, J=8.5 Hz)

Preparation 23

(1) A mixture of 3-benzyloxy-2-amino-N-methylaniline (400 mg), lactic acid (473.8 mg) and 4N hydrochloric acid (1.6 ml) was refluxed for 1.5 hours. After cooling, the mixture was adjusted to pH 8 with 28% ammonia solution, and extracted with ethyl acetate. The organic layer was washed with water and brine, dried over magnesium sulfate and evaporated in vacuo. The residue was purified by silica gel column chromatography (ethyl acetate:n-hexane=2:1, v/v) to give 4-benzyloxy-2-(1-hydroxyethyl)-1-methyl-1H-benzimidazole (96.2 mg).

mp: 148.5–150.5° C.

NMR (DMSO-d$_6$, δ): 1.57 (3H, d, J=7.0 Hz), 3.81 (3H, s), 5.03 (1H, quint, J=7.0 Hz), 5.33 (2H, s), 5.55 (1H, d, J=7.0 Hz), 6.77 (1H, dd, J=7.0, 2.5 Hz), 7.07–7.14 (2H, m), 7.29–7.43 (3H, m), 7.50 (2H, d, J=7.0 Hz)

(2) To a solution of 4-benzyloxy-2-(1-hydroxyethyl)-1-methyl-1H-benzimidazole (87.0 mg) in dichloromethane (3 ml) was added manganese dioxide (870 mg) at 0° C. under nitrogen atmosphere, and the mixture was stirred for 30 minutes at 0° C. and then for 1.5 hours at ambient temperature. The reaction mixture was purified by silica gel column chromatography (ethyl acetate:n-hexane=3:1, v/v) to give 2-acetyl-4-benzyloxy-1-methyl-1H-benzimidazole (74.2 mg).

mp: 102–103.5° C.

NMR (CDCl$_3$, δ): 2.88 (3H, s), 4.11 (3H, s), 5.46 (2H, s), 6.72 (1H, d, J=8.5 Hz), 7.00 (1H, d, J=8.5 Hz), 7.23–7.41 (4H, m), 7.52 (2H, d, J=7.5 Hz)

Preparation 24

(1) 3-Benzyloxy-2-nitro-N-ethoxycarbonylacetyl-N-methylaniline was obtained from 3-benzyloxy-2-nitro-N-methylaniline and ethoxycarbonylacetyl chloride according to a similar manner to that of Preparation 22-(1).

NMR (CDCl$_3$, δ): 1.24 (3H, t, J=7.5 Hz), 3.21 (3H, s), 3.23 (2H, m), 4.15 (2H, m), 5.21 (2H, s), 6.99 (1H, d, J=7.5 Hz), 7.14 (1H, d, J=7.5 Hz), 7.32–7.52 (6H, m)

(2) 4-Benzyloxy-2-ethoxycarbonylmethyl-1-methyl-1H-benzimidazole was obtained according to a similar manner to that of Preparation 9.

mp: 105.5–106° C.

NMR (CDCl$_3$, δ): 1.28 (3H, t, J=7.0 Hz), 3.76 (3H, s), 4.06 (2H, s), 4.20 (2H, q, J=7.0 Hz), 5.37 (2H, s), 6.69 (1H, d, J=7.5 Hz), 6.93 (1H, d, J=7.5 Hz), 7.13 (1H, t, J=7.5 Hz), 7.25–7.39 (3H, m), 7.50 (2H, d, J=7.5 Hz)

Preparation 25

To a mixture of 3-benzyloxy-2-amino-N-methylaniline (200 mg) and methyl isothiocyanate (70.5 mg) was added tetrahydrofuran (2 ml) at ambient temperature, and the mixture was stirred for 2 days. The solvent was removed in vacuo, and the residue was dissolved in acetonitrile (2 ml). Methyl iodide (149 mg) was added thereto under ice-cooling, the mixture was stirred for 5 hours. The reaction mixture was concentrated in vacuo, and the residue was crystallized with ethyl acetate and recrystallized with acetonitrile to give 4-benzyloxy-1-methyl-2-methylamino-1H-benzimidazole (148 mg).

mp: 212.9° C.

NMR (CDCl$_3$—CD$_3$OD, δ): 3.12 (3H, s), 3.80 (3H, s), 5.20 (2H, s), 6.87 (2H, d, J=7.5 Hz), 7.22 (1H, t, J=7.5 Hz), 7.34–7.51 (5H, m)

Preparation 26

To a solution of 4-benzyloxy-1-methyl-2-methylamino-1H-benzimidazole (200 mg) in dimethylformamide (2 ml) was added sodium hydride (32.9 mg) under ice-cooling, and the mixture was stirred for 15 minutes. To the mixture was added methyl iodide (127 mg), and the mixture was stirred for 15 minutes under ice-cooling and then for 2 hours at ambient temperature. Water was added to the reaction mixture, and extracted with chloroform. The organic layer was dried over magnesium sulfate and evaporated in vacuo. The residue was purified by flash chromatography (chloroform:methanol=50:1, v/v) to give 4-benzyloxy-1-methyl-2-dimethylamino-1H-benzimidazole (100 mg).

NMR (CDCl$_3$, δ): 2.99 (6H, s), 3.61 (3H, s), 5.40 (2H, s), 6.60 (1H, d, J=8 Hz), 6.79 (1H, d, J=8 Hz), 6.98 (1H, t, J=8 Hz), 7.29–7.43 (3H, m), 7.50 (2H, d, J=8 Hz)

Preparation 27

A mixture of 3-benzyloxy-2-amino-N-methylaniline (600 mg), isobutyric acid (243 mg) and 4N hydrochloric acid (3.5 ml) was refluxed for 3 hours, and the solvent was removed in vacuo. Chloroform and saturated sodium bicarbonate solution were added to the residue. The separated organic layer was washed with water and brine, dried over magnesium sulfate and evaporated in vacuo. The residue was purified by silica gel column chromatography (chloroform:methanol=50:1, v/v) to give 4-hydroxy-2-isopropyl-1-methyl-1H-benzimidazole (33 mg).

NMR (CDCl$_3$, δ): 1.40 (6H, d, J=7.5 Hz), 3.20 (1H, m), 3.71 (3H, s), 6.75 (1H, d, J=8 Hz), 6.82 (1H, d, J=8 Hz), 7.13 (1H, t, J=8 Hz)

Preparation 28

(1) To a solution of 3-benzyloxy-2-amino-N-methylaniline (500 mg) and pentafluoropropionic acid (395 mg) in tetrahydrofuran (3 ml) was added 2-ethoxy-1-ethoxycarbonyl-1,2-dihydroquinoline (1.35 g), and the mixture was stirred for 4 hours at 50° C. To the mixture was further added 2-ethoxy-1-ethoxycarbonyl-1,2-dihydroquinoline (108 mg), and the mixture was stirred for 20 hours. The reaction mixture was concentrated in vacuo, and the residue was dissolved in ethyl acetate. The organic layer was washed with water and brine, dried over magnesium sulfate and evaporated in vacuo. The residue was purified by silica gel column chromatography to give a residue containing 3-benzyloxy-2-pentafluoropropionamido-N-methylaniline and 4-benzyloxy-2-pentafluoroethyl-1-methyl-1H-benzimidazole.

(2) To a solution of the residue obtained above (1) in dichloromethane was added phosphorus pentachloride (291 mg), and the mixture was refluxed for 1 hour. The reaction mixture was washed with water and brine, dried over magnesium sulfate and evaporated in vacuo. The residue was purified by silica gel column chromatography (chloroform) to give 4-benzyloxy-2-pentafluoroethyl-1-methyl-1H-benzimidazole (150 mg).

NMR (CDCl$_3$, δ): 3.92 (3H, s), 5.49 (2H, s), 6.75 (1H, d, J=8 Hz), 7.00 (1H, d, J=8 Hz), 7.22–7.40 (4H, m), 7.49 (2H, d, J=8 Hz)

Preparation 29

(1) 3-Benzyloxy-2-nitro-N-tert-butoxycarbonyl-N-(2-methoxyethyl)aniline was obtained from 3-benzyloxy-2-nitro-N-tert-butoxycarbonylaniline and 2-methoxyethyl chloride according to a similar manner to that of Preparation 3.

(2) 3-Benzyloxy-2-nitro-N-(2-methoxyethyl)aniline was obtained according to a similar manner to that of Preparation 5.

NMR (CDCl$_3$, δ): 3.35 (2H, q, J=6 Hz), 3.40 (3H, s), 3.61 (2H, t, J=6 Hz), 5.16 (2H, s), 6.21 (1H, t-like), 6.30–6.42 (2H, m), 7.20 (1H, t, J=8 Hz), 7.27–7.47 (5H, m)

Preparation 30

(1) 3-Benzyloxy-2-nitro-N-tert-butoxycarbonyl-N-(3-hydroxypropyl)aniline was obtained from 3-benzyloxy-2-nitro-N-tert-butoxycarbonylaniline and 3-hydroxypropyl bromide according to a similar manner to that of Preparation 3.

NMR (CDCl$_3$, δ): 1.35 (9H, br s), 1.68–1.81 (2H, m), 3.14 (1H, br s), 3.55–3.72 (3H, m), 3.80 (1H, br s), 5.20 (2H, br s), 6.81 (1H, br d, J=7.5 Hz), 7.01 (1H, d, J=7.5 Hz), 7.29–7.40 (6H, m)

(2) 3-Benzyloxy-2-nitro-N-(3-hydroxypropyl)aniline was obtained according to a similar manner to that of Preparation 5.

NMR (CDCl$_3$, δ): 1.43 (1H, t, J=6 Hz), 1.86–1.98 (2H, m), 3.15 (2H, q, J=6 Hz), 3.81 (2H, q, J=6 Hz), 5.15 (2H, br s), 6.28 (1H, br s), 6.32 (1H, d, J=7.5 Hz), 6.42 (1H, d, J=7.5 Hz), 7.21 (1H, t, J=7.5 Hz), 7.28–7.48 (5H, m)

(3) 2-Amino-3-benzyloxy-N-(3-hydroxypropyl)aniline was obtained according to a similar manner to that of Preparation 14-(2).

mp: 82–83° C.

NMR (CDCl$_3$, δ): 1.87–1.99 (2H, m), 3.30 (2H, t, J=6 Hz), 3.46 (2H, br s), 3.84 (2H, t, J=6 Hz), 5.08 (2H, s), 6.41 (1H, d, J=7.5 Hz), 6.49 (1H, d, J=7.5 Hz), 7.75 (1H, t, J=7.5 Hz), 7.28–7.47 (5H, m)

(4) To a solution of 2-amino-3-benzyloxy-N-(3-hydroxypropyl)aniline (100 mg) in chloroform (2 ml) was added 1,1'-thiocarbonyldiimidazole (72.7 mg) at ambient temperature, and the mixture was stirred for 2 hours at the same temperature and refluxed for 5 hours. The reaction mixture was washed with water and brine, dried over magnesium sulfate and evaporated in vacuo. The residue was purified by preparative thin layer chromatography (chloroform:methanol=10:1, v/v) to give 4-benzyloxy-1-(3-hydroxypropyl)-2-thioxo-2,3-dihydro-1H-benzimidazole (75 mg).

mp: 124–125° C.

NMR (CDCl$_3$, δ): 1.94–2.05 (2H, m), 3.48–3.58 (3H, m), 4.44 (2H, br t, J=6 Hz), 5.19 (2H, s), 6.79 (1H, d, J=7.5 Hz), 6.82 (1H, d, J=7.5 Hz), 7.14 (1H, t, J=7.5 Hz), 7.33–7.46 (5H, m), 9.63 (1H, br s)

(5) To a solution of 4-benzyloxy-1-(3-hydroxypropyl)-2-thioxo-2,3-dihydro-1H-benzimidazole (70 mg) in acetonitrile (2 ml) was added methyl iodide (37.9 mg), and the mixture was stirred overnight. The reaction mixture was concentrated in vacuo. The residue was purified by preparative thin layer chromatography and pulverized with diisopropyl ether to give 4-benzyloxy-1-(3-hydroxypropyl)-2-methylthio-1H-benzimidazole (67 mg).

mp: 106–107° C.

NMR (CDCl$_3$, δ): 1.99–2.10 (2H, m), 2.84 (3H, s), 3.59–3.68 (3H, m), 4.21 (2H, t, J=7 Hz), 5.42 (2H, s), 6.67 (1H, d, J=7.5 Hz), 6.92 (1H, d, J=7.5 Hz), 7.05 (1H, t, J=7.5 Hz), 7.28–7.40 (3H, m), 7.50 (2H, br d, J=7.5 Hz)

(6) To a solution of 4-benzyloxy-1-(3-hydroxypropyl)-2-methylthio-1H-benzimidazole (59 mg) in dimethylformamide (1 ml) was added sodium hydride at ambient temperature, and the mixture was stirred overnight. Water was added to the reaction mixture, and extracted with ethyl acetate. The extract was washed with water and brine, dried over magnesium sulfate and evaporated in vacuo. The residue was purified by preparative thin layer chromatography (chloroform:methanol=10:1, v/v) and pulverized with diisopropyl ether to give 9-benzyloxy-3,4-dihydro-2H-[1,3]oxazino-[3,2-a]benzimidazole (43 mg).

mp: 183–184° C.

NMR (CDCl$_3$, δ): 2.28–2.38 (2H, m), 4.09 (2H, t, J=7.5 Hz), 4.51 (2H, t, J=6 Hz), 5.41 (2H, s), 6.73 (1H, d, J=7.5 Hz), 6.79 (1H, d, J=7.5 Hz), 7.01 (1H, t, J=7.5 Hz), 7.23–7.38 (3H, m), 7.50 (2H, br d, J=7.5 Hz)

Preparation 31

(1) To a solution of 3-nitrobenzene-1,2-diol (600 mg) in methanol (6 ml) was added 10% palladium on carbon (60 mg), and the mixture was stirred for 3 hours at ambient temperature under hydrogen atmosphere. Insoluble material was filtered off, and the filtrate was concentrated in vacuo. The residue was crystallized with diisopropyl ether to give 3-aminobenzene-1,2,-diol (470 mg).

mp: 163–166° C.

NMR (DMSO-d$_6$, δ): 4.30 (2H, br s), 6.01–6.13 (2H, m), 6.34 (1H, t, J=8 Hz)

(2) 3-Aminobenzene-1,2-diol (450 mg) was dissolved in 10% hydrogen chloride-methanol solution (1 ml), and the solvent was removed. The residue was dissolved in ethanol, and acetamide (227 mg) was added thereto. The mixture was heated at 180° C. for 2 hours. After cooling, chloroform and methanol were added thereto, and insoluble material was filtered off. The filtrate was washed with saturated sodium bicarbonate solution, dried over magnesium sulfate and evaporated in vacuo. The residue was purified by flash chromatography (chloroform:methanol=40:1, v/v) to give 7-hydroxy-2-methylbenzoxazole (183 mg).

mp: 152–154° C.

NMR (CDCl$_3$, δ): 2.65 (3H, s), 6.41 (1H, br s), 6.85 (1H, d, J=7.5 Hz), 7.16 (1H, t, J=7.5 Hz), 7.24 (1H, d, J=7.5 Hz)

Preparation 32

(1) To a solution of 3-nitrobenzene-1,2-diol (2.78 g) and 3,4-dihydro-2H-pyrane (1.81 g) in benzene (39 ml) was added p-toluenesulfonic acid monohydrate (5 mg) at ambient temperature, and the mixture was stirred for 24 hours. The reaction mixture was washed with saturated sodium bicarbonate solution, dried over magnesium sulfate and evaporated in vacuo. The residue was purified by silica gel column chromatography (chloroform-methanol) and crystallized with n-hexane to give 2-nitro-6-(tetrahydropyran-2-yloxy)phenol (2.32 g).

mp: 72–75° C.

NMR (CDCl$_3$, δ): 1.59–1.80 (3H, m), 1.85–2.17 (3H, m), 3.62 (1H, dt, J=10, 4 Hz), 3.97 (1H, dt, J=10, 4 Hz), 5.48 (1H, t, J=4 Hz), 6.89 (1H, t, J=7.5 Hz), 7.43 (1H, d, J=7.5 Hz), 7.78 (1H, d, J=7.5 Hz)

(2) 2-Amino-6-(tetrahydropyran-2-yloxy)phenol was obtained according to a similar manner to that of Preparation 31-(1).

mp: 163–166° C.

NMR (CDCl$_3$, δ): 1.48–1.70 (3H, m), 1.77–2.02 (3H, m), 3.57–3.66 (1H, m), 3.75 (2H, br s), 3.98–4.07 (1H, m), 5.08–5.13 (1H, m), 6.46 (1H, d, J=7.5 Hz), 6.50 (1H, d, J=7.5 Hz), 6.63 (1H, t, J=7.5 Hz), 6.70 (1H, br s)

(3) To a solution of 2-amino-6-(tetrahydropyran-2-yloxy) phenol (2.0 g) in anhydrous tetrahydrofuran (30 ml) was added 1,1'-carbonyldiimidazole (2.03 g), and the mixture was refluxed for 2 hours under nitrogen atmosphere. After cooling, the reaction mixture was concentrated in vacuo. The residue was purified by flash chromatography (chloroform:methanol=40:1, v/v) and crystallized with diisopropyl ether to give 7-(tetrahydropyran-2-yloxy)-2 (3H)-benzoxazolone (1.96 g).

mp: 174–176° C.

NMR (CDCl$_3$, δ): 1.55–2.14 (6H, m), 3.58–3.68 (1H, m), 3.95 (1H, dt, J=10, 2 Hz), 5.63 (1H, br s), 6.71 (1H, d, J=7.5 Hz), 6.92 (1H, d, J=7.5 Hz), 7.06 (1H, t, J=7.5 Hz), 8.49 (1H, br s)

(4) To a suspension of 7-(tetrahydropyran-2-yloxy)-2 (3H)-benzoxazolone (300 mg) and potassium carbonate (529 mg) in dimethylformamide (3 ml) was added methyl iodide at ambient temperature, and the mixture was stirred for 3 hours under nitrogen atmosphere. Water was added to the reaction mixture, and the resulting precipitates were collected by filtration to give 3-methyl-7-(tetrahydropyran-2-yloxy)-2(3H)-benzoxazolone (299 mg).

mp: 128–129° C.

NMR (CDCl$_3$, δ): 1.57–1.78 (3H, m), 1.81–2.13 (3H, m), 3.39 (3H, s), 3.58–3.67 (1H, m), 3.94 (1H, dt, J=10, 2 Hz), 5.64 (1H, br s), 6.62 (1H, d, J=7.5 Hz), 6.92 (1H, d, J=7.5 Hz), 7.09 (1H, t, J=7.5 Hz)

(5) To a suspension of 3-methyl-7-(tetrahydropyran-2-yloxy)-2(3H)-benzoxazolone (280 mg) in methanol (2.3 ml) was added 1N hydrochloric acid (0.5 ml) at ambient temperature, and the mixture was stirred for 30 minutes. The reaction mixture was concentrated to ⅓ volume, and water was added thereto. The mixture was extracted with chloroform, and the extract was dried over magnesium sulfate and concentrated in vacuo. The residue was crystallized with diisopropyl ether to give 7-hydroxy-3-methyl-2 (3H)-benzoxazolone (164 mg).

mp: 209–211° C.

NMR (DMSO-d$_6$, δ) 3.30 (3H, s), 6.63 (1H, d, J=7.5 Hz), 6.68 (1H, d, J=7.5 Hz), 7.01 (1H, t, J=7.5 Hz)

Preparation 33

(1) 3-Ethoxycarbonylmethyl-7-(tetrahydropyran-2-yloxy)-2(3H)-benzoxazolone was obtained from 7-(tetrahydropyran-2-yloxy)-2(3H)-benzoxazolone and ethyl bromoacetate according to a similar manner to that of Preparation 32-(4).

mp: 92–93° C.

NMR (CDCl$_3$, δ) 1.29 (3H, t, J=7.5 Hz), 1.53–1.79 (3H, m), 1.81–2.15 (3H, m), 3.59–3.69 (1H, m), 3.96 (1H, dt, J=10, 2 Hz), 4.26 (2H, q, J=7.5 Hz), 4.53 (2H, s), 5.64 (1H, br s), 6.55 (1H, d, J=7.5 Hz), 6.95 (1H, d, J=7.5 Hz), 7.09 (1H, t, J=7.5 Hz)

(2) 3-Ethoxycarbonylmethyl-7-hydroxy-2(3H)-benzoxazolone was obtained according to a similar manner to that of Preparation 32-(5).

mp: 150–152° C.

NMR (CDCl$_3$, δ) 1.29 (3H, t, J=7.5 Hz), 4.26 (2H, q, J=7.5 Hz), 4.54 (2H, s), 6.11 (1H, br s), 6.48 (1H, d, J=7.5 Hz), 6.75 (1H, d, J=7.5 Hz), 7.05 (1H, t, J=7.5 Hz)

Preparation 34

The following compounds were obtained according to a similar manner to that of Preparation 11.

(1) 2-Ethoxy-4-hydroxy-1-methyl-1H-benzimidazole mp: 163.5–165° C.

NMR (CDCl$_3$, δ): 1.43 (3H, t, J=6.5 Hz), 3.51 (3H, s), 4.54 (2H, q, J=6.5 Hz), 6.71 (2H, t, J=8.5 Hz), 7.03 (1H, t, J=8.5 Hz), 8.05 (1H, br s)

(2) 4-Hydroxy-2-methoxymethyl-1-methyl-1H-benzimidazole mp: 162.5–163° C.

NMR (CDCl$_3$, δ): 3.33 (3H, s), 3.81 (3H, s), 4.81 (2H, s), 6.85 (1H, d, J=8.5 Hz), 6.87 (1H, d, J=8.5 Hz), 7.22 (1H, t, J=8.5 Hz)

(3) 2-Acetyl-4-hydroxy-1-methyl-1H-benzimidazole mp: 154–155° C.

NMR (CDCl$_3$, δ): 2.80 (3H, s), 4.11 (3H, s), 6.83 (1H, d, J=8.5 Hz), 6.96 (1H, d, J=8.5 Hz), 7.33 (1H, t, J=8.5 Hz)

(4) 2-Ethoxycarbonylmethyl-4-hydroxy-1-methyl-1H-benzimidazole mp: 166.5–182° C.

NMR (CDCl$_3$, δ): 1.23 (3H, t, J=7.0 Hz), 3.72 (3H, s), 4.13 (2H, s), 4.17 (2H, q, J=7.0 Hz), 6.81 (1H, d, J=8.5 Hz), 6.84 (1H, d, J=8.5 Hz), 7.19 (1H, t, J=8.5 Hz)

(5) 2-Amino-3-hydroxy-N-methylaniline mp: 94–97° C.

NMR (DMSO-d$_6$, δ): 2.68 (3H, d, J=4.5 Hz), 3.80 (2H, br s), 4.52 (1H, q, J=4.5 Hz), 5.98 (1H, d, J=8.5 Hz), 6.13 (1H, d, J=8.5 Hz), 6.38 (1H, t, J=8.5 Hz), 8.73 (1H, br s)

(6) 4-Hydroxy-1-methyl-2-dimethylamino-1H-benzimidazole mp: 177–179° C.

NMR (CDCl$_3$, δ): 2.93 (6H, s), 3.60 (3H, s), 6.71 (2H, br d, J=8 Hz), 7.03 (1H, t, J=8 Hz)

(7) 2-Pentafluoroethyl-4-hydroxy-1-methyl-1H-benzimidazole

NMR (CDCl$_3$—CD$_3$OD, δ): 3.93 (3H, s), 6.86 (1H, d, J=8 Hz), 6.98 (1H, d, J=8 Hz), 7.34 (1H, t, J=8 Hz)

(8) 2-Amino-3-hydroxy-N-(2-methoxyethyl)aniline

NMR (CDCl$_3$, δ): 3.24–3.35 (2H, m), 3.40 (3H, s), 3.64 (2H, t, J=6 Hz), 6.25–6.37 (2H, m), 6.74 (1H, t, J=8 Hz)

(9) 2-Amino-3-hydroxy-N-ethylaniline (from 3-benzyloxy-2-nitro-N-ethylaniline)

NMR (CDCl$_3$, δ): 1.30 (3H, t, J=7 Hz), 3.16 (2H, q, J=7 Hz), 6.29 (2H, d, J=8 Hz), 6.74 (1H, t, J=8 Hz)

Preparation 35

To a suspension of 4-benzyloxy-1-methyl-2-methylamino-1H-benzimidazole (150 mg) in dichloromethane (2 ml) was added boron tribromide-methyl sulfide complex (211 mg) in dryice-aceton bath, and the mixture was stirred for 1 hour under ice-cooling and then at ambient temperature overnight. To the reaction mixture were added chloroform-methanol (3:1, v/v) and saturated sodium bicarbonate solution, and insoluble material was filtered off. The separated organic layer was concentrated in vacuo. The residue was purified by preparative thin layer chromatography (chloroform:methanol=8:1, v/v) to give 4-hydroxy-1-methyl-2-methylamino-1H-benzimidazole (49 mg).

NMR (CDCl$_3$—CD$_3$OD, δ): 3.09 (3H, s), 3.48 (3H, s), 6.60 (1H, d, J=7.5 Hz), 6.69 (1H, d, J=7.5 Hz), 6.98 (1H, t, J=7.5 Hz)

Preparation 36

(1) To a solution of sodium hydroxide (830 mg) in dimethylsulfoxide (100 ml) was added (4-methoxycarbonylbenzyl)triphenylphosphonium bromide (10.0 g), and after 30 minutes, 4-pyridinecarbaldehyde (2.22 g) was added thereto under ice-cooling. The mixture was stirred overnight. Water was added to the reaction mixture, and extracted with ethyl acetate. The organic layer was washed with water and brine, dried over magnesium sulfate and concentrated in vacuo. The residue was purified by flash chromatography (n-hexane-ethyl acetate) to give methyl 4-[(E)-2-(4-pyridyl)vinyl]benzoate (1.18 g) and methyl 4-[(Z)-2-(4-pyridyl)vinyl]benzoate (2.67 g).

Methyl 4-[(E)-2-(4-pyridyl)vinyl]benzoate mp: 152–154° C.

NMR (CDCl$_3$, δ): 3.93 (3H, s), 7.11 (1H, d, J=16 Hz), 7.32 (1H, d, J=16 Hz), 7.39 (2H, d, J=6 Hz), 7.60 (2H, d, J=7.5 Hz), 8.06 (2H, d, J=7.5 Hz), 8.61 (2H, d, J=6 Hz)

Methyl 4-[(Z)-2-(4-pyridyl)vinyl]benzoate

NMR (CDCl$_3$, δ): 3.90 (3H, s), 6.61 (1H, d, J=12 Hz), 6.82 (1H, d, J=12 Hz), 7.08 (2H, d, J=6 Hz), 7.28 (2H, d, J=7.5 Hz), 7.93 (2H, d, J=7.5 Hz), 8.48 (2H, d, J=6 Hz)

(2) To a suspension of lithium aluminum hydride (92.8 mg) in tetrahydrofuran (12 ml) was added methyl 4-[(E)-2-(4-pyridyl)vinyl]benzoate (1.17 g), and after stirring for 2 hours at ambient temperature, ammonia solution and methanol were added thereto. The mixture was stirred for 2 hours at ambient temperature. Insoluble material was filtered off, and the filtrate was washed with water and brine, dried over magnesium sulfate and concentrated in vacuo. The residue was crystallized with diisopropyl ether to give 4-[(E)-2-(4-pyridyl)vinyl]benzyl alcohol (762 mg).

mp: 211–213° C.

NMR (DMSO-d$_6$, δ): 4.51 (2H, d, J=5 Hz), 5.23 (1H, t, J=5 Hz), 7.22 (1H, d, J=16 Hz), 7.37 (2H, d, J=7.5 Hz), 7.49–7.59 (3H, m), 7.62 (2H, d, J=7.5 Hz), 8.53 (2H, d, J=6 Hz)

(3) To a solution of 4-[(E)-2-(4-pyridyl)vinyl]benzyl alcohol (740 mg) and triethylamine (1.77 g) in dimethyl sulfoxide (3 ml) was added sulfur trioxide-pyridine complex (1.11 g) at ambient temperature, and after stirring for 4 hours, water was added thereto. The mixture was extracted with ethyl acetate, and the extract was washed with water and brine, dried over magnesium sulfate and concentrated in vacuo. The residue was purified by flash chromatography (chloroform-ethyl acetate) and crystallized with diisopropyl ether to give 4-[(E)-2-(4-pyridyl)vinyl]-benzaldehyde (518 mg).

mp: 116–117° C.

NMR (CDCl$_3$, δ) 7.16 (1H, d, J=16 Hz), 7.33 (1H, d, J=16 Hz), 7.40 (2H, d, J=6 Hz), 7.69 (2H, d, J=7.5 Hz), 7.90 (2H, d, J=7.5 Hz), 8.62 (2H, d, J=6 Hz)

(4) To a solution of 4-[(E)-2-(4-pyridyl)vinyl]benzaldehyde (50 mg) in pyridine (0.025 ml) and ethanol (0.075 ml) was added malonic acid (27.4 mg), and the mixture was refluxed for 7 hours. After cooling, ethyl acetate was added thereto, the resulting precipitates were collected by filtration to give 4-[(E)-2-(4-pyridyl)vinyl]cinnamic acid (28 mg).

mp: >300° C.

NMR (DMSO-d$_6$, δ): 6.58 (1H, d, J=15 Hz), 7.35 (1H, d, J=16 Hz), 7.53–7.64 (4H, m), 7.70 (2H, d, J=7.5 Hz), 7.76 (2H, d, J=7.5 Hz), 8.56 (2H, d, J=6 Hz)

Preparation 37

(1) To a solution of methyl 4-[(Z)-2-(4-pyridyl)vinyl]-benzoate (570 mg) in methanol (5.7 ml) was added 10% palladium on carbon, and the mixture was stirred for 4 hours at ambient temperature under hydrogen atmosphere. Insoluble material was filtered off, and the filtrate was concentrated in vacuo. The residue was crystallized with n-hexane to give methyl 4-[2-(4-pyridyl)ethyl]benzoate (539 mg).

mp: 62–64° C.

NMR (CDCl$_3$, δ) 1.81 (1H, br s), 2.91 (4H, s), 4.68 (2H, br d, J=5 Hz), 7.08 (2H, d, J=6 Hz), 7.15 (2H, d, J=7.5 Hz), 7.29 (2H, d, J=7.5 Hz), 8.48 (2H, br d, J=6 Hz)

(2) 4-[2-(4-Pyridyl)ethyl]benzyl alcohol was obtained according to a similar manner to that of Preparation 36-(2).

mp: 163–166° C.

NMR (CDCl$_3$, δ): 2.96–3.04 (4H, m), 3.90 (3H, s), 7.12 (2H, d, J=6 Hz), 7.20 (2H, d, J=7.5 Hz), 7.96 (2H, d, J=7.5 Hz), 8.50 (2H, br d, J=6 Hz)

(3) 4-[2-(4-Pyridyl)ethyl]benzaldehyde was obtained according to a similar manner to that of Preparation 36-(3).

NMR (CDCl$_3$, δ): 2.90–3.08 (4H, m), 7.06 (2H, d, J=6 Hz), 7.30 (2H, d, J=7.5 Hz), 7.80 (2H, d, J=7.5 Hz), 8.49 (2H, br d, J=6 Hz)

(4) 4-[2-(4-Pyridyl)ethyl]cinnamic acid was obtained according to a similar manner to that of Preparation 36-(4).

mp: >300° C.

NMR (DMSO-d$_6$, δ): 2.91 (4H, br s), 6.47 (1H, d, J=15 Hz), 7.20–7.30 (4H, m), 7.49–7.62 (3H, m), 8.43 (2H, d, J=6 Hz)

Preparation 38

(1) To a solution of 2-amino-5-bromo-3-methylpyridine (300 mg) in N,N-dimethylaniline (486 mg) was added acetyl chloride (138 mg), and the mixture was stirred for 3 hours at 70° C. The reaction mixture was poured into water, and extracted with ethyl acetate. The extract was washed with water and brine, dried over magnesium sulfate and evaporated in vacuo. The residue was purified by silica gel column chromatography (chloroform) to give 2-acetamido-5-bromo-3-methylpyridine (120 mg).

NMR (CDCl$_3$, δ): 2.25 (6H, s-like), 7.50 (1H, br s), 7.70 (1H, d, J=2 Hz), 8.29 (1H, d, J=2 Hz)

(2) To a solution of 2-acetamido-5-bromo-3-methylpyridine (110 mg) and tri-n-butylamine (196 mg) in xylene were added palladium(II) acetate (1 mg) and triphenylphosphine (1 mg) under nitrogen atmosphere, and the mixture was heated at 150° C. Acrylic acid (41.5 mg) was added thereto, and the mixture was stirred for 7 hours at the same temperature. After cooling to ambient temperature, ethyl acetate and saturated sodium bicarbonate solution were added to the reaction mixture, and separated aqueous layer was adjusted to pH 4 with 4N hydrochloric acid. The mixture was extracted with chloroform. The extract was washed with water and brine, dried over magnesium sulfate and evaporated in vacuo. The residue was collected by filtration and washed with diisopropyl ether to give (E)-3-(6-acetamido-5-methylpyridin-3-yl)acrylic acid (89 mg).

NMR (CDCl$_3$, δ): 2.03 (3H, s), 2.14 (3H, s), 6.46 (1H, d, J=16 Hz), 7.09 (1H, d, J=16 Hz), 7.81 (1H, s-like), 8.30 (1H, s-like)

Preparation 39

The following compounds were obtained according to a similar manner to that of Example 9.

(1) 3-[2,6-Dimethyl-3-[N-[4-(methylcarbamoyl) cinnamoylglycyl]-N-methylamino]benzyloxy]-2-amino-N-methylaniline (from 3-hydroxy-2-amino-N-methylaniline and 2,6-dimethyl-3-[N-[4-(methylcarbamoyl) cinnamoylglycyl]-N-methylamino]benzyl chloride)

NMR (DMSO-d$_6$, δ) 2.24 (3H, s), 2.40 (3H, s), 2.71 (3H, d, J=5.5 Hz), 2.79 (3H, d, J=5.5 Hz), 3.10 (3H, s), 3.50 (1H, dd, J=16.5, 5.5 Hz), 3.67 (1H, dd, J=16.5, 5.5 Hz), 3.96 (2H, br s), 4.68 (1H, q, J=5.5 Hz), 5.03 (2H, s), 6.20 (1H, d, J=7.5 Hz), 6.49–6.59 (2H, m), 6.88 (1H, d, J=16.0 Hz), 7.22 (1H, d, J=8.5 Hz), 7.27 (1H, d, J=8.5 Hz), 7.42 (1H, d, J=16.0 Hz), 7.63 (2H, d, J=8.5 Hz), 7.85 (2H, d, J=8.5 Hz), 8.25 (1H, t, J=4.5 Hz), 8.48 (1H, q, J=4.5 Hz)

(2) 3-[3-[N-[(E)-3-(6-Acetamidopyridin-3-yl) acryloylglycyl]-N-methylamino]-2,6-dichlorobenzyloxy]-2-aminoaniline (from 3-hydroxy-2-aminoaniline and 3-[N-[(E)-3-(6-acetamidopyridin-3-yl)acryloylglycyl]-N-methylamino]-2,6-dichlorobenzyl chloride)

NMR (CDCl$_3$, δ): 2.22 (3H, s), 3.28 (3H, s), 3.50 (4H, br s), 3.69 (1H, dd, J=17, 4 Hz), 3.94 (1H, dd, J=17, 5 Hz), 5.34 (2H, s), 6.40–6.50 (2H, m), 6.60–6.76 (3H, m), 7.32 (1H, d, J=7.5 Hz), 7.50 (1H, d, J=7.5 Hz), 7.53 (1H, d, J=15 Hz), 7.85 (1H, dd, J=7.5, 2 Hz), 7.27–7.36 (4H, m), 7.49 (1H, d, J=7.5 Hz), 7.51 (1H, d, J=15 Hz), 7.84 (1H, br d, J=7.5 Hz), 8.09 (1H, br s), 8.22 (1H, br d, J=7.5 Hz), 8.36 (1H, br s)

(3) 2-Amino-3-[3-[N-[(E)-3-(6-acetamidopyridin-3-yl)-acryloylglycyl]-N-methylamino]-2,6-dichlorobenzyloxy]-N-ethylaniline (from 3-hydroxy-2-amino-N-ethylaniline and 3-[N-[(E)-3-(6-acetamidopyridin-3-yl)acryloylglycyl]-N-methylamino]-2,6dichlorobenzyl chloride)

(This compound was used as a starting compound of Example 18-(2) without purification.)

(4) 3-[3-[N-[(E)-3-(6-Acetamidopyridin-3-yl) acryloylglycyl]-N-methylamino]-2,6-dichlorobenzyloxy]-2-amino-N-methylaniline (from 3-hydroxy-2-amino-N-methylaniline and 3-[N-[(E)-3-(6-acetamidopyridin-3-yl) acryloylglycyl]-N-methylamino]-2,6-dichlorobenzyl bromide)

(This compound was used as a starting compound of Example 18-(3) without purification.)

Preparation 40

(1) 3-[N-[(E)-3-(6-Acetamidopyridin-3-yl) acryloylglycyl]-N-methylamino]-1-(tert-butyldiphenylsilyloxymethyl)-2,6-dichlorobenzene was obtained from 3-(N-glycyl-N-methylamino)-1-(tert-butyldiphenylsilyloxymethyl)-2,6-dichlorobenzene and (E)-3-(6-acetamidopyridin-3-yl)acrylic acid according to a similar manner to that of Preparation 16-(2).

mp: 194–196° C.

NMR (CDCl$_3$, δ): 1.06 (9H, s), 2.22 (3H, s), 3.23 (3H, s), 3.57 (1H, dd, J=17, 4 Hz), 3.94 (1H, dd, J=17, 5 Hz), 4.92 (1H, d, J=10 Hz), 4.98 (1H, d, J=10 Hz), 6.44 (1H, d, J=15 Hz), 6.63 (1H, br s), 7.22 (1H, d, J=8 Hz), 7.35–7.48 (6H, m), 7.52 (1H, d, J=15 Hz), 7.70–7.77 (4H, m), 7.83 (1H, dd, J=8, 3 Hz), 8.05 (1H, br s), 8.22 (1H, d, J=8 Hz), 8.36 (1H, d, J=3 Hz)

(2) 3-[N-[(E)-3-(6-Acetamidopyridin-3-yl) acryloylglycyl]-N-methylamino]-1-hydroxymethyl-2,6-dichlorobenzene was obtained according to a similar manner to that of Preparation 16-(3).

mp: 207–209° C.

NMR (DMSO-d$_6$, δ): 2.10 (3H, s), 3.10 (3H, s), 3.47 (1H, dd, J=17, 4 Hz), 3.76 (1H, dd, J=17, 5 Hz), 4.74 (1H, d, J=5 Hz), 5.35 (1H, br s), 6.79 (1H, d, J=15 Hz), 7.37 (1H, d, J=15 Hz), 7.61 (1H, d, J=8 Hz), 7.65 (1H, d, J=8 Hz), 7.98 (1H, dd, J=8, 3 Hz), 8.11 (1H, d, J=8 Hz), 8.21 (1H, t, J=5 Hz), 8.47 (1H, s)

(3) 3-[N-[(E)-3-(6-Acetamidopyridin-3-yl) acryloylglycyl]-N-methylamino]-2,6-dichlorobenzyl bromide was obtained according to a similar manner to that of Preparation 16-(4).

mp: 222–223° C.

NMR (CDCl$_3$—CD$_3$OD, δ): 2.22 (3H, s), 3.27 (3H, s), 3.60 (1H, dd, J=17, 3 Hz), 3.94 (1H, dd, J=17, 3 Hz), 4.78 (2H, s), 6.49 (1H, d, J=15 Hz), 7.31 (1H, d, J=8 Hz), 7.49 (1H, d, J=8 Hz), 7.51 (1H, d, J=15 Hz), 7.88 (1H, dd, J=8, 3 Hz), 8.23 (1H, br d, J=8 Hz), 8.33 (1H, d, J=3 Hz)

Preparation 41

4-Acetamido-3-methylcinnamic acid was obtained from 4-acetamido-3-methylbenzaldehyde and malonic acid according to a similar manner to that of Preparation 36-(4).

mp: 262–263° C. (dec.)

NMR (DMSO-d$_6$, δ): 2.09 (3H, s), 2.23 (3H, s), 6.43 (1H, d, J=16 Hz), 7.43–7.61 (4H), 9.33 (1H, s)

Preparation 42

5-Hydroxymethyl-2-[(E)-2-(4-pyridyl)vinyl]pyridine was obtained from methyl 2-[(E)-2-(4-pyridyl)vinyl]pyridin-5-carboxylate according to a similar manner to that of Preparation 36-(2).

mp: >198.9° C.

NMR (CDCl$_3$, δ): 4.73 (2H, s), 7.34 (1H, d, J=16 Hz), 7.40–7.49 (3H, m), 7.53 (1H, d, J=16 Hz), 8.53–8.65 (3H, m)

Preparation 43

(1) To a solution of methyl 3,4-dihydro-2(1H)-quinolinone-6-carboxylate (500 mg) in tetrahydrofuran was dropwise added 2M solution of borane-methyl sulfide complex in tetrahydrofuran (2.5 ml) under ice-cooling, and the mixture was refluxed for 45 minutes. After cooling, methanol (1 ml) was dropwise added thereto, and the mixture was stirred for 1 hour. The solvent was removed, and ethyl acetate and water were added to the residue. The organic layer was washed with water, saturated sodium bicarbonate solution and brine, dried over magnesium sulfate and concentrated in vacuo. The residue was pulverized with diisopropyl ether-n-hexane to give methyl 1,2,3,4-tetrahydroquinoline-6-carboxylate as solid.

mp: 75–84° C.

NMR (CDCl$_3$, δ): 2.93 (2H, quint, J=7 Hz), 2.76 (2H, t, J=7 Hz), 3.33 (2H, t, J=7 Hz), 3.83 (3H, s), 4.29 (1H, br s), 6.39 (1H, d, J=8 Hz), 7.59–7.68 (2H, m)

(2) 6-Hydroxymethyl-1,2,3,4-tetrahydroquinoline was obtained according to a similar manner to that of Preparation 36-(2).

NMR (CDCl$_3$, δ): 1.53 (1H, t, J=6 Hz), 1.90 (2H, quint, J=7 Hz), 2.73 (2H, t, J=7 Hz), 3.28 (2H, t, J=7 Hz), 4.49 (2H, d, J=6 Hz), 6.44 (1H, d, J=8 Hz), 6.90–7.00 (2H, m)

(3) To a solution of 6-hydroxymethyl-1,2,3,4-tetrahydroquinoline (314 mg) in methanol (4 ml) was dropwise added acetic anhydride (589 mg) under ice-cooling, and the mixture was stirred for 1 hour at the same temperature. The solvent was removed in vacuo, and ethyl acetate and saturated sodium bicarbonate solution were added to the residue. The organic layer was washed with water and brine, dried and concentrated in vacuo. The residue was purified by preparative thin-layer chromatography (n-hexane:ethyl acetate =1:2, v/v) to give 1-acetyl-6-hydroxymethyl-1,2,3,4-tetrahydroquinoline (227 mg).

mp: 95–106° C.

NMR (CDCl$_3$, δ): 1.70 (1H, t-like), 1.96 (2H, quint, J=7 Hz), 2.24 (3H, s), 2.75 (2H, t, J=7 Hz), 3.80 (2H, t, J=7 Hz), 4.67 (2H, d, J=6 Hz), 6.96–7.36 (3H, m)

Preparation 44

(1) A mixture of 3-methoxy-4-nitrobenzyl alcohol (1.0 g) and 10% palladium on carbon (100 mg) in methanol was stirred for 2 hours under 3 atmospheric pressure of hydrogen. After filtration, the filtrate was concentrated in vacuo to give 4-amino-3-methoxybenzyl alcohol (910 mg) as an oil.

NMR (CDCl$_3$, δ): 3.77 (2H, br s), 3.84 (3H, s), 4.56 (2H, s), 6.66 (1H, d, J=8 Hz), 6.76 (1H, d, J=8 Hz), 6.81 (1H, s)

(2) To a solution of 4-amino-3-methoxybenzyl alcohol (900 mg) in methanol was added acetic anhydride (1.8 g) under ice cooling, and the mixture was stirred for 1 hour at the same temperature. After evaporation, the residue was dissolved in ethyl acetate, and the solution was washed with sodium bicarbonate solution, water and brine, dried over magnesium sulfate and concentrated in vacuo to give 4-acetamido-3-methoxybenzyl alcohol (840 mg) as solid.

mp: 104° C.

NMR (CDCl$_3$, δ): 1.69 (1H, t, J=5 Hz), 2.20 (3H, s), 3.90 (3H, s), 4.65 (2H, d, J=5 Hz), 6.88–6.97 (2H, n), 7.74 (1H, br s), 8.32 (1H, d, J=8 Hz)

Preparation 45

The following compounds were obtained according to a similar manner to that of Preparation 36-(3).

(1) 1-Acetyl-6-formyl-1,2,3,4-tetrahydroquinoline

NMR (CDCl$_3$, δ): 2.01 (2H, quint, J=7 Hz), 2.29 (3H, s), 2.82 (2H, t, J=7 Hz), 3.81 (2H, t, J=7 Hz), 7.46–7.60 (1H, br peak), 7.65–7.74 (2H, m), 9.93 (1H, s)

(2) 4-Acetamido-3-methoxybenzaldehyde mp: 145° C.

NMR (CDCl$_3$, δ): 2.25 (3H, s), 3.97 (3H, s), 7.41 (1H, d, J=2 Hz), 7.48 (1H, dd, J=2, 8 Hz), 7.99 (1H, br s), 8.59 (1H, d, J=8 Hz), 9.88 (1H, s)

(3) 5-Formyl-2-[(E)-2-(4-pyridyl)vinyl]pyridine mp: 131–136° C.

NMR (CDCl$_3$, δ): 7.40 (1H, d, J=16 Hz), 7.47 (2H, d, J=6 Hz), 7.56 (1H, d, J=8 Hz), 7.78 (1H, d, J=16 Hz), 8.19 (1H, dd, J=2, 8 Hz), 8.65 (2H, d, J=6 Hz), 9.07 (1H, d, J=2 Hz), 10.12 (1H, s)

Preparation 46

The following compounds were obtained according to a similar manner to that of Preparation 36-(4).

(1) (E)-3-(1-Acetyl-1,2,3,4-tetrahydroquinolin-6-yl)acrylic acid

NMR (DMSO-d$_6$, δ): 1.85 (2H, quint, J=7 Hz), 2.17 (3H, s), 2.73 (2H, t, J=7 Hz), 3.68 (2H, t, J=7 Hz), 6.46 (1H, d, J=16 Hz), 7.41–7.63 (4H, m)

(2) 4-Acetamido-3-methoxycinnamic acid mp: 221.5–230° C.

NMR (DMSO-d$_6$, δ): 2.10 (3H, s), 3.89 (3H, s), 6.52 (1H, d, J=16 Hz), 7.20 (1H, d, J=8 Hz), 7.38 (1H, s-like), 7.53 (1H, d, J=16 Hz), 8.07 (1H, d, J=8 Hz), 9.26 (1H, s)

(3) (E)-3-[6-[(E)-2-(4-Pyridyl)vinyl]pyridin-3-yl]acrylic acid mp: >250° C.

NMR (DMSO-d$_6$, δ): 6.71 (1H, d, J=16 Hz), 7.56–7.77 (6H, m), 8.20 (1H, dd, J=2, 8 Hz), 8.59 (2H, d, J=6 Hz), 8.88 (1H, d, J=2 Hz)

Preparation 47

(1) 4-Formyl-2-methoxybenzoic acid was obtained from 4-hydroxymethyl-2-methoxybenzoic acid according to a similar manner to that of Preparation 36-(3).

NMR (CDCl$_3$, δ): 4.04 (3H, s), 7.47–7.55 (2H, m), 8.04 (1H, d, J=8 Hz), 10.21 (1H, s)

(2) To a solution of 4-formyl-2-methoxybenzoic acid in tetrahydrofuran was added methyl (triphenylphosphranilidene)acetate at ambient temperature, and the mixture was stirred for 1 hour and then concentrated in vacuo. Ethyl acetate and saturated sodium bicarbonate solution were added to the residue, and separated aqueous layer was adjusted to pH 4 with 4N hydrochloric acid. The mixture was extracted with ethyl acetate. The extract was washed with water and brine, dried over magnesium sulfate and evaporated in vacuo. The residue was washed with hot diisopropyl ether to give methyl 4-carboxy-3-methoxycinnamate.

NMR (CDCl$_3$, δ): 3.84 (3H, s), 4.13 (3H, s), 6.54 (1H, d, J=16 Hz), 7.14 (1H, s), 7.31 (1H, d, J=8 Hz), 7.67 (1H, d, J=16 Hz), 8.21 (1H, d, J=8 Hz)

(3) Methyl 3-methoxy-4-methylcarbamoylcinnamate was obtained from methyl 4-carboxy-3-methoxycinnamate and methylamine hydrochloride according to a similar manner to that of Example 26.

NMR (CDCl$_3$, δ): 3.01 (3H, d, J=5 Hz), 3.82 (3H, s), 4.00 (3H, s), 6.48 (1H, d, J=16 Hz), 7.07 (1H, s), 7.25 (1H, d, J=8 Hz), 7.67 (1H, d, J=16 Hz), 7.78 (1H, br s), 8.24 (1H, d, J=8 Hz)

(4) To a solution of methyl 3-methoxy-4-methylcarbamoyl-cinnamate (300 mg) in methanol was added 1N sodium hydroxide solution (1.5 ml) at ambient temperature, and the mixture was stirred at 50° C. for 5 hours. The solvent was distilled off, and the residue was dissolved in water. The solution was washed with diethyl ether, and adjusted to pH 4 with 1N hydrochloric acid. The resulting precipitates were collected by filtration and washed with water to give 3-methoxy-4-methylcarbamoylcinnamic acid (250 mg).

NMR (DMSO-d$_6$, δ): 2.78 (3H, d, J=5 Hz), 3.91 (3H, s), 6.66 (1H, d, J=16 Hz), 7.31 (1H, d, J=8 Hz), 7.43 (1H, s), 7.59 (1H, d, J=16 Hz), 7.73 (1H, d, J=8 Hz), 8.16 (1H, q-like)

Preparation 48

9-Hydroxy-3,4-dihydro-2H-[1,3]oxazino[3,2-a]benzimidazole was obtained from 9-benzyloxy-3,4-dihydro-2H-[1,3]oxazino[3,2-a]benzimidazole according to a similar manner to that of Preparation 35.

mp: 227–230° C.

NMR (CDCl$_3$, δ): 2.28–2.39 (2H, m), 4.10 (2H, br t, J=7.5 Hz), 4.54 (2H, br t, J=6 Hz), 6.71 (1H, d, J=7.5 Hz), 6.80 (1H, d, J=7.5 Hz), 7.06 (1H, t, J=7.5 Hz)

Example 16

(1) 2-Amino-3-[2,6-dichloro-3-[N-(phthalimidoacetyl)-N-methylamino]benzyloxy]-N-methylaniline was obtained from 2-amino-3-hydroxy-N-methylaniline and 2,6-dichloro-1-methylsulfonyloxymethyl-3-[N-methyl-N-(phthalimidoacetyl)-amino]benzene according to a similar manner to that of Example 1.

NMR (CDCl$_3$, δ) 2.83 (3H, s), 3.25 (3H, s), 4.09 (2H, s), 5.33 (1H, d, J=10 Hz), 5.41 (1H, d, J=10 Hz), 6.41 (1H, d, J=8 Hz), 6.65 (1H, d, J=8 Hz), 6.85 (1H, t, J=8 Hz), 7.44–7.56 (2H, m), 7.68–7.78 (2H, m), 7.80–7.90 (2H, m)

(2) 4-[2,6-Dichloro-3-[N-(phthalimidoacetyl)-N-methylamino]-benzyloxy]-2-methoxy-1-methyl-1H-benzimidazole was obtained according to a similar manner to that of Preparation 15-(2).

NMR (CDCl$_3$, δ) 3.24 (3H, s), 3.53 (3H, s), 4.10 (2H, s), 4.20 (3H, s), 5.63–5.74 (2H, m), 6.80–6.88 (2H, m), 7.10 (1H, t, J=8 Hz), 7.43–7.55 (2H, m), 7.67–7.76 (2H, m), 7.80–7.90 (2H, m)

(3) 4-[3-(N-Glycyl-N-methylamino)-2,6-dichlorobenzyloxy]-2-methoxy-1-methyl-1H-benzimidazole was obtained according to a similar manner to that of Example 3.

NMR (CDCl$_3$, δ): 3.00 (1H, d, J=15 Hz), 3.10 (1H, d, J=15 Hz), 3.21 (3H, s), 3.51 (3H, s), 4.16 (3H, s), 5.62 (2H, s), 6.78–6.88 (2H, m), 7.09 (1H, t, J=8 Hz), 7.23 (1H, d, J=8 Hz), 7.43 (1H, d, J=8 Hz)

Example 17

The following compounds were obtained according to a similar manner to that of Example 7.

(1) 4-[3-[N-(4-Acetamido-3-methylcinnamoylglycyl)-N-methylamino]-2,6-dichlorobenzyloxy]-2-methoxy-1-methyl-1H-benzimidazole NMR (CDCl$_3$, δ) 2.22 (3H, s), 2.27 (3H, s), 3.25 (3H, s), 3.55 (3H, s), 3.65 (1H, dd, J=4, 18 Hz), 3.94 (1H, dd, J=4, 18 Hz), 4.19 (3H, s), 5.65 (2H, s), 6.41 (1H, d, J=16 Hz), 6.60 (1H, br peak), 6.80–6.89 (2H, m), 7.00 (1H, br s), 7.12 (1H, t, J=8 Hz), 7.23–7.41 (3H, m), 7.41–7.55 (2H, m), 7.94 (1H, d, J=8 Hz)

(2) 4-[3-[N-[3-Methoxy-4-(methylcarbamoyl) cinnamoylglycyl]-N-methylamino]-2,6-dichlorobenzyloxy]-2-methoxy-1-methyl-1H-benzimidazole NMR (CDCl$_3$, δ): 3.02 (3H, d, J=5 Hz), 3.27 (3H, s), 3.55 (3H, s), 3.67 (1H, dd, J=4, 18 Hz), 3.93 (1H, dd, J=4, 18 Hz), 3.97 (3H, s), 4.19 (3H, s), 5.65 (2H, s), 6.53 (1H, d, J=16 Hz), 6.69 (1H, t-like), 6.81–6.89 (2H, m), 7.03 (1H, s-like), 7.11 (1H, t, J=8 Hz), 7.23 (1H, d, J=8 Hz), 7.30 (1H, d, J=8 Hz), 7.47 (1H, d, J=8 Hz), 7.55 (1H, d, J=16 Hz), 7.79 (1H, q-like), 8.21 (1H, d, J=8 Hz)

(3) 4-[2,6-Dichloro-3-[N-methyl-N-[4-(2-oxopyrrolidin-1-yl)-cinnamoylglycyl]amino]benzyloxy]-2-methoxy-1-methyl-1H-benzimidazole NMR (CDCl$_3$, δ) 2.11–2.22 (2H, m), 2.62 (2H, t, J=7.5 Hz), 3.27 (3H, s), 3.53 (3H, s), 3.66 (1H, dd, J=17, 4 Hz), 3.88 (2H, t, J=7.5 Hz), 3.94 (1H, d, J=14, 5 Hz), 4.19 (3H, s), 5.65 (2H, s), 6.42 (1H, d, J=15 Hz), 6.60 (1H, br t, J=5 Hz), 6.81–6.88 (2H, m), 7.10 (1H, t, J=7.5 Hz), 7.30 (1H, d, J=7.5 Hz), 7.45–7.58 (4H, m), 7.66 (2H, d, J=7.5 Hz)

(4) 4-[2,6-Dichloro-3-[N-[4-[N-methoxyacetyl-N-(3-pyridylmethyl)amino]cinnamoylglycyl]-N-methylamino]-benzyloxy]-2-methoxy-1-methyl-1H-benzimidazole NMR (CDCl$_3$, δ): 3.28 (3H, s), 3.34 (3H, s), 3.53 (3H, s), 3.68 (1H, dd, J=17, 4 Hz), 3.80 (2H, s), 3.95 (1H, d, J=14, 5 Hz), 4.19 (3H, s), 4.89 (2H, s), 5.65 (2H, s), 6.46 (1H, d, J=15 Hz), 6.68 (1H, br s), 6.81–6.89 (2H, m), 6.99 (2H, d, J=7.5 Hz), 7.11 (1H, t, J=7.5 Hz), 7.20–7.33 (2H, m), 7.45–7.59 (4H, m), 7.67 (1H, br d, J=7.5 Hz), 8.37 (1H, br s), 8.51 (1H, d, J=5 Hz)

(5) 4-[2,6-Dichloro-3-[N-methyl-N-[4-[(E)-2-(4-pyridyl)-vinyl]cinnamoylglycyl]amino]benzyloxy]-2-methoxy-1-methyl-1H-benzimidazole NMR (CDCl$_3$, δ): 3.28 (3H, s), 3.52 (3H, s), 3.68 (1H, dd, J=17, 4 Hz), 3.95 (1H, d, J=14, 5 Hz), 4.19 (3H, s), 5.66 (2H, s), 6.50 (1H, d, J=15 Hz), 6.64 (1H, br s), 6.80–6.88 (2H, m), 7.05 (1H, d, J=15 Hz), 7.11 (1H, t, J=7.5 Hz), 7.30 (1H, d, J=7.5 Hz), 7.37 (2H, d, J=7.5 Hz), 7.45–7.61 (7H, m), 8.59 (1H, d, J=7.5 Hz)

(6) 4-[2,6-Dichloro-3-[N-methyl-N-[4-[2-(4-pyridyl) ethyl]-cinnamoylglycyl]amino]benzyloxy]-2-methoxy-1-methyl-1H-benzimidazole NMR (CDCl$_3$, δ): 2.91 (4H, br s), 3.27 (3H, s), 3.52 (3H, s), 3.65 (1H, dd, J=17, 4 Hz), 3.94 (1H, d, J=14, 5 Hz), 4.19 (3H, s), 5.64 (2H, s), 6.43 (1H, d, J=15 Hz), 6.61 (1H, br s), 6.81–6.88 (2H, m), 7.02–7.18 (5H, m), 7.30 (1H, d, J=7.5 Hz), 7.42 (2H, br d, J=7.5 Hz), 7.48 (1H, d, J=7.5 Hz), 7.54 (1H, d, J=15 Hz), 8.48 (1H, d, J=7.5 Hz)

(7) 4-[2,6-Dichloro-3-[N-methyl-N-[(E)-3-[6-[(E)-2-(4-pyridyl)vinyl]pyridin-3-yl]acryloylglycyl]amino] benzyloxy]-2-methoxy-1-methyl-1H-benzimidazole NMR (CDCl$_3$, δ): 3.28 (3H, s), 3.52 (3H, s), 3.68 (1H, dd, J=17, 4 Hz), 3.96 (1H, d, J=14, 5 Hz), 4.19 (3H, s), 5.67 (2H, s), 6.58 (1H, d, J=15 Hz), 6.69 (1H, br s), 6.81–6.88 (2H, m), 7.11 (1H, t, J=7.5 Hz), 7.30 (1H, d, J=15 Hz), 7.34 (1H, d, J=15 Hz), 7.39–7.51 (4H, m), 7.58 (1H, d, J=8 Hz), 7.62 (1H, d, J=8 Hz), 7.82 (1H, br d, J=7.5 Hz), 8.61 (2H, br d, J=7.5 Hz), 8.74 (1H, br s)

(8) 4-[3-[N-[(E)-3-(1-Acetyl-1,2,3,4-tetrahydroquinolin-6-yl) acryloylglycyl]-N-methylamino]-2,6-dichlorobenzyloxy]-2-methoxy-1-methyl-1H-benzimidazole NMR (CDCl$_3$, δ): 1.96 (2H, m), 2.23 (3H, s), 2.73 (2H, t, J=7 Hz), 3.25 (3H, s), 3.52 (3H, s), 3.64 (1H, dd, J=4, 16 Hz), 3.78 (2H, t, J=7 Hz), 3.93 (1H, dd, J=4, 16 Hz), 4.19 (3H, s), 5.15 (2H, s), 6.42 (1H, d, J=16 Hz), 6.69 (1H, br peak), 6.80–6.88 (2H, m), 7.10 (1H, t, J=8 Hz), 7.20–7.38 (4H, m), 7.43–7.58 (2H, m)

(9) 4-[3-[N-[(E)-3-(6-Acetamido-5-methylpyridin-3-yl)-acryloylglycyl]-N-methylamino]-2,6-dichlorobenzyloxy]-2-methoxy-1-methyl-1H-benzimidazole NMR (CDCl$_3$, δ) 2.23 (3H, s), 2.31 (3H, s), 3.27 (3H, s), 3.51 (3H, s), 3.66 (1H, dd, J=4, 18 Hz), 3.95 (1H, dd, J=4, 18 Hz), 4.17 (3H, s), 5.64 (2H, s), 6.48 (1H, d, J=16 Hz), 6.79 (1H, br peak), 6.81–6.89 (2H, m), 7.10 (1H, t, J=8 Hz), 7.30 (1H, d, J=8 Hz), 7.43–7.56 (2H, m), 7.65 (1H, s-like), 7.83 (1H, br s), 8.31 (1H, s-like)

(10) 4-[2,6-Dichloro-3-[N-[(E)-3-(6-ethoxycarbonylpyridin-3-yl)acryloylglycyl]-N-methylamino]benzyloxy]-2-methoxy-1-methyl-1H-benzimidazole NMR (CDCl$_3$, δ): 1.46 (3H, t, J=7.5 Hz), 3.27 (3H, s), 3.52 (3H, s), 3.70 (1H, dd, J=4, 18 Hz), 3.90 (1H, dd, J=4, 18 Hz), 4.17 (3H, s), 4.49 (2H, q, J=7.5 Hz), 5.65 (2H, s), 6.65 (1H, d, J=16 Hz), 6.75 (1H, t-like), 6.81–6.89 (2H, m), 7.11 (1H, t, J=8 Hz), 7.31 (1H, d, J=8 Hz), 7.48 (1H, d, J=8 Hz), 7.61 (1H, d, J=16 Hz), 7.93 (1H, d, J=8 Hz), 8.13 (1H, d, J=8 Hz), 8.35 (1H, s-like)

(11) 4-[3-[N-[(E)-3-(6-Aminopyridin-3-yl) acryloylglycyl]-N-methylamino]-2,6-dichlorobenzyloxy]-2-methoxy-1-methyl-1H-benzimidazole NMR (CDCl$_3$, δ): 3.27 (3H, s), 3.54 (3H, s), 3.65 (1H, dd, J=17, 4 Hz), 3.94 (1H, d, J=14, 5 Hz), 4.19 (3H, s), 4.69 (2H, s), 5.64 (2H, s), 6.30 (1H, d, J=15 Hz), 6.50 (1H, d, J=7.5 Hz), 6.56 (1H, br s), 6.81–6.88 (2H, m), 7.10 (1H, t, J=7.5 Hz), 7.30 (1H, d, J=7.5 Hz), 7.42–7.50 (2H, m), 7.61 (1H, br d, J=7.5 Hz), 8.18 (1H, br s)

(12) 4-[3-[N-(4-Acetamido-3-methoxycinnamoylglycyl)-N-methylamino]-2,6-dichlorobenzyloxy]-2-methoxy-1-methyl-1H-benzimidazole NMR (CDCl$_3$, δ): 2.20 (3H, s), 3.28 (3H, s), 3.53 (3H, s), 3.66 (1H, dd, J=17, 4 Hz), 3.89–4.00 (4H, m), 4.19 (3H, s), 5.65 (2H, s), 6.40 (1H, d, J=15 Hz), 6.60 (1H, br s), 6.81–6.89 (2H, m), 7.00 (1H, br s), 7.08–7.16 (2H, m), 7.30 (1H, d, J=7.5 Hz), 7.48 (1H, d, J=7.5 Hz), 7.50 (1H, d, J=15 Hz), 7.81 (1H, br s), 7.38 (1H, br d, J=7.5 Hz)

(13) 4-[2,6-Dichloro-3-[N-[4-(dimethylcarbamoyl)cinnamoylglycyl]-N-methylamino]benzyloxy]-2-methoxy-1-methyl-1H-benzimidazole NMR (CDCl₃, δ): 2.98 (3H, br s), 3.11 (3H, br s), 3.27 (3H, s), 3.53 (3H, s), 3.65 (1H, dd, J=4, 18 Hz), 3.93 (1H, dd, J=4, 18 Hz), 4.18 (3H, s), 5.63 (2H, s), 6.50 (1H, d, J=16 Hz), 6.55 (1H, t-like), 6.80–6.87 (2H, m), 7.10 (1H, t, J=8 Hz), 7.30 (1H, d, J=8 Hz), 7.38–7.61 (6H, m)

Example 18

The following compounds were obtained according to a similar manner to that of Preparation 15-(2).

(1) 4-[3-[N-[(E)-3-(6-Acetamidopyridin-3-yl)acryloylglycyl]-N-methylamino]-2,6-dichlorobenzyloxy]-2-methoxy-1H-benzimidazole NMR (CDCl₃, δ): 2.21 (3H, s), 3.29 (3H, s), 3.59 (1H, br d, J=17 Hz), 4.10–4.22 (4H, m), 5.30 (1H, d, J=10 Hz), 5.59 (1H, d, J=10 Hz), 6.48 (1H, d, J=15 Hz), 6.78 (1H, br s), 7.83 (1H, d, J=7.5 Hz), 7.12 (1H, t, J=15 Hz), 7.20–7.29 (1H, m), 7.32 (1H, d, J=7.5 Hz), 7.49 (1H, d, J=7.5 Hz), 7.65 (1H, d, J=15 Hz), 7.85 (1H, br d, J=7.5 Hz), 8.09 (1H, br s), 8.23 (1H, br d, J=7.5 Hz), 8.37 (1H, br s)

(2) 4-[3-[N-[(E)-3-(6-Acetamidopyridin-3-yl)acryloylglycyl]-N-methylamino]-2,6-dichlorobenzyloxy]-1-ethyl-2-methoxy-1H-benzimidazole NMR (CDCl₃, δ): 1.35 (3H, t, J=7.5 Hz), 2.22 (3H, s), 3.67 (1H, dd, J=4, 18 Hz), 3.94 (1H, dd, J=4, 18 Hz), 4.00 (2H, q, J=7.5 Hz), 4.18 (3H, s), 5.64 (2H, s), 6.46 (1H, d, J=16 Hz), 6.69 (1H, t-like), 6.80–6.90 (2H, m), 7.11 (1H, t, J=8 Hz), 7.30 (1H, d, J=8 Hz), 7.44–7.58 (2H, m), 7.84 (1H, dd, J=2, 8 Hz), 8.08 (1H, s), 8.20 (1H, d, J=8 Hz), 8.35 (2H, d)

(3) 4-(3-[N-[(E)-3-(6-Acetamidopyridin-3-yl)acryloylglycyl]-N-methylamino]-2,6-dichlorobenzyloxy]-2-methoxy-1-methyl-1H-benzimidazole NMR (CDCl₃, δ) 2.21 (3H, s), 3.28 (3H, s), 3.53 (3H, s), 3.66 (1H, dd, J=17, 4 Hz), 3.95 (1H, dd, J=17, 6 Hz), 4.19 (3H, s), 5.66 (2H, s), 6.46 (1H, d, J=15 Hz), 6.68 (1H, t-like), 6.80–6.88 (2H), 7.10 (1H, t, J=8 Hz), 7.29 (1H, d, J=8 Hz), 7.44–7.56 (2H), 7.83 (1H, dd, J=8, 2 Hz), 8.07 (1H, br s), 8.20 (1H, d, J=8 Hz), 8.35 (1H, br s)

(4) 4-[2,6-Dimethyl-3-[N-methyl-N-[4-(methylcarbamoyl)cinnamoylglycyl]amino]benzyloxy]-2-methoxy-1-methyl-1H-benzimidazole NMR (CDCl₃, δ): 2.35 (3H, s), 2.51 (3H, s), 3.03 (3H, d, J=5 Hz), 3.25 (3H, s), 3.55 (3H, s), 3.64 (1H, dd, J=4, 16 Hz), 3.88 (1H, dd, J=4, 16 Hz), 4.19 (3H, s), 5.41 (2H, s), 6.15 (1H, br s), 6.53 (1H, d, J=16 Hz), 6.72 (1H, br peak), 6.81–6.89 (2H, m), 7.02–7.18 (3H, m), 7.50–7.62 (3H, m), 7.75 (2H, d, J=8 Hz)

Example 19

To a solution of 3-hydroxy-2-amino-N-(2-methoxyethyl)aniline (271 mg) in N,N-dimethylformamide (3 ml) was added sodium hydride (35.7 mg) at 0° C. under nitrogen atmosphere, and after stirring for 30 minutes at the same temperature, a solution of 3-[N-[(E)-3-(6-acetamidopyridin-3-yl)acryloylglycyl]-N-methylamino]-2,6-dichlorobenzyl chloride (699 mg) in N,N-dimethylformamide (5 ml) was dropwise added thereto. The mixture was stirred for 1 hour, and water was added to the reaction mixture. The mixture was extracted with chloroform, and the extract was washed with brine, dried over magnesium sulfate and evaporated in vacuo to give a residue containing 3-[3-[N-[(E)-3-(6-acetamidopyridin-3-yl)acryloylglycyl]-N-methylamino]-2,6-dichlorobenzyloxy]-2-amino-N-(2-methoxyethyl)aniline.

To a solution of the obtained residue in acetic acid (2 ml) was added tetramethyl orthocarbonate (304 mg) at ambient temperature, and the mixture was allowed to stand for 20 hours. The reaction mixture was concentrated, and the residue was purified by silica gel column chromatography (chloroform:methanol=50:1, v/v) to give 4-[3-[N-[(E)-3-(6-acetamidopyridin-3-yl)acryloylglycyl]-N-methylamino]-2,6-dichlorobenzyloxy]-2-methoxy-1-(2-methoxyethyl)-1H-benzimidazole (96 mg).

NMR (CDCl₃, δ): 2.23 (3H, s), 3.27 (3H, s), 3.32 (3H, s), 3.62–3.73 (2H, m), 3.95 (1H, dd, J=4, 18 Hz), 4.13 (2H, t, J=7 Hz), 4.20 (3H, s), 5.65 (2H, s), 6.46 (1H, d, J=16 Hz), 6.67 (1H, t-like), 6.83 (1H, d, J=8 Hz), 6.92 (1H, d, J=8 Hz), 7.10 (1H, t, J=8 Hz), 7.30 (1H, d, J=8 Hz), 7.45–7.58 (2H, m), 7.85 (1H, dd, J=8, 2 Hz), 8.06 (1H, s), 8.21 (1H, d, J=8 Hz), 8.35 (1H, d, J=2 Hz)

Example 20

A mixture of 3-[2,6-dimethyl-3-[N-[4-(methylcarbamoyl)cinnamoylglycyl]-N-methylamino]benzyloxy]-2-amino-N-methylaniline (65.3 mg), 1,1'-thiocarbonyldiimidazole (33.0 mg) and anhydrous tetrahydrofuran (0.7 ml) was stirred for 7 hours at ambient temperature. The reaction mixture was diluted with chloroform and washed with water and brine. The organic layer was dried over magnesium sulfate and evaporated in vacuo. The residue was washed with diethyl ether to give 4-[2,6-dimethyl-3-[N-[4-(methylcarbamoyl)cinnamoylglycyl]-N-methylamino]benzyloxy]-2-mercapto-1-methyl-1H-benzimidazole (51.8 mg) as pale brown solid.

mp: 278.5–292° C.

NMR (DMSO-d₆, δ): 2.26 (3H, s), 2.42 (3H, s), 2.79 (3H, d, J=4.5 Hz), 3.11 (3H, s), 3.49 (1H, dd, J=16.5, 4.5 Hz), 3.63 (3H, s), 3.71 (1H, dd, J=16.5, 4.5 Hz), 5.23 (1H, d, J=11.0 Hz), 5.30 (1H, d, J=11.0 Hz), 6.90 (1H, d, J=16.0 Hz), 7.03 (1H, d, J=8.5 Hz), 7.09 (1H, d, J=8.5 Hz) 7.20 (1H, t, J=8.5 Hz), 7.25 (1H, d, J=8.5 Hz), 7.31 (1H, d, J=8.5 Hz), 7.44 (1H, d, J=16.0 Hz), 7.64 (2H, d, J=8.5 Hz), 7.85 (2H, d, J=8.5 Hz), 8.27 (1H, t, J=4.5 Hz), 8.48 (1H, q, J=4.5 Hz)

Example 21

To a mixture of 4-[2,6-dimethyl-3-[N-(4-(methylcarbamoyl)cinnamoylglycyl]-N-methylamino]benzyloxy]-2-mercapto-1-methyl-1H-benzimidazole (34.9 mg), potassium carbonate (10.1 mg) and N,N-dimethylformamide (0.4 ml) was added methyl iodide (4 μl) at ambient temperature, and the mixture was stirred for 16 hours. The reaction mixture was poured into water, and extracted with chloroform. The extract was washed with water and brine, dried over magnesium sulfate and evaporated in vacuo. The residue was purified by preparative thin layer chromatography (ethyl acetate:methanol=10:1, v/v) to give 4-[2,6-dimethyl-3-[N-[4-(methylcarbamoyl)cinnamoylglycyl]-N-methylamino]benzyloxy]-1-methyl-2-methylthio-1H-benzimidazole (21.2 mg).

mp: 224.0–225.0° C.

NMR (DMSO-d₆, δ): 2.30 (3H, s), 2.43 (3H, s), 2.67 (3H, s), 2.77 (3H, d, J=5.5 Hz), 3.09 (3H, s), 3.48 (1H, dd, J=16.5, 5.5 Hz), 3.63 (3H, s), 3.64 (1H, dd, J=16.5, 5.5 Hz), 5.35 (2H, s), 6.87 (1H, d, J=16.0 Hz), 6.90 (1H, m), 7.07–7.15 (2H, m), 7.23 (1H, d, J=8.5 Hz), 7.30

(1H, d, J=8.5 Hz), 7.40 (1H, d, J=16.0 Hz), 7.61 (2H, d, J=8.5 Hz), 7.83 (2H, d, J=8.5 Hz), 8.23 (1H, t, J=5.5 Hz), 8.47 (1H, q, J=5.5 Hz)

Example 22

To a solution of 4-[3-[N-[(E)-3-(6-acetamidopyridin-3-yl) acryloylglycyl]-N-methylamino]-2,6-dichlorobenzyloxy]-2-methoxy-1H-benzimidazole (100 mg) and 2-dimethylaminoethyl chloride hydrochloride (25.6 mg) in N,N-dimethylformamide (2 ml) was added potassium carbonate (92.5 mg) at ambient temperature, and the mixture was stirred for 28 hours at the same temperature. The reaction mixture was poured into water, and extracted with chloroform. The extract was washed with water and brine, dried over magnesium sulfate and evaporated in vacuo. The residue was purified by preparative thin layer chromatography to give 4-[3-[N-[(E)-3-(6-acetamidopyridin-3-yl) acryloylglycyl]-N-methylamino]-2,6-dichlorobenzyloxy]-2-methoxy-1-(2-dimethylaminoethyl)-1H-benzimidazole (11 mg) and 7-[3-[N-[(E)-3-(6-acetamidopyridin-3-yl) acryloylglycyl]-N-methylamino]-2,6-dichlorobenzyloxy]-2-methoxy-1-(2-dimethylaminoethyl)-1H-benzimidazole (38 mg).

4-[3-[N-[(E)-3-(6-Acetamidopyridin-3-yl) acryloylglycyl]-N-methylamino]-2,6-dichlorobenzyloxy]-2-methoxy-1-(2-dimethylaminoethyl)-1H-benzimidazole NMR (CDCl$_3$, δ): 2.22 (3H, s), 2.31 (6H, s), 2.63 (2H, t, J=7.5 Hz), 3.26 (3H, s), 3.67 (1H, dd, J=4, 18 Hz), 3.96 (1H, dd, J=4, 18 Hz), 4.06 (2H, t, J=7.5 Hz), 4.19 (3H, s), 5.65 (2H, s), 6.45 (1H, d, J=16 Hz), 6.70–6.79 (1H, m), 6.79–6.92 (2H, m), 7.10 (1H, t, J=8 Hz), 7.31 (1H, d, J=8 Hz), 7.43–7.58 (2H, m), 7.83 (1H, dd, J=2, 8 Hz), 8.22 (1H, d, J=8 Hz), 8.26–8.39 (2H, m)

7-[3-[N-[(E)-3-(6-Acetamidopyridin-3-yl) acryloylglycyl]-N-methylamino]-2,6-dichlorobenzyloxy]-2-methoxy-1-(2-dimethylaminoethyl)-1H-benzimidazole NMR (CDCl$_3$, δ): 2.01 (6H, s), 2.22 (3H, s), 2.51 (2H, t, J=8 Hz), 3.28 (3H, s), 3.65 (1H, dd, J=4, 18 Hz), 3.95 (1H, dd, J=4, 18 Hz), 4.06–4.18 (5H, m), 5.45 (2H, s), 6.45 (1H, d, J=16 Hz), 6.62 (1H, t-like), 6.83 (1H, d, J=8 Hz), 7.11 (1H, t, J=8 Hz), 7.20–7.30 (1H, m), 7.36 (1H, d, J=8 Hz), 7.47–7.56 (2H, m), 7.85 (1H, d, J=8 Hz), 8.00 (1H, s), 8.21 (1H, d, J=8 Hz), 8.35 (1H, d, J=2 Hz)

Example 23

(1) 4-[3-[N-[(E)-3-(6-Acetamidopyridin-3-yl) acryloylglycyl]-N-methylamino]-2,6-dichlorobenzyloxy]-1-[2-(tert-butyldiphenylsilyloxy)ethyl]-2-methoxy-1H-benzimidazole and 7-[3-[N-[(E)-3-(6-acetamidopyridin-3-yl)acryloylglycyl]-N-methylamino]-2,6-dichlorobenzyloxy]-1-[2-(tert-butyldiphenylsilyloxy)ethyl]-2-methoxy-1H-benzimidazole were obtained from 4-[3-[N-[(E)-3-(6-acetamidopyridin-3-yl)acryloylglycyl]-N-methylamino]-2,6-dichlorobenzyloxy]-2-methoxy-1H-benzimidazole and 1-(tert-butyldiphenylsilyloxy)-2-methoxyethane according to a similar manner to that of Example 22.

4-[3-[N-[(E)-3-(6-Acetamidopyridin-3-yl) acryloylglycyl]-N-methylamino]-2,6-dichlorobenzyloxy]-1-[2-(tert-butyldiphenylsilyloxy)ethyl]-2-methoxy-1H-benzimidazole NMR (CDCl$_3$, δ): 0.95 (9H, s), 2.21 (3H, s), 3.27 (3H, s), 3.67 (1H, dd, J=17, 4 Hz), 3.84–4.00 (3H, m), 4.06–4.12 (5H, m), 5.66 (2H, s), 6.45 (1H, d, J=15 Hz), 6.67 (1H, br s), 6.73 (1H, d, J=7.5 Hz), 6.80 (1H, d, J=7.5 Hz), 7.02 (1H, t, J=7.5 Hz), 7.28–7.57 (13H, m), 7.83 (1H, br dd, J=7.5, 2 Hz), 8.02 (1H, br s), 8.20 (1H, br d, J=7.5 Hz), 8.35 (1H, br s)

7-[3-[N-[(E)-3-(6-Acetamidopyridin-3-yl) acryloylglycyl]-N-methylamino]-2,6-dichlorobenzyloxy]-1-[2-(tert-butyldiphenylsilyloxy)ethyl]-2-methoxy-1H-benzimidazole NMR (CDCl$_3$, δ): 0.89 (9H, s), 2.22 (3H, s), 3.09 (3H, s), 3.48 (1H, br dd, J=17, 4 Hz), 3.79 (2H, br t, J=5 Hz), 3.87 (1H, br dd, J=17, 5 Hz), 4.12 (3H, s), 4.20 (2H, br t, J=5 Hz), 5.29 (2H, s), 6.41 (1H, d, J=15 Hz), 6.49 (1H, br s), 6.80 (1H, d, J=7.5 Hz), 7.10–7.44 (14H, m), 7.50 (1H, d, J=15 Hz), 7.85 (1H, dd, J=7.5, 2 Hz), 8.03 (1H, br s), 8.23 (1H, br d, J=7.5 Hz), 8.36 (1H, br s)

Example 24

(1) 4-[3-[N-[(E)-3-(6-Acetamidopyridin-3-yl) acryloylglycyl]-N-methylamino]-2,6-dichlorobenzyloxy]-1-(2-hydroxyethyl)-2-methoxy-1H-benzimidazole was obtained from 4-[3-[N-[(E)-3-(6-acetamidopyridin-3-yl) acryloylglycyl]-N-methylamino]-2,6-dichlorobenzyloxy]-1-[2-(tert-butyldiphenylsilyloxy)ethyl]-2-methoxy-1H-benzimidazole according to a similar manner to that of Preparation 13-(5).

NMR (CDCl$_3$, δ): 2.21 (3H, s), 3.27 (3H, s), 3.69 (1H, dd, J=17, 4 Hz), 3.87–4.00 (3H, m), 4.09–4.19 (5H, m), 5.64 (2H, s), 6.47 (1H, d, J=15 Hz), 6.75 (1H, br s), 6.85 (1H, d, J=7.5 Hz), 6.94 (1H, d, J=7.5 Hz), 7.10 (1H, t, J=7.5 Hz), 7.30 (1H, d, J=7.5 Hz), 7.48 (1H, d, J=7.5 Hz), 7.51 (1H, d, J=15 Hz), 7.82 (1H, br d, J=7.5 Hz), 8.09 (1H, br s), 8.19 (1H, br d, J=7.5 Hz), 8.30 (1H, br s)

(2) 7-[3-[N-[(E)-3-(6-Acetamidopyridin-3-yl) acryloylglycyl]-N-methylamino]-2,6-dichlorobenzyloxy]-1-(2-hydroxyethyl)-2-methoxy-1H-benzimidazole was obtained from 7-[3-[N-[(E)-3-(6-acetamidopyridin-3-yl) acryloylglycyl]-N-methylamino]-2,6-dichlorobenzyloxy]-1-[2-(tert-butyldiphenylsilyloxy)ethyl]-2-methoxy-1H-benzimidazole according to a similar manner to that of Preparation 13-(5).

NMR (CDCl$_3$, δ): 2.21 (3H, s), 3.29 (3H, s), 3.64–3.74 (3H, m), 3.80 (1H, d, J=5 Hz), 4.12–4.21 (5H, m), 5.43 (1H, d, J=10 Hz), 5.49 (1H, d, J=10 Hz), 6.45 (1H, d, J=15 Hz), 6.78 (1H, br t, J=5 Hz), 6.81 (1H, d, J=7.5 Hz), 7.11 (1H, t, J=7.5 Hz), 7.24 (1H, d, J=7.5 Hz), 7.36 (1H, d, J=7.5 Hz), 7.53 (1H, d, J=15 Hz), 7.58 (1H, d, J=7.5 Hz), 7.84 (1H, br d, J=7.5 Hz), 8.02 (1H, br s), 8.22 (1H, br d, J=7.5 Hz), 8.35 (1H, br s)

Example 25

To a solution of 4-[3-[N-[(E)-3-(6-ethoxycarbonylpyridin-3-yl)acryloylglycyl]-N-methylamino]-2,6-dichlorobenzyloxy]-2-methoxy-1-methyl-1H-benzimidazole (304 mg) in ethanol was added 1N sodium hydroxide solution (0.5 ml), and the mixture was stirred for 1.5 hours at ambient temperature. The solvent was removed, water was added to the residue. The mixture was adjusted to pH 4 with 1N hydrochloric acid and extracted with chloroform. The extract was dried and evaporated in vacuo. Acetonitrile was added to the residue, and the residue was collected by filtration to give 4-[3-[N-[(E)-3-(6-carboxypyridin-3-yl)acryloylglycyl]-N-methylamino]-2,6-dichlorobenzyloxy]-2-methoxy-1-methyl-1H-benzimidazole (195 mg).

NMR (CDCl$_3$—CD$_3$OD, δ): 3.25 (3H, s), 3.53–3.68 (4H, m), 4.00 (1H, d, J=16 Hz), 4.14 (3H, s), 5.52–5.63 (2H, m), 6.76–6.96 (3H, m), 7.15 (1H, t, J=8 Hz), 7.48–7.61 (4H, m), 8.02–8.20 (2H, m)

Example 26

To a solution of 4-[3-[N-[(E)-3-(6-carboxypyridin-3-yl) acryloylglycyl]-N-methylamino]-2,6-dichlorobenzyloxy]-2-methoxy-1-methyl-1H-benzimidazole (90 mg) and 4-aminopyridine (14.3 mg) in N,N-dimethylformamide (2 ml) were added 1-ethyl-3-(3-dimethylaminopropyl) carbodiimide hydrochloride (31.7 mg) and 1-hydroxybenzotriazole (26.4 mg) at ambient temperature, and after standing for 1 day, the mixture was stirred for 8 hours at 50° C. To the mixture was added water, and extracted with ethyl acetate. The extract was washed with saturated sodium bicarbonate solution and brine, dried over magnesium sulfate and evaporated in vacuo. The residue was purified by preparative thin layer chromatography (chloroform:methanol, 12:1, v/v) to give 4-[2,6-dichloro-3-[N-methyl-N-[(E)-3-[6-(4-pyridylcarbamoyl)pyridin-3-yl] acryloylglycyl]amino]benzyloxy]-2-methoxy-1-methyl-1H-benzimidazole (7.8 mg).

NMR (CDCl$_3$, δ): 3.27 (3H, s), 3.56 (3H, s), 3.61 (1H, dd, J=4, 18 Hz), 3.96 (1H, dd, J=4, 18 Hz), 4.19 (3H, s), 5.65 (2H, s), 6.67 (1H, d, J=16 Hz), 6.81–6.90 (3H, m), 7.11 (1H, t, J=8 Hz), 7.30 (1H, d, J=8 Hz), 7.48 (1H, d, J=8 Hz), 7.58–7.76 (3H, m), 7.98–8.07 (1H, m), 8.27 (1H, d, J=8 Hz), 8.48–8.73 (3H, m)

Example 27

4-[2,6-Dichloro-3-[N-methyl-N-[(E)-3-[6-(2-pyridylcarbamoyl)pyridin-3-yl]acryloylglycyl]amino]benzyloxy]-2-methoxy-1-methyl-1H-benzimidazole was obtained from 4-[3-[N-[(E)-3-(6-carboxypyridin-3-yl) acryloylglycyl]-N-methylamino]-2,6-dichlorobenzyloxy]-2-methoxy-1-methyl-1H-benzimidazole and 2-aminomethylpyridine according to a similar manner to that of Example 26.

NMR (CDCl$_3$, δ): 3.28 (3H, s), 3.53 (3H, s), 3.69 (1H, dd, J=4, 18 Hz), 3.95 (1H, dd, J=4, 18 Hz), 4.20 (3H, s), 4.80 (2H, d, J=5 Hz), 5.66 (2H, s), 6.62 (1H, d, J=16 Hz), 6.73 (1H, t-like), 6.83–6.88 (2H, m), 7.11 (1H, t, J=8 Hz), 7.21 (1H, dd, J=6, 8 Hz), 7.27–7.36 (2H, m), 7.49 (1H, d, J=8 Hz), 7.62 (1H, d, J=16 Hz), 7.68 (1H, t, J=8 Hz), 7.96 (1H, d, J=8 Hz), 8.22 (1H, d, J=8 Hz), 8.61 (1H, d, J=5 Hz), 8.69 (1H, d, J=2 Hz), 8.90 (1H, t-like)

Example 28

To a solution of 4-[3-[N-[(E)-3-(6-aminopyridin-3-yl) acryloylglycyl]-N-methylamino]-2,6-dichlorobenzyloxy]-2-methoxy-1-methyl-1H-benzimidazole (100 mg) and triethylamine (53.3 mg) in dichloromethane (2 ml) was added 2-methyl-3-pyridinecarbonyl chloride hydrochloride (74.2 mg) under ice-cooling, and the mixture was stirred for 15 minutes at the same temperature and then for 3 hours at ambient temperature. The reaction mixture was concentrated, and the residue was dissolved in methanol (3 ml). To the solution was added 1N sodium hydroxide solution (0.5 ml), and the mixture was stirred for 1 hour. Chloroform was added to the reaction mixture, and the solution was washed with water and brine, dried over magnesium sulfate and evaporated in vacuo. The residue was purified by preparative thin layer chromatography (chloroform:methanol, 10:1, v/v) to give 4-[2,6-dichloro-3-[N-methyl-N-[(E)-3-[6-(2-methylpyridin-3-carboxamido)pyridin-3-yl]acryloylglycyl]amino]benzyloxy]-2-methoxy-1-methyl-1H-benzimidazole (99 mg).

NMR (CDCl$_3$, δ): 2.75 (3H, s), 3.28 (3H, s), 3.52 (3H, s), 3.68 (1H, dd, J=17, 4 Hz), 3.94 (1H, d, J=14, 5 Hz), 4.18 (3H, s), 5.65 (2H, s), 6.50 (1H, d, J=15 Hz), 6.70 (1H, br s), 6.80–6.89 (2H, m), 7.11 (1H, t, J=7.5 Hz), 7.20–7.33 (2H, m), 7.48 (1H, d, J=7.5 Hz), 7.53 (1H, d, J=15 Hz), 7.84 (1H, br d, J=7.5 Hz), 7.92 (1H, br dd, J=7.5, 3 Hz), 8.32–8.46 (3H, m), 8.63 (12H, br d, J=2 Hz)

Example 29

(1) A solution of 2-hydroxy-3-methoxybenzaldehyde (6.08 g), ethyl bromoacetate (4.9 ml) and potassium carbonate (12.14 g) in N,N-dimethylformamide (30 ml) was stirred for 2 hours at ambient temperature. Water was added to the reaction mixture, and the resulting precipitates were collected by filtration and recrystallized with ethanol to give 2-ethoxycarbonylmethoxy-3-methoxybenzaldehyde (5.04 g).

mp: 75.1–76.2° C.

NMR (CDCl$_3$, δ): 1.28 (3H, t, J=7.5 Hz), 3.90 (3H, s), 4.23 (2H, q, J=7.5 Hz), 4.84 (2H, s), 7.15 (2H, d, J=7.5 Hz), 7.46 (1H, t, J=5 Hz), 10.46 (1H, s)

(2) A solution of 2-ethoxycarbonylmethoxy-3-methoxybenzaldehyde (2.00 g) and potassium tert-butoxide (963 mg) in tetrahydrofuran (20 ml) was stirred for 1 hour under ice-cooling. Water was added to the reaction mixture, and the solution was neutralized with 1N hydrochloric acid and extracted with ethyl acetate. The extract was washed with water and brine, dried over magnesium sulfate and evaporated in vacuo. The residue was purified by preparative thin layer chromatography (n-hexane:ethyl acetate=7:1, v/v) to give 2-ethoxycarbonyl-7-methoxybenzofuran (360 mg).

mp: 85° C.

NMR (CDCl$_3$, δ): 1.42 (3H, t, J=7.5 Hz), 4.04 (3H, s), 4.45 (2H, q, J=7.5 Hz), 6.92 (1H, dd, J=7 and 4 Hz), 7.18–7.30 (2H, m), 7.54 (1H, s)

(3) A mixture of 2-ethoxycarbonyl-7-methoxybenzofuran (360 mg), lithium borohydride (36 mg) in tetrahydrofuran (4 ml) was stirred at ambient temperature overnight and then for 8 hours at 50° C. Saturated ammonium chloride solution was added to the reaction mixture, and the solution was extracted with ethyl acetate. The extract was washed with saturated ammonium chloride solution and brine, dried over magnesium sulfate and evaporated in vacuo. The residue was purified by flash chromatography (n-hexane-ethyl acetate) to give 2-hydroxymethyl-7-methoxybenzofuran (310 mg).

NMR (CDCl$_3$, δ): 1.98 (1H, t, J=6 Hz), 4.01 (3H, s), 4.79 (1H, d, J=6 Hz), 6.67 (1H, s), 6.81 (1H, m), 7.12 (1H, dd, J=8, 5 Hz), 7.18 (1H, dd, J=8, 5 Hz)

(4) A mixture of 2-hydroxymethyl-7-methoxybenzofuran (300 mg), sodium cyanoborohydride (796 mg) and zinc iodide (809 mg) in dichloroethane (10 ml) was stirred for 2 hours at ambient temperature and then refluxed overnight. Chloroform and water were added to the reaction mixture, and the separated organic layer was washed with brine, dried over magnesium sulfate and evaporated in vacuo. The residue was purified by flash chromatography (n-hexane:ethyl acetate 15:1, v/v) to give 7-methoxy-2-methylbenzofuran (95 mg).

NMR (CDCl$_3$, δ): 2.48 (3H, s), 4.00 (3H, s), 6.36 (1H, br s), 6.73 (1H, dd, J=17, 4 Hz), 7.07–7.13 (2H, m), 7.26 (1H, s)

(5) 7-Hydroxy-2-methylbenzofuran was obtained according to a similar manner to that of Preparation 1-(4).

NMR (CDCl$_3$, δ): 2.46 (3H, s), 5.22 (1H, s), 6.37 (1H, br s), 6.70–6.81 (1H, m), 6.99–7.11 (2H, m)

(6) 7-[3-(N-Acetyl-N-methylamino)-2,6-dichlorobenzyloxy]-2-methylbenzofuran was obtained from 7-hydroxy-2-methylbenzofuran and 3-(N-acetyl-N-methylamino)-2,6-dichlorobenzyl bromide according to a similar manner to that of Example 9.

mp: 114–116° C.

NMR (CDCl$_3$, δ): 1.83 (3H, s), 2.46 (3H, s), 3.20 (3H, s), 5.54 (2H, s), 6.48 (1H, br s), 6.90 (1H, dd, J=6, 3 Hz), 7.06–7.18 (2H, m), 7.28 (1H, d, J=8 Hz), 7.56 (1H, d, J=8 Hz)

We claim:

1. A heterocyclic compound of the formula:

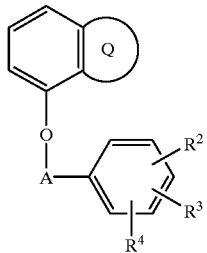

wherein a group of the formula:

is a group of the formula:

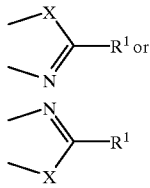

X is N—R$^5$,

R$^1$ is lower alkyl, halo(lower)alkyl, lower alkylamino(lower)alkyl, hydroxy(lower)alkyl, lower alkoxy(lower)alkyl, lower alkoxy, lower alkylthio, lower alkylamino, acyl(lower)alkyl, acyl, hydroxy, mercapto, aryl or ar(lower)alkyl, R$^5$ is hydrogen, lower alkyl, halo(lower)alkyl, lower alkylamino(lower)alkyl, hydroxy(lower)alkyl, lower alkoxy(lower)alkyl, lower alkoxy, lower alkylthio, lower alkylamino, acyl(lower)alkyl, acyl, aryl or ar(lower)alkyl, R$^2$ is hydrogen, halogen, lower alkyl or lower alkoxy, R$^3$ is halogen, lower alkyl or lower alkoxy, R$^4$ is a group of the formula:

in which

R$^6$ is hydrogen or lower alkyl, and

R$^7$ is an amino acid residue substituted with a substituent selected from the group consisting of optionally substituted pyridyl(lower)alkanoyl, pyridyl(lower)alkoxy-ar(lower)alkenoyl, pyridyl-ar(lower)alkenoyl optionally having oxo, pyridyl(lower)alkyl-ar(lower)alkenoyl, pyridyl(lower)alkenyl-ar(lower)alkenoyl, optionally substituted pyridyl(lower)alkanoylamino-ar(lower)alkenoyl, optionally substituted pyridylcarbonylamino-ar(lower)alkenoyl, N-(lower alkanoyl)-N-(pyridyl(lower)alkyl)amino-ar(lower)alkenoyl, N-(lower(pyridylcarbonyl)-N-(lower alkoxy(lower)alkyl)amino-ar(lower)alkenoyl, pyridylureido-ar(lower)alkenoyl, pyridyl(lower)alkylcarbamoyl-ar(lower)-alkenoyl, N-(pyridyl(lower)alkyl)-N-(lower alkyl)carbamoyl-ar(lower alkenoyl, pyridylcarbamoyl-ar(lower)alkenoyl, optionally substituted pyridylcarbonyl-ar(lower)alkenoyl, pyridyl(lower)alkenoyl, pyridyl(lower)alkenyl-pyridyl(lower)alkenoyl, lower alkanoyl-pyridyl(lower)alkenoyl, pyridylthio(lower)alkanoyl, amino-pyridyl(lower)alkenoyl, lower alkylamino-pyridyl(lower)alkenoyl, lower alkanoylamino-pyridyl(lower)alkenoyl in which the pyridyl group may be substituted with lower alkyl or lower alkoxy, lower alkanoylamino(lower)alkanoylamino-pyridyl(lower)alkenoyl, lower alkenoylamino-pyridyl(lower)alkenoyl, pyridyl(lower)alkanoylamino-pyridyl(lower)alkenoyl, pyridylcarbonylamino-pyridyl(lower)alkenoyl which may be substituted with lower alkyl, lower alkoxycarbonyl(lower)alkanoylamino-pyridyl(lower)alkenoyl, lower alkoxy(lower)alkanoylamino-pyridyl(lower)alkenoyl, lower alkylureido-pyridyl(lower)alkenoyl, carboxy-pyridyl(lower)alkenoyl, lower alkoxycarbonyl-pridyl(lower)alkenoyl, lower alkylcarbamoyl-pridyl(lower)alkenoyl, lower alkoxy(lower)alkylcarbamoyl-pyridyl(lower)alkenoyl, hydroxy(lower)alkylcarbamoyl-pyridyl(lower)alkenoyl, pyridylcarbamoyl-pyridyl(lower)alkenoyl, pyridyl(lower)alkylcarbamoyl-pyridyl-(lower)alkenoyl, pyridylcarbonyl-pyridyl(lower)alkenoyl, lower alkenylcarbamoyl-pyridyl(lower)alkenoyl, lower alkenylcarbamoyl-pyridyl(lower)alkenoyl, optionally substituted pyridylcarbonyl, pyridylcarbonyl-arylcarbamoyl, pyridylcarbonylamino-arylcarbamoyl, pridyl(lower)alkanoylamino-arylcarbamoyl, pyridyl-arylcarbamoyl optionally having oxo, pyridylcarbonyl-arylcarbamoyl having lower alkyl, pyridylcarbonyl-arylcarbamoyl having aryl, pyridylcarbonyl-arylcarbamoyl having a pyridyl group, pyridylcarbonyl-arylcarbamoyl having lower alkanoyl, pyridylcarbonyl-arylcarbamoyl having lower alkoxycarbonyl, pyridylcarbonyl-arylcarbamoyl having lower alkylamino, pyridylcarbonyl-arylcarbamoyl having lower alkylcarbamoyl, pyridylcarbamoyl-arylcarbamoyl, N-(pyridyl)-N-(lower alkyl)carbamoyl-arylcarbamoyl, pyridyl(lower)alkylcarbamoyl-arylcarbamoyl, N-(pyridyl(lower)alkyl)-N-(lower alkyl)carbamoyl-arylcarbamoyl, N-(pyridyl(lower)alkyl)-N-(lower alkoxy(lower)alkyl)carbamoyl-arylcarbamoyl, pyridylcarbamoyl, pyridyl(lower)alkylcarbamoyl, amino acid residue substituted with a pyridyl group and amino acid residue substituted with pyridyl(lower)alkyl, and A is lower alkylene, or a salt thereof.

2. A compound of claim 1, wherein
a group of the formula:

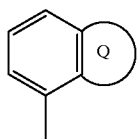

is a group of the formula:

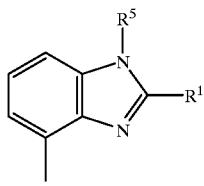

3. A compound of claim 2, wherein
$R^5$ is a lower alkyl,
$R^2$ is hydrogen, halogen or lower alkyl,
$R^3$ is halogen or lower alkyl, and
A is lower alkylene.

4. The heterocyclic compound of claim 1, having the formula:
4-[3-[N-[(E)-3-(6-acetylaminopyridin-3-yl)-acryloylglycyl]-N-methylamino]-2,6-dimethylbenzyloxy]-2-methoxy-1-methyl-1H-benzimidazole.

5. A pharmaceutical composition comprising a compound of claim 1 or its salt, as an active ingredient, in association with a pharmaceutically acceptable excipient.

6. A method for the prevention or the treatment of bradykinin or its analogues mediated diseases selected from allergy, inflammation, shock or pain, which comprises administering a compound of claim 1 or its salt to a human being or animals.

7. An agent for the prevention or the treatment of bradykinin or its analogues mediated diseases selected from allergy, inflammation, shock or pain, which comprises a compound of claim 1 or its salt as an active ingredient.

8. A process for preparing a compound of the formula:

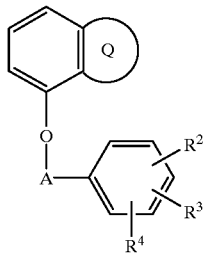

wherein a group of the formula:

$R^2, R^3, R^4$ and A are each as defined below, or its salt, which comprises reacting a compound of the formula:

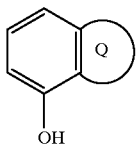

wherein a group of the formula:

is a group of the formula:

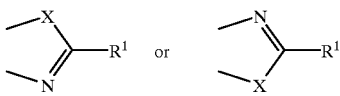

X is N—$R^5$ $R^1$ is lower alkyl, halo(lower)alkyl, lower alkylamino(lower)alkyl, hydroxy(lower)alkyl, lower alkoxy(lower)alkyl, lower alkoxy, lower alkylthio, lower alkylamino, acyl(lower)alkyl, acyl, hydroxy, mercapto, aryl or ar(lower)alkyl, and $R^5$ is hydrogen, lower alkyl, halo(lower)alkyl, lower alkylamino(lower)alkyl, hydroxy(lower)alkyl, lower alkoxy(lower)alkyl, lower alkoxy, lower alkylthio, lower alkylamino, acyl(lower)alkyl, acyl, aryl or ar(lower)alkyl, or its salt with a compound of the formula:

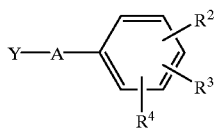

wherein
$R^2$ is hydrogen, halogen, lower alkyl, or lower alkoxy,
$R^3$ is halogen, lower alkyl or lower alkoxy,
$R^4$ is a group of the formula:

in which
$R^6$ is hydrogen or lower alkyl, and
$R^7$ is an amino acid residue substituted with a substituent selected from the group consisting of optionally substituted pyridyl(lower)alkanoyl, pyridyl(lower)alkoxy-ar(lower)alkenoyl, pyridyl-ar(lower)alkenoyl optionally having oxo, pyridyl(lower)alkyl-ar(lower)alkenoyl, pyridyl(lower)alkenyl-ar(lower)alkenoyl, optionally substituted pyridyl(lower)alkanoylamino-ar(lower)alkenoyl, optionally substituted pyridylcarbonylamino-ar(lower)alkenoyl, N-(lower alkanoyl)-N-(pyridyl(lower)alkyl)amino-ar(lower)alkenoyl, N-(lower alkoxy(lower)alkanoyl)-N-(pyridyl(lower)alkyl)amino-ar(lower)alkenoyl, N-(pyridylcarbonyl)-N-(lower alkoxy(lower)alkyl) amino-ar(lower)alkenoyl, pyridylureido-ar(lower) alkenoyl, pyridyl(lower)alkylcarbamoyl-ar(lower)-alkenoyl, N-(pyridyl(lower)alkyl)-N-(lower alkyl) carbamoyl-ar(lower)alkenoyl, pyridylcarbamoyl-ar (lower)alkenoyl, optionally substituted pyridylcarbonyl-ar(lower)alkenoyl, pyridyl(lower) alkenoyl, pyridyl(lower)alkenyl-pyridyl(lower) alkenoyl, lower alkanoyl-pyridyl(lower)alkenoyl, pyridylthio(lower)alkanoyl, amino-pyridyl(lower) alkenoyl, lower alkylamino-pyridyl(lower)alkenoyl, lower alkanoylamino-pyridyl(lower)alkenoyl in which the pyridyl group may be substituted with lower alkyl or lower alkoxy, lower alkanoylamino(lower) alkanoylamino-pyridyl-(lower)alkenoyl, lower alkenoylamino-pyridyl(lower)alkenoyl pyridyl(lower) alkanoylamino-pyridyl-(lower)alkenoyl, pyridylcarbonylamino-pyridyl(lower)alkenoyl which may be substituted with lower alkyl, lower alkoxycarbonyl(lower)alkanoylamino-pyridyl-(lower) alkenoyl, lower alkoxy(lower)alkanoylamino-pyridyl (lower)alkenoyl, lower alkylureido-pyridyl(lower) alkenoyl, carboxy-pyridyl(lower)alkenoyl, lower alkoxycarbonyl-pyridyl(lower)alkenoyl, lower alkylcarbamoyl-pyridyl(lower)alkenoyl, lower alkoxy (lower)alkylcarbamoyl-pyridyl(lower)alkenoyl, hydroxy(lower)alkylcarbamoyl-pyridyl(lower) alkenoyl, pyridylcarbamoyl-pyridyl(lower)alkenoyl, pyridyl(lower)alkylcarbamoyl-pyridyl-(lower) alkenoyl, pyridylcarbonyl-pyridyl(lower)alkenoyl, lower alkenylcarbamoyl-pyridyl(lower)alkenoyl, lower alkenylcarbamoyl-pyridyl(lower)alkenoyl, optionally substituted pyridylcarbonyl, pyridylcarbonyl-arylcarbamoyl, pyridylcarbonylamino-arylcarbamoyl, pyridyl(lower)alkanoylamino-arylcarbamoyl, pyridyl-arylcarbamoyl optionally having oxo, pyridylcarbonyl-arylcarbamoyl having lower alkyl, pyridylcarbonyl-arylcarbamoyl having aryl, pyridylcarbonyl-arylcarbamoyl having a pyridyl group, pyridylcarbonyl-arylcarbamoyl having lower alkanoyl, pyridylcarbonyl-arylcarbamoyl having lower alkoxycarbonyl, pyridylcarbonyl-arylcarbamoyl having lower alkylamino, pyridylcarbonyl-arylcarbamoyl having lower alkylcarbamoyl, pyridylcarbamoyl-arylcarbamoyl, N-(pyridyl)-N-(lower alkyl)carbamoyl-arylcarbamoyl, pyridyl(lower)alkylcarbamoyl-arylcarbamoyl, N-(pyridyl(lower)alkyl)-N-(lower alkyl)carbamoyl-arylcarbamoyl, N-(pyridyl(lower) alkyl)-N-(lower)alkoxy(lower)alkyl)carbamoyl-arylcarbamoyl, pyridylcarbamoyl, pyridyl(lower) alkylcarbamoyl, amino acid residue substituted with a pyridyl group and amino acid residue substituted with pyridyl(lower)alkyl, A is lower alkylene, and Y is a leaving group, or its salt to give a compound of the formula:

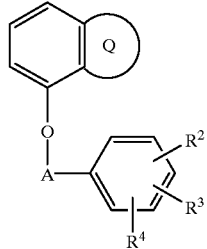

wherein a group of the formula:

$R^2$, $R^3$, $R^4$ and A are each as defined above, or its salt.

* * * * *